US010828359B2

(12) United States Patent
Fan et al.

(10) Patent No.: US 10,828,359 B2
(45) Date of Patent: Nov. 10, 2020

(54) ANTI-*MYCOBACTERIUM TUBERCULOSIS* VACCINE USING SENDAI VIRUS AS VECTOR

(71) Applicants: Shanghai Public Health Clinical Center, Fudan University, Shanghai (CN); ID Pharma Co., Ltd., Tokyo (JP)

(72) Inventors: Xiao-Yong Fan, Shanghai (CN); Tsugumine Shu, Ibaraki (JP); Zhi-Dong Hu, Shanghai (CN); Douglas B. Lowrie, Shanghai (CN)

(73) Assignees: Shanghai Public Health Clinical Center, Fudan University, Shanghai (CN); ID Pharma Co., Ltd., Tokyo (JP)

( * ) Notice: Subject to any disclaimer, the term of this patent is extended or adjusted under 35 U.S.C. 154(b) by 135 days.

(21) Appl. No.: 15/568,117

(22) PCT Filed: Apr. 19, 2016

(86) PCT No.: PCT/CN2016/079660
§ 371 (c)(1),
(2) Date: Oct. 20, 2017

(87) PCT Pub. No.: WO2016/169467
PCT Pub. Date: Oct. 27, 2016

(65) Prior Publication Data
US 2018/0085449 A1 Mar. 29, 2018

(30) Foreign Application Priority Data
Apr. 20, 2015 (CN) .......................... 2015 1 0187738

(51) Int. Cl.
*A61K 39/04* (2006.01)
*C12N 15/86* (2006.01)
*A61K 39/155* (2006.01)
*A61K 39/00* (2006.01)

(52) U.S. Cl.
CPC .............. *A61K 39/04* (2013.01); *C12N 15/86* (2013.01); *A61K 2039/5256* (2013.01); *A61K 2039/543* (2013.01); *A61K 2039/70* (2013.01); *C12N 2760/18634* (2013.01); *C12N 2760/18643* (2013.01); *C12N 2760/18834* (2013.01); *C12N 2760/18843* (2013.01)

(58) Field of Classification Search
None
See application file for complete search history.

(56) References Cited

FOREIGN PATENT DOCUMENTS

| CN | 1362885 | | 8/2002 | |
| CN | 102268446 A | | 12/2011 | |
| CN | 102272301 A | | 12/2011 | |
| CN | 103189506 A | * | 7/2013 | ............. A61K 39/39 |
| CN | 103304670 A | | 9/2013 | |
| WO | WO 2005/099750 A1 | | 10/2005 | |
| WO | WO 2012/053646 A1 | | 4/2012 | |

OTHER PUBLICATIONS

CN 103189506 A—English Translation by Google; original dated Jul. 2013.*
Vordermeier et al. Cellular immune responses induced in cattle by heterologous prime—boost vaccination using recombinant viruses and bacille Calmette—Guériin, Immunology 2004; 112: 461-470.*
Hikono et al. Induction of a cross-reactive antibody response to influenza virus M2 antigen in pigs by using a Sendai virus vector. Veterinary Immunology and Immunopathology. 2012; 146(1): 92-96.*
Duan et al., Efficient protective immunity against Trypanosoma cruzi infection after nasal vaccination with recombinant Sendai virus vector expressing amastigote surface protein-2. Vaccine. Oct. 19, 2009;27(44):6154-9. doi:10.1016/j.vaccine.2009.08.026. Epub Aug. 25, 2009.
Hara et al., Mucosal immunotherapy in an Alzheimer mouse model by recombinant Sendai virus vector carrying Aβ1-43/IL-10 cDNA. Vaccine. Oct. 6, 2011;29(43):7474-82. doi: 10.1016/j.vaccine.2011.07.057. Epub Jul. 29, 2011.
Hu et al., Sendai Virus Mucosal Vaccination Establishes Lung-Resident Memory CD8 T Cell Immunity and Boosts BCG-Primed Protection against TB in Mice. Mol Ther. May 3, 2017;25(5):1222-1233. doi:10.1016/j.ymthe.2017.02.018. Epub Mar. 23, 2017.
Jones et al., Sendai virus-based RSV vaccine protects against RSV challenge in an in vivo maternal antibody model. Vaccine. May 30, 2014;32(26):3264-73. doi: 10.1016/j.vaccine.2014.03.088. Epub Apr. 14, 2014.
Le et al., Induction of influenza-specific mucosal immunity by an attenuated recombinant Sendai virus. PLoS One. Apr. 18, 2011;6(4):e18780. doi: 10.1371/journal.pone.0018780.
Mason et al., Influence of antigen insertion site and vector dose on immunogenicity and protective capacity in Sendai virus-based human parainfluenza virus type 3 vaccines. J Virol. May 2013;87(10):5959-69. doi:10.1128/JVI.00227-13. Epub Mar. 20, 2013.
Okada et al., Novel prophylactic vaccine using a prime-boost method and hemagglutinating virus of Japan-envelope against tuberculosis. Clin Dev Immunol. 2011;2011:549281. doi: 10.1155/2011/549281. Epub Mar. 7, 2011.
Zhang et al., Elicitation of both anti HIV-1 Env humoral and cellular immunities by replicating vaccinia prime Sendai virus boost regimen and boosting by CD40Lm. PLoS One. 2012;7(12):e51633. doi10.1371/journal.pone.0051633. Epub Dec. 7, 2012.

(Continued)

*Primary Examiner* — Nianxiang Zou
(74) *Attorney, Agent, or Firm* — Wolf, Greenfield & Sacks, P.C.

(57) ABSTRACT

Provided in the present application are a recombinant sendai virus vector vaccine expressing immunodominant antigens of *Mycobacterium tuberculosis*, and can be used as therapeutic and preventive antituberculosis vaccine.

17 Claims, 15 Drawing Sheets

Specification includes a Sequence Listing.

(56) References Cited

OTHER PUBLICATIONS

Guguang et al., Research on the clinical application plan of new tuberculosis treatment vaccines and Combined therapy plan with new chemotherapeutic agents. 2010;99-105.

Li et al., A cytoplasmic RNA vector derived from nontransmissible Sendai virus with efficient gene transfer and expression. J Virol. Jul. 2000;74(14):6564-9.

Shao et al., Research progress on nucleic acid vaccine. National Insitutes Food Drug Control. 2013.

Tchilian et al., Immunization with different formulations of *Mycobacterium tuberculosis* antigen 85A induces immune responses with different specificity and protective efficacy. Vaccine. Sep. 23, 2013;31(41):4624-31. doi: 10.1016/j.vaccine.2013.07.040. Epub Jul. 27, 2013.

\* cited by examiner

US 10,828,359 B2

ANTI-*MYCOBACTERIUM TUBERCULOSIS* VACCINE USING SENDAI VIRUS AS VECTOR

RELATED APPLICATIONS

This Application is a national stage filing under 35 U.S.C. § 371 of International Application No. PCT/CN2016/079660, entitled "ANTI-*MYCOBACTERIUM TUBERCULOSIS* VACCINE USING SENDAI VIRUS AS VECTOR", filed Apr. 19, 2016, which claims priority to Chinese patent application number 201510187738.8, filed on Apr. 20, 2015, entitled "ANTI-*MYCOBACTERIUM TUBERCULOSIS* VACCINE USING SENDAI VIRUS AS VECTOR", the entire contents of each of which are incorporated by reference herein.

FIELD OF THE INVENTION

The present application relates to an anti-*Mycobacterium tuberculosis* vaccine using Sendai virus as vector. The present application also relates to a method of vaccination with a Sendai virus vector and its use in the prevention or treatment of *Mycobacterium tuberculosis* infection.

BACKGROUND OF THE INVENTION

*Tuberculosis* is one of the major killers that affect human health. As a pathogen of *tuberculosis* (TB), *Mycobacterium tuberculosis* is the leading cause of death in the world's bacterial infections—the latent infection affects one third of the world's population. According to the latest report of the World Health Organization, there were 8.6 million new cases and 1.3 million deaths in 2012. As one of the most effective ways to fight against infectious diseases in human history, vaccines play an important role in the prevention and control of many diseases. *Bacillus* Calmette-Guérin (BCG) is an attenuated strain derived from *Mycobacterium bovis*, and it is by far the only approved vaccine against TB. However, the effect of BCG on adults was found to be quite different, especially among different races. The effectiveness of BCG decreases with the increase of age, and thus it is not effective for preventing the disease in adults, especially in high TB areas. BCG vaccination has been used to prevent tuberculous meningitis and to facilitate the prevention of the spread of *Mycobacterium tuberculosis* to the lungs, but cannot prevent infection. Another limitation of the BCG vaccine is that parenteral delivery cannot induce potent T cell immunity in the lung mucosa, which is critical for the protection from *Mycobacterium tuberculosis*.

Several hypotheses have been proposed to explain the poor protective effects of BCG on *tuberculosis*, one of which is that BCG fails to induce adequate CD8+ T cell responses (see). Recent studies have shown that in addition to Th1-type CD4+ T cell immunity, induction of CD8+ T cell responses is essential for immunization against *Mycobacterium tuberculosis* infection.

The limitations of the effects of BCG and the global epidemic of TB have prompted researchers across the countries to generate new and more effective anti-TB vaccines. Vaccines based on live viral vectors have the ability to induce effective and sustained expression of antigen, which are one of the most widely studied vaccine vectors (Cairns, J S and Sarver, N. 1998, AIDS Research for Human Retroviruses Vol 14: 1501-1508; Hirsch, V M et al., 1996, Journal of Virology, vol 70: 3741-3752; Buge, S L et al., 1997, Journal of Virology, vol 71: 8531-8541). Among them, poxvirus and adenovirus vectors are the most widely studied vectors, and clinical trials with both have been completed. However, the stage II a clinical trials found that anti-*tuberculosis* poxvirus vector vaccines cannot induce adequate protective anti-TB immune responses. Studies suggest that viral vectors eliciting effective protective immune responses depend on many factors such as the level and persistence of antigen expression, the dynamics of vector virus replication, and the tendency and pathogenicity of the vector viruses etc. Currently available viral vectors have their own advantages and disadvantages. Therefore, the selection of the optimum viral vector-based immunization scheme requires accurate assessment and comparison.

A fatal drawback of a viral vector-based vaccine immunization scheme is that it induces strong immune responses against the vector virus other than the target antigen. This problem can be solved by using two or more different types of vector vaccines for "priming" and "boosting" respectively. Among them, priming with DNA vectors (hereinafter referred to as priming)—boosting with viral vectors is one of the most widely studied forms of immunization (Hanke, T. et al., 1999, Journal of Virology, Vol. 73, pp. 7524-7532; Robinson, H L et al., 1999, Nat. Med., Vol. 5: pp. 526-534). Therefore, it is still necessary to develop new types of viral vectors.

There is an urgent need to develop effective and safe *tuberculosis* vaccines in the field due to the increasing risk of *tuberculosis* mycobacterial infection and the global epidemic.

SUMMARY OF THE INVENTION

The present application provides a Sendai virus vector comprising a encoded *Mycobacterium tuberculosis* protein and a vaccine prepared from the vector. In particular, the present application provides a Sendai virus vector which expresses *Mycobacterium tuberculosis* protein Ag85 in a fusion and a vaccine thereof.

In a preferred embodiment, the encoded *Mycobacterium tuberculosis* protein is Ag85, which comprises an amino acid sequence selected from the group consisting of Ag85A, Ag85B, a fragment thereof, or a combination of any of the above. In one embodiment, the *Mycobacterium tuberculosis* protein comprises a chimera of the amino acid sequences of Ag85A and Ag85B proteins or a fragment thereof. In a further embodiment, the *Mycobacterium tuberculosis* protein comprises a chimera of the amino acid sequence of the Ag85A protein (SEQ ID No: 2) and the amino acid sequence of amino acids 125-282 (SEQ ID No: 5) of Ag85B (SEQ ID No: 8), wherein a gene encoding the amino acid sequence of amino acids 125-282 of Ag85B protein is inserted in the sequence of Ag85A gene, and the chimeric site is the positions 245-250 which is the recognition sequence of restriction endonuclease Kpn I and/or positions 430-435 which is the recognition sequence of endonuclease Acc I.

In one embodiment, the present application relates to the insertion of a *Mycobacterium tuberculosis* chimeric gene into a Sendai virus vector by a plasmid construction method known in the art, as described above, preferably the chimeric gene comprising a chimera of the coding sequence of Ag85A protein (SEQ ID No: 1) and a nucleotide sequence encoding amino acids 125-282 (SEQ ID No: 5) of Ag85B (SEQ ID No: 6 or 7), wherein the chimeric site is the positions 245-250 which is the recognition sequence of restriction endonuclease Kpn I and/or positions 430-435 which is the recognition sequence of endonuclease Acc I.

The present application also relates to a *Mycobacterium tuberculosis* Ag85 protein encoded by the chimeric gene.

In one embodiment, the Sendai virus vector (SeV) to which a gene encoding a *Mycobacterium tuberculosis* protein is inserted has a F gene defect. In particular, the Sendai virus vector lacks the F gene. In one embodiment, the constructed recombinant Sendai virus vector successfully express Ag85 protein in LLC-MK2 cells.

The present application further relates to the use of any of the recombinant Sendai virus vectors as described above in the preparation of a vaccine for the prevention and/or treatment of *Mycobacterium tuberculosis* infection or *tuberculosis*. In addition, the present application also relates to a method for the prevention and/or treatment of *Mycobacterium tuberculosis* infection or *tuberculosis*, comprising administering to a subject a vaccine of a recombinant Sendai virus vector as described above. Preferably, the *tuberculosis* is pulmonary *tuberculosis*.

In one embodiment, the invention provides a vaccine of any of the Sendai virus vectors as described above for use as an anti-*tuberculosis* preventive vaccine. In another embodiment, the present application provides any of the above Sendai virus vector vaccines that can be used as an anti-*tuberculosis* therapeutic vaccine.

In one aspect, the vaccine of the Sendai virus vector of the present application may be administered to the subject for one or more times by intranasal administration or intramuscular injection.

In one embodiment, the Sendai virus vector vaccine of the invention is vaccinated at least once in the form of a multivalent vaccine. In particular, the Sendai virus vector vaccine is administered in combination with a BCG vaccine, and the administration of the BCG vaccine may be performed before, simultaneously with, or after the administration of the Sendai virus vector vaccine. Preferably, the subject has previously received primary immunization with the BCG vaccine and then boosted with the Sendai virus vector vaccine of the present application. The present application also provides the use of a recombinant Sendai virus vector vaccine as described above and optionally at least one additional immunological agent for the prevention of *Mycobacterium tuberculosis* infection in a subject, wherein said additional immunological agent may be a BCG vaccine or any other immunological agent expressing the immune dominant antigen of *Mycobacterium tuberculosis*, such as a nucleic acid vaccine or a recombinant subunit vaccine. Preferably, the present application provides the Sendai virus vector vaccine as described above in combination with the BCG vaccine for use in the prevention of *tuberculosis*.

In one embodiment, the present application provides the use of a Sendai virus vector encoding the above-mentioned *Mycobacterium tuberculosis* protein in the preparation of a vaccine for the treatment of *tuberculosis*. The present application also provides the use of a recombinant Sendai virus vector vaccine as described above for the treatment of a subject suffering from *tuberculosis*, optionally the recombinant Sendai virus vector vaccine is administrated in combination with at least one additional *Mycobacterium tuberculosis* therapeutic agent, wherein the additional *Mycobacterium tuberculosis* therapeutic agent may be rifampicin (RFP) or any other agent that inhibits *Mycobacterium tuberculosis*. Preferably, the present application provides the use of the Sendai virus vector vaccine as described above in combination with rifampicin for the treatment of *tuberculosis*.

The subject may be an animal infected with *Mycobacterium tuberculosis* or having *tuberculosis*, such as a mouse, or a human.

In one embodiment, the present application also provides a Sendai virus vector encoding a *Mycobacterium tuberculosis* protein for inducing a specific cellular immune response against the *Mycobacterium tuberculosis* protein. In another embodiment, the present application provides the use of a Sendai virus vector encoding a *Mycobacterium tuberculosis* protein in the manufacture of a medicament for inducing a specific cellular immune response against the *Mycobacterium tuberculosis* protein. In one embodiment, the recombinant Sendai virus vector of the present application induces a strong cellular immune response against the *Mycobacterium tuberculosis* protein in both the lung and spleen. In yet another embodiment, the recombinant Sendai virus vector of the present application induces a stronger cellular immune response against the *Mycobacterium tuberculosis* protein in the lung.

In one embodiment, the present application provides a method of inducing a specific cellular immune response against a *Mycobacterium tuberculosis* protein comprising: (a) introducing a Sendai virus vector that expresses a *Mycobacterium tuberculosis*-associated protein in a fusion into a antigen presenting cell; (b) contacting the antigen presenting cell with a cytotoxic T lymphocyte. The method may be performed in vitro, ex vivo or in vivo. In particular, the encoded *Mycobacterium tuberculosis* protein is Ag85, which comprises an amino acid sequence of a protein or a fragment selected from the group consisting of Ag85A, Ag85B, a fragment thereof, or a combination of any of the above. In one embodiment, the *Mycobacterium tuberculosis* protein comprises a chimera of the amino acid sequence of the Ag85A protein (SEQ ID No: 2) and the amino acid sequence of amino acids 125-282 (SEQ ID No: 5) of Ag85B (SEQ ID No: 8), wherein a gene encoding the amino acid sequence of amino acids 125-282 of Ag85B protein is inserted in the sequence of Ag85A gene, and the chimeric site is the positions 245-250 which is the recognition sequence of restriction endonuclease Kpn I and/or positions 430-435 which is the recognition sequence of endonuclease Acc I.

In one embodiment, the present application provides a vaccine composition comprising any of the recombinant Sendai virus vectors as described above and at least one pharmaceutically acceptable carrier or vehicle. In one embodiment, the pharmaceutically acceptable carrier is an adjuvant. Preferably, the adjuvant is levamisole.

In one embodiment, the present application relates to a Sendai virus vector encoding the *Mycobacterium tuberculosis* protein Ag85AB, which has been deposited in the China Center for Type Culture Collection (CCTCC, Wuchang Luojia Moutain, Wuhan, 430072), the classification of the vector is Paramyxoviridae/Paramyxoviruses, the deposite date is Apr. 19, 2015 and the deposit number CCTCC V201518.

In particular, the present application relates to the following:

1. A Sendai virus vector vaccine, wherein said vector expresses a *Mycobacterium tuberculosis* immunogenic antigen, and preferably expresses *Mycobacterium tuberculosis* secreted protein Ag85.

2. The vaccine of item 1, wherein the expressed *Mycobacterium tuberculosis* antigen comprises an amino acid sequence of a Ag85A protein, and/or a Ag85B protein, and/or a portion thereof and an chimera of the foregoing.

3. The vaccine of item 1 or 2, wherein the used vector is a F gene defective Sendai virus vector.

4. Use of the Sendai virus vector vaccine of any of items 1-3 as an anti-*tuberculosis* preventive vaccine.

5. The use of item 4, wherein the vaccine is immunized by intranasal vaccination.

6. The use of item 4 or 5, wherein the vaccine is vaccinated at least once in the form of a multivalent vaccine.

7. Use of the Sendai virus vector vaccine according to any of items 1 to 3 as an anti-*tuberculosis* therapeutic vaccine.

8. A method of inducing a specific cellular immune response against a *Mycobacterium tuberculosis* protein comprising: (a) introducing a Sendai virus vector that expresses a *Mycobacterium tuberculosis* associated protein in a fusion into an antigen presenting cell; (b) contacting the antigen presenting cell with a cytotoxic T lymphocyte, wherein the *Mycobacterium tuberculosis* protein comprises a protein selected from the group consisting of Ag85A, Ag85B, a fragment thereof, or any combination of any of the above.

9. The method of claim 8, where in the method is performed in vitro.

10. Use of a Sendai virus vector encoding *Mycobacterium tuberculosis* protein Ag85 in the manufacture of a medicament for inducing a specific cellular immune response against the protein, wherein the *Mycobacterium tuberculosis* Ag85 protein comprises a protein selected from the group consisting of Ag85A, Ag85B, a fragment thereof, or any combination of any of the above.

11. A recombinant Sendai virus vector, which is deposited in China Center for Type Culture Collection, under the deposit number CCTCC V201518.

The foregoing summary is illustrative only and is not intended to be limiting in any way. In addition to the illustrative aspects, embodiments, and features described above, other aspects, embodiments, and features will be set forth in the following detailed description.

DESCRIPTION OF THE FIGURES

The foregoing and other features of the present disclosure will become more apparent from the following description and the appended claims in conjunction with the accompanying drawings. It is to be understood that these drawings only depict several embodiments in accordance with the present disclosure and are not intended to be construed as limiting the scope thereof, and that the disclosure will be described in greater detail and in part by the use of the accompanying drawings.

DETAILED DESCRIPTION OF THE INVENTION

Figure 1:
FIG. 1 shows the construction of the pSeV85AB plasmid in which the constructed chimera of Ag85A and Ag85B is inserted in a F gene defective SeV vector at the Not I site.
Figure 1:
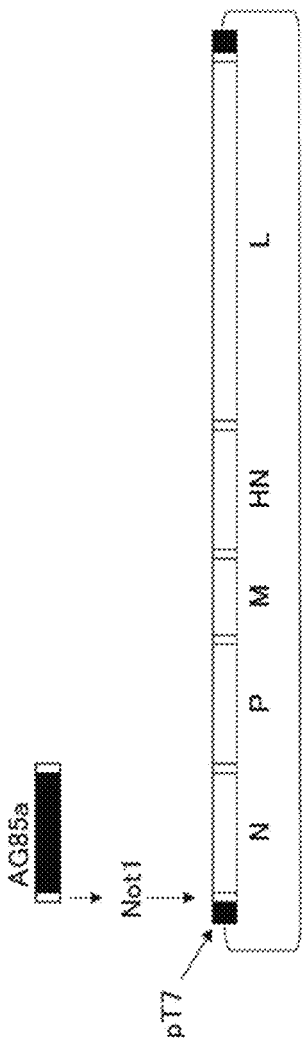
Figure 1:
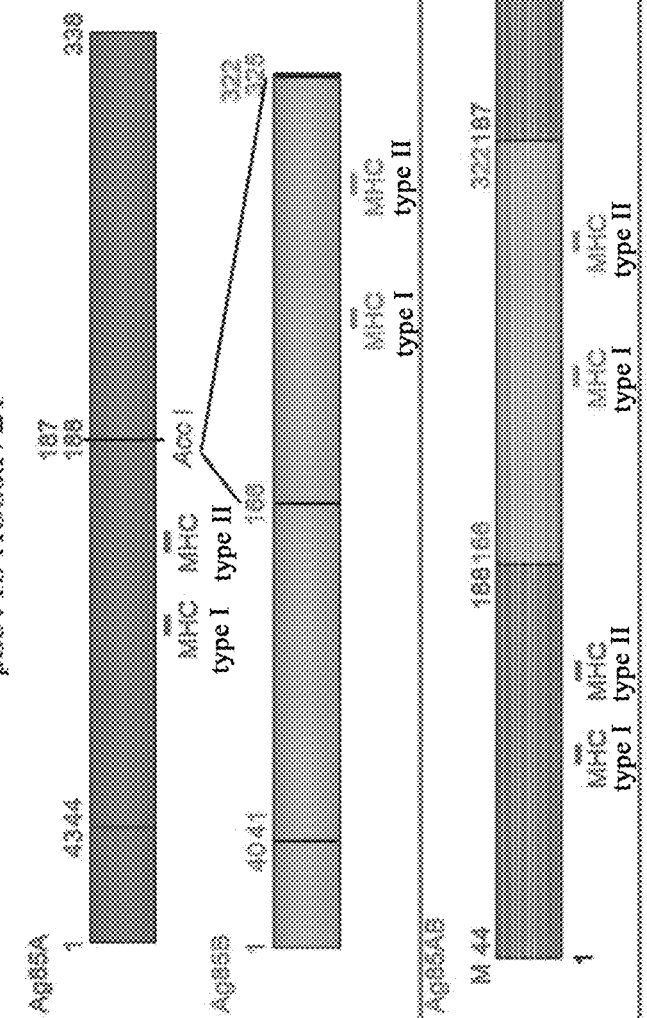

The present application provides a recombinant Sendai virus vector vaccine which expresses an immunogenic dominant antigen of *Mycobacterium tuberculosis* in a fusion. The vaccine can be used as a therapeutic and preventive anti-*tuberculosis* vaccine. By intranasally immunizing with the vaccine, the present inventors successfully and effectively induced a protective immune response against *Mycobacterium tuberculosis* and did not observe immunization induced pathological symptoms. As a preventive anti-*tuberculosis* vaccine, its intranasal vaccination in mouse models successfully induced a significant antigen-specific cellular immune response. Experiments on the protection of *Mycobacterium tuberculosis* challenge show that compared with the control animals, amount of *Mycobacterium tuberculosis* in the lungs and spleens of immunized mice was significantly reduced, and the mechanism relates to the strong antigen-specific T cell immune response occurred in the lungs, especially the CD8+ T cell immune response. Meanwhile, when used as therapeutic vaccine against *tuberculosis*, after immunotherapy for eight weeks, the amount of bacteria in the lungs and spleens of the mice is comparable to that of the rifampicin (RFP) treated group, and the vaccine enhances the therapeutic effect of RFP when used in combination with RFP.

The present vaccine uses at least one protein of *Mycobacterium tuberculosis*. According to the present application, effective immune responses can be induced even when only Ag85 antigen is expressed. In addition, the use of multiple types of proteins as antigens, can achieve a higher immunity. The used *Mycobacterium tuberculosis* Ag85 protein, while the sequences of amino acids 1-125 of *Mycobacterium tuberculosis* Ag85A and Ag85B antigen proteins have little difference from each other, the amino acid sequences of positions 125-282 are quite different, with about 40 amino acids are different. There are more than 90 bases in the coding nucleic acid sequence of this segment. In this segment, Ag85B has an important epitope that can induce Th1-type response response and cytokines IFN-γ and IL-2 (S. D'Souza, V. Rosseels, M. Romano, A et al; Mapping of Murine Th1 Helper T-Cell Epitopes of Mycolyl Transferases Ag85A, Ag85B, and Ag85C from *Mycobacterium tuberculosis*. Infection and Immunity, January 2003, 71(1): 483-493).

The inventors of the present application searched the antigenic epitopes of the gene of *Mycobacterium tuberculosis* structural protein Ag85A by the Epitope Informatics software from the Intenet-Based Applied Bioinformatics Company and found that the antigenic epitopes are mainly concentrated at the amino terminal and the carboxyl terminal of Ag85A (S. D'Souza, V. Rosseels, M. Romano, A et al; Mapping of Murine Th1 Helper T-Cell Epitopes of Mycolyl Transferases Ag85A, Ag85B, and Ag85C from *Mycobacterium tuberculosis*. Infection and Immunity, January 2003, 71(1): 483-493). In the intermediate segment of Ag85A parent gene which does not contain a antigenic epitope, positions 245-250 contains a Kpn I cutting site (GGTACC), and positions 430-435 contains a Acc I cutting site (GTCTAC), and thus it was designed to chimerically insert a nucleotide sequence encoding amino acids 125-282 of Ag85B into this segment.

In the present application, the *Mycobacterium tuberculosis* protein coding gene inserted into the Sendai virus vector may be a polynucleotide sequence encoding Ag85A, Ag85B, a fragment thereof, or any combination of any of the above, and may be a derivative or variant of the polynucleotide sequence. The derivative or variant has at least 70% homology to the polynucleotide sequence encoding Ag85A, Ag85B protein or a fragment thereof, preferably having at least 75% homology, more preferably having at least 80% homology, more preferably having at least 85% homology, preferably having at least 90% homology, more preferably having at least 95% homology, and more preferably having at least 96%, 97%, 98%, 99% homologous, as long as the protein encoded by the nucleotide sequence has the same immunogenicity as Ag85A, Ag85B protein or a fragment thereof or any combination thereof.

The present inventors have previously established an effective antigen expression system using a recombinant Sendai virus (SeV) (Kato, A. et al., 1996, Gene Cell Vol. 1: pp. 569-579). Type 1 mouse parainfluenza virus SeV is an enveloped virus with a non-segmented negative strand RNA genome, and belongs to the paramyxovirus genus (Nagai, Y. 1999, Rev. Med. Virol. Volume 9: pp. 83-99). The virus causes fatal respiratory disease in mice, but is not pathogenic to nonhuman primates and humans (Nagai, Y. 1999, Rev. Med. Virol. Volume 9: pp. 83-99; Hurwitz, J. L. et al., Vaccine, Vol. 15: 533-540, 1997).

Since Sendai virus is replicated in the cytoplasm, the antigenic protein can be efficiently expressed by means of a recombinant Sendai virus vector vaccine independent of the nucleus. More importantly, infection with a Sendai virus vector does not cause cell division, and thus the foreign gene can be efficient and sustained expressed. For example, the amount of gp120 of type 1 human immunodeficiency virus (HIV-1) Env protein expressed by a recombinant human Sendai virus vector is up to 6 μg/ml in the culture supernatant (equivalent to 6 micrograms per $10^6$ cells), which is the highest for vectors used in mammalian cell culture systems (Yu, D. et al. 1997, Gene Cells, vol. 2: pages 457-466).

Since the replication of SeV requires modification of the coated protease, its replication tendency is limited to specific tissues such as respiratory epithelial cells (Nagai, Y., 1993, Trends Microbiol., Vol. 1: pp. 81-87). And it is expected that it will not spread to tissues other than the respiratory tract, suggesting that the SeV vector and its replication active form also have advantages in terms of safety.

The present inventors constructed an anti-*tuberculosis* recombinant Sendai virus vector vaccine expressing the immunogenic dominant antigen Ag85A and Ag85B of *Mycobacterium tuberculosis*, named SeV85AB, using F gene-deficient SeV as a vector. Western Blot confirmed that the recombinant vaccine was capable of efficiently expressing the chimeric proteins of the two *Mycobacterium tuberculosis* proteins.

On the one hand, we used the vaccine as a preventive vaccine against *Mycobacterium tuberculosis* in a mouse model to assess its preventive effect on *Mycobacterium tuberculosis* infection. Specifically, in the a SPF laboratory, Balb/c mice (female, 6-8 weeks old) were immunized by intranasal or intramuscular injection using a dose of $10^7$ CIU of SeV85AB. BCG immunization and PBS were used as controls. Four weeks After immunization, on the one hand, the mice were sacrificed, the lungs and spleen organs were collected, and digested into single cell suspensions after sterile homogenization. Antigen specific peptides and PPD were used for in vitro stimulation, and the ability to secrete cytokines of these cells after specific stimulation was assessed by ELISPOT and polychromatic flow methods. On the other hand, the immunized mice were delivered to a P3 laboratory for aerial attack of the *Mycobacterium tuberculosis* H37Rv strain. After 4 weeks of challenge, the lung and spleen tissues were homogenized and the CFU colonies were counted to analyse the protection efficiency of the vaccine on the mice. Experimental results show that immunization with SeV85AB, especially through intranasal vaccination, can induce a strong antigen-specific immune response in mice, and a single-dose immunization can produce a comparative protection effect against *Mycobacterium tuberculosis* attack as the BCG vaccine; if using the BCG priming-SeV85AB enhancing strategy, the protection efficiency against *Mycobacterium tuberculosis* attack on mice can be significantly improved.

On the other hand, we use this vaccine as a therapeutic vaccine against *Mycobacterium tuberculosis* in a mouse model to assess its therapeutic effect on *Mycobacterium tuberculosis* infection. Specifically, in a P3 laboratory, Balb/c mice (female, 6-8 weeks old) were infected with *Mycobacterium tuberculosis* H37Rv strain (aerosol attack, 100 CFU). The mice were treated with intranasal administration of three doses of $10^7$ CIU of SeV85AB at week 4, week 6 and week 8, and the control group was treated with intranasal administration of PBS, while in the drug group, Rifampicin (RFP) at a dose of 10 mg/kg/day was added in the drinking water of the mce. At week 4, week 6, week 8 and week 12 after infection, 3-4 mice in each group were sacrificed to analysis the therapeutic effect of SeV85AB. The results showed that 8 weeks after SeV85AB immunotherapy, the amount of bacteria in lungs and spleens of the mice was comparable to that of RFP drug treatment groups. In another independent trial, RFP was added in the drinking water of mice, or the mice received intranasal administration of $10^7$ CIU of SeV85AB with simultaneous RFP treatment, and the mice were treated every other week for three times. The control group was vaccinated with PBS only. One week after the end of treatment, lung tissues of the mice were taken and homogenized, and then CFU colonies counting was performed to analysis the therapeutic effect. The results showed that the combined treatment of RFP+SeV85AB significantly reduce the number of colonies in the lungs of the mice compared with the group of RFP treatment alone, demonstrating that the recombinant virus had a good immunotherapy effect as an anti-*tuberculosis* vaccine and when used in combination with anti-*tuberculosis* drugs, a better therapeutic effect can be achieved.

Intranasal vaccination has the advantage of inducing mucosal immune response. retropharyngeal LN and submandibular LN are the first LNs in which lymphocytes from nasal cavity flow into (Suen, J Y, and Stern, S J 1996, "Head and Neck Cancer," Third Edition, E N Myers and J Y Suen, eds., W B Saunders, Philadelphia, pp. 462-484, Cancer of the neck). These LNs are likely to be involved in the mucosal immune response. Studies have shown that NALT (nasal associated lymphoid tissue) is an important component of the mucosal immune response (Yangagita, M. et al., 1999, Journal of Immunology, Vol 162, 3559-3565). By analyzing the cells prepared by Waldeyer's ring of mouse NALT, it was confirmed that SeV expression and immune response were present in the tissue. However, significant RNA was detected in both tissues when SeV expression in retropharyngeal LN and submandibular LN were detected. Since there is no protease necessary for the modification of SeV protein in these LNs (Nagai, Y. 1993, Microbiology Trends Vol 1: 81-87), it is predicted that there is no replication of SeV in LN. The mRNA in these LNs is derived from SeV-infected lymphocytes flowed from the nasal cavity. By using intranasal SeV vaccination, the antigen is efficiently expressed not only in the nasal mucosa, but also in the local LN, indicating the ability of SeV in inducing mucosal immune response (Gallichan, W S., and Rosenthal, K. L., 1996, Journal of Experimental Methods, Vol. 184, 1879-90).

The cellular immune response is an important part for the body to control *Mycobacterium tuberculosis* infection and replication (Nature Reviews Immunology 1, 20-30 (October 2001)). Therefore, induction of *Mycobacterium tuberculosis* specific T cell immune response to TB infection protection is essential. In addition, given that *Mycobacterium tuberculosis* invades the body mainly through the respiratory tract and the lung, it is important to induce antigen specific immune response at the location of lung mucosal. The present inventors have demonstrated that immunization with SeV85AB can induce strong antigen specific T cell immune responses in the lungs of mice by ELISPOT, intracellular factor staining and tetramer staining and etc.

After vaccination of Sendai virus vector SeV or recombinant SeV85AB vaccine with F gene deletion, mice did not show symptoms of viral infection and death. Weight monitoring of mice also demonstrate that vaccination with the viral vector or recombinant vaccine did not result in abnormal changes in body weight of the vaccinated mice, thus demonstrating the safety of the vaccine.

In particular, the present application discloses for the first time that immunity mediated by recombinant SeV85AB results in a response against *Mycobacterium tuberculosis* in mice. Our results indicate that a cellular immune response specific to the antigen was effectively induced in all intranasally immunized mice. Antigen expression is localized and well controlled. These results suggest that the SeV system can be used as a vector for promising *tuberculosis* vaccines.

It is an object of the present application to provide a vaccine comprising a Sendai virus vector encoding a *Mycobacterium tuberculosis* protein. The vaccine of the present application can be suitably used for the prevention and treatment of *tuberculosis*. The present application also includes a vaccination method of a vaccine. In particular, the present application relates to:

(1) A vaccine comprising a Sendai virus vector encoding a *Mycobacterium tuberculosis* protein;

(2) The vaccine of (1), wherein the recombinant protein comprises Ag85A, and/or Ag85B proteins and/or a portion thereof and a chimera thereof as described above;

(3) The vaccine of (1) or (2), wherein the Sendai virus vector is a F gene deleted;

(4) A method of vaccination comprising inoculating a vaccine comprising a Sendai virus vector encoding a *Mycobacterium tuberculosis* protein;

(5) The method of (4), wherein the vaccine is vaccinated intranasally;

(6) The method of (4) or (5), wherein the vaccine is vaccinated at least once in the vaccination of multiple vaccines;

(7) A method of inducing a cellular immune response specific to a *Mycobacterium tuberculosis* protein, comprising the steps of (a) introducing a Sendai virus vector encoding a *Mycobacterium tuberculosis* protein in an antigen presenting cell and (b) contacting the antigen antigen presenting cell with T helper cells and cytotoxic T cells.

The term "vaccine" as used herein refers to a composition for the prevention or treatment of an infectious disease. The vaccine comprises an antigen or can express an antigen, so it can induce an immune response against the antigen. The vaccine of the present application comprises a Sendai virus vector and can be used in the desired form for the prevention or treatment of the infection, spread and epidemic of the pathogenic microorganisms.

"vaccinate" or "vaccination" refers to actively generate immunity (humoral immunity, cellular immunity, or both) in a living body or a culture system by vaccination. Thereby the infection, reproduction, transmission and/or epidemic of pathogens can be prevented. Further, it can inhibit the manifestation and/or progress of the disease after pathogen infection.

"Antigen" refers to a protein that comprises one or more epitopes and that can induce an immune response specific to the antigen by stimulating the immune system of the host. The immune response may be a humoral immune response and/or a cellular immune response. Although 3 to several amino acids may form an epitope, in a protein, an epitope typically contains about 7 to 15 amino acids, such as 8, 9, 10, 12, or 14 amino acids. Antigen is also known as immunogen. In the present application, when an antigen is expressed by a polynucleotides or a vector encoding the antigen, the polynucleotides or the vector is defined as an antigen. This can also be used as a component of the vaccine.

"immune response" or "immunological response" refers to a humoral immune response and/or a cellular immune response against an antigen or a vaccine. Humoral immune response refers to antibody-mediated immune responses. Cellular immune response refers to T lymphocytes and/or other leukocytes mediated immune responses. Cellular immunity should include, for example, the production of CTL, the production or activation of helper T cells. A cellular immune response can be determined by detecting cytokines or chemokines produced by activated T cells such as CD8+ T cells or other leukocytes. In addition, it can also be determined by known lymphocyte proliferation assays, CTL assays, or antigen-specific T cell assays.

"Recombinant" refers to a compound or composition produced by recombinant polynucleotides. Recombinant polynucleotides refer to polynucleotides that are not bound in nature. The expression of recombinant polynucleotides can result in recombinant proteins. In addition, a "recombinant" viral vector is defined as a viral vector constructed by genetically engineered recombinant polynucleotides or its amplified products.

The term "paramyxovirus" as used herein is defined as a virus of the Paramyxoviridae family. Paramyxovirus includes, but is not limited thereto. For example, Sendai virus, New castle disease virus, Mumps virus, measles virus, Respiratory syncytial virus, rinderpest virus, distemper virus, monkey parainfluenza virus (SV5), type I, type II and type III human parainfluenza virus and so on. Sendai virus can be wild-type strains, mutant strains, laboratory passaged strains, or artificially constructed strains and so on. Incomplete virus such as DI particles (Virology, 1994, Vol. 68: 8413-8417), and synthesized oligonucleotides can be used as substances for producing the vaccine of the present application.

The genes encoding the proteins of paramyxovirus include NP, P, M, F, HN, and L genes. In this context, "NP, P, M, F, HN, and L genes" respectively represent encoding the nucleocapsid protein, the phosphoprotein, the matrix protein, the fusion protein, the hemagglutinin-neuraminidase and the giant protein. The genes of each virus of the paramyxovirus subfamily are generally described below. In general, NP genes can also be expressed as "N genes".

| Paramyxovirus NP | P/C/V | M | F | HN - L |
| Rublavirus NP | P/V | M | F | HN (SH) L |
| Measles virus NP | P/C/V | M | F | H - L |

The accession number in database of nucleotide sequence of each gene of the Sendai virus belonging to Paramyxoviridae Respirovirus is for the NP gene refer to M29343, M30202, M30203, M30204, M51331, M5565, M69046, and X17218; for P gene refer to M30202, M30203, M30204, M55565, M69046, X00583, X17007 and X17008; for M gene refer to D11446, K02742, M30202, M30203, M30204, M69046, U31956, X00584 and X53056; for F gene refer to D00152, D11446, D17334, D17335, M30202, M30203, M30204, M69046, X00152 and X02131; For HN gene refer to D26475, M12397, M30202, M30203, M30204, M69046, X00586, X02808 and X56131; for L gene refer to D00053, M30202, M30203, M30204, M69040, X00587, and X58886.

The term "gene" as used in the present application is defined as a genetic material containing a nucleic acid such as RNA, DNA or the like. The gene can be a naturally occurring or a artificially designed sequence. The paramyxovirus vector used herein contains a foreign gene encoding a protein of *Mycobacterium tuberculosis* or a portion thereof. The foreign gene may be a natural *Mycobacterium tuberculosis* comprised gene or a fragment thereof. The exogenous gene may also include, for example, nucleic acids that encode a *Mycobacterium tuberculosis* protein that is defective, mutant, inactivated or fused with other proteins. In addition, "DNA" used herein includes single-stranded DNA and double-stranded DNA.

The term "*Mycobacterium tuberculosis*" as used herein refers to a pathogen causing *tuberculosis*. It can invade all organs of the body, with pulmonary *tuberculosis* is the most common form. *Mycobacterium tuberculosis* can be divided into a variety of strains according to the genomes and regions etc. For example, in China and Southeast Asia the Beijing family of *Mycobacterium tuberculosis* is prevalent. The strain used in the present application is a standard strain of *Mycobacterium tuberculosis*, i.e., H37Rv strain.

The term "Sendai virus vector" as used herein is defined as a vector from Sendai virus and used to transform a gene into a host cell. The Sendai virus can be ribonucleoprotein (RNP), and can also be infectious viral particles. Herein, "infectivity" is defined as the ability of the recombinant Sendai virus vector to transform a gene within the vector into a cell attacked by the vector, by its cell attachment and membrane fusion capabilities. The Sendai virus vector of the present application carries an exogenous gene encoding a *Mycobacterium tuberculosis* protein that can become an antigen in an expressible manner. The Sendai virus vector may have the same replication capacity as a wild-type vector and may also be attenuated by gene mutations. In addition, the Sendai virus vector of the present application may be a defective vector having no replication capacity. "Replication capacity" is defined as the capacity of a viral vector to replicate and produce infectious viral particles in infected cells.

The present application provides a vaccine of a Sendai virus vector comprising a gene of a *Mycobacterium tuberculosis* protein or a part thereof. The *Mycobacterium tuberculosis* protein encoded by the Sendai virus is not limited, as long as the protein is antigenic. *Mycobacterium tuberculosis* proteins include *Mycobacterium tuberculosis* structural proteins, regulatory proteins and modified proteins. These proteins or a portion of their polypeptides can be used for the production of vaccines. The present vaccine can be produced by constructing a Sendai expression vectors that express the above proteins or a portion thereof. These proteins can be either alone or in combination. In the present application, it is preferable to use SeV expressing a structural protein of *Mycobacterium tuberculosis*.

The present inventors have previously found that the gene expression of intramuscular vaccinated recombinant SeV vector in monkeys reaches a peak within one week after vaccination and lasts for at least 13 days. In addition, repeated administration can render the expression sustained. These features have the advantage of achieving rapid and sustained therapeutic effects when vaccinated with recombinant SeV vectors.

From a safety point of view, the SeV vector also exhibits the potential for a clinical application suitable for humans. First, in many vectors, expression of an exogenous gene requires that the transfected DNA must enters the nucleus, which is a major obstacle to the success rate of gene transfection. However, in the case of Sendai virus, expression of an exogenous gene is driven by both the cellular tubulin and its own RNA polymerase (L protein) in the cytoplasm. This indicates that SeV does not interact with the genome of the host cell, which avoids the problem regarding safety such as tumorigenesis. Second, SeV is known to be pathogenic to rodents and can cause pneumonia, but no pathogenicity to humans. This is also demonstrated by the fact that intranasal administration of wild-type SeV does not have a serious deleterious effect on nonhuman primates (Burwitz J. L. et al., Vaccine, 1997, vol. 15, pp. 533-540). These features of SeV indicate that the SeV vector is very safe when applied to humans and is expected to be one of the vectors capable of expressing antigenic proteins. In fact, in the present application, mice after SeV vaccination did not show any significant pathological symptoms, and no significant reduction in body weight was observed. The vaccine of the present application is particularly preferably used for vaccination targeting *Mycobacterium tuberculosis*. In other words, vaccination of the vaccine of the present application can induce immunity against *Mycobacterium tuberculosis* to achieve inhibition of infection and/or reproduction of *Mycobacterium tuberculosis*. The vaccine of the present application is preferably used for the prevention before infection and treatment after infection of *Mycobacterium tuberculosis*.

The SeV vector used for vaccination in the present application is not particularly limited. For example, an ideal SeV vector may be a vector having replication capacity and capable of self-propagating. For example, in the genome of wild-type SeV, the short 3' leader region is followed by six genes encoding N (nucleocapsid), P (phospho), M (matrix), F (fusion), HN (hemagglutinin-neuraminidase) and L (large) proteins, and has a short 5' non-transcribed tail at the other end. A vector capable of self-replication can be obtained by designing a genome having a structure similar to that described above. In addition, a vector for expressing a foreign gene can be obtained by inserting the foreign gene into the genome. The viral gene of the SeV vector can be arranged differently from the wild type.

The SeV vector for immunization of the present application can be defective in a portion of the genes contained in the wild type SeV. For example, in order to construct a SeV vector and express a gene, the proteins encoded by the NP, P/C and L genes are considered necessary, so genes encoding these proteins shall be included in the genome of the SeV vector. While when constructing the SeV vector, other genes, such as M, F and HN proteins can be supplied by trans-methods (Trans: other forms). An expression vector carrying the gene encoding these proteins can be co-transfected with an expression vector encoding the SeV vector genome to the host cell to construct the SeV vector. An expression vector encoding the viral genome may also be transfected into a host cell carrying the genes encoding these proteins, and the SeV vector can be constructed using the proteins provided by the host cell. The amino acid sequences of these proteins may be different from the sequences of the virus itself, and may be mutated or use a homologous gene of another virus, as long as it has a comparable or higher activity as the natural proteins in the nucleic acid transformation.

When the SeV vector is prepared in the form of RNP, it is not considered that the proteins encoded by the M, F and HN genes are necessary for intercellular transmission of the SeV vector. As long as the genome contained in the RNP comprises the M, F and HN genes, when introduced into the host cell, the product of these genes can be produced, and the infectious virus particles are produced. The RNP vector that produces the infectious virus may be a RNP containing genomic RNA encoding the N, P, M, F, HN and L genes and N, P and L proteins. When such a RNP is introduced into the cell, the viral genome is expressed and replicated by the action of N, P and L proteins, so that the infectious viral vector is amplified.

RNP can be introduced into a cell with lipofectamine reagents, polycationic liposomes, and the like. In particular, various transfection reagents may be used, such as DOTMA (Boehringer), Superfect (QIAGEN #301305), DOTAP, DOPE, DOSPER (Boehringer #1811169). Chloroquine may be added to prevent degradation in the nucleus (Calos M. P., American Academy of Sciences Annual Report, 1983, vol. 80, p. 3015). In the case of a replicative virus, the resultant virus can be amplified or passaged by re-infecting a cultured cell, a chicken embryo or an organism (e.g., mammals such as mouse).

In contrast, a SeV vector deficient in M, F and/or HN genes can also be used in the present application. These vectors can be re-constructed by providing the deficient gene products from exogenous sources. Such a vector, like a wild-type viruse, still attaches to a host cell and induces cell fusion. However, since the genome of the vector introduced into the cell lacks some of the above-mentioned genes, it is not possible to form an infectious sub-virus particles having the same infectivity as the original. Thus, these vectors can be used as very safe viral vectors with gene transduction capability for only once. The gene that is defective in the genome may be an F and/or HN gene. The expression vector encoding the genome of recombinant paramyxovirus with defective F gene, the expression vector of the F protein and the expression vector of NP, P/C and L proteins are co-transfected into the host cell to reconstruct the viral vector (WO00/70055 and WO00/70070). It can also be produced using host cells in which the F gene has been integrated in the genome. When these proteins are supplied exogenously, their amino acid sequences may be different from those of the wild type and may be mutated or using homologous proteins from another viruses, as long as they provide gene transformation activity comparable to or higher than that of the natural proteins.

A protein that is different from the coating protein from the viral genome may be contained in the viral envelope of the virus. These proteins are not subject to any limitations, and may include coating proteins of other virus such as vesicular stomatitis virus (VSV) G protein (VSV-G). Thus, the SeV vector constituting the vaccine of the present application comprises a pseudotyped viral vector comprising a coating protein from a virus that is not homologous to the viral genome.

At the same time, the SeV vector used in the vaccine of the present application may have a protein targeting an adhesion protein, a ligand or a receptor of a specific cell, or may contain these proteins in the extracellular region, and contain a chimeric protein of a polypeptide that originates from viral coating proteins in the intracellular region, thereby a vector targeting a specific tissue can be prepared. These proteins may be encoded by the viral genome or provided by the expression of a gene other than the viral genome (e.g., other expression vectors or genes of the chromosome of the host cell) during viral reconstruction.

In order to reduce the antigenicity against the SeV protein or to enhance the transcription efficiency and replication efficiency of the RNA, the viral gene contained in the SeV vector for the vaccine of the present application can be altered. In particular, at least one of the genes of the replication factor genes NP, P/C and L genes can be altered to enhance transcription or replication capacities. In addition, the HN protein, which is one of the structural proteins, has hemagglutinin activity and neuraminidase activity, and it is expected to enhance the stability of the virus in the blood if the activity of the former is attenuated. And it is expected to adjust the infectivity of the virus if the activity of the latter is altered. Likewise, when altering the F protein associated with membrane fusion, it is expected to modulate the fusing ability of the liposomes to fuse with a membrane. In addition, it is also expected to analyze the epitopes of possible antigenic molecules of F protein and HN protein on the cell surface, and using them to produce SeV with reduced ability of antigen expression.

In addition, SeV lacking the modified gene can also be used in the vaccine of the present application. For example, SeV has significantly reduced pathogenicity in mice when a modified gene V gene of SeV has been removed, although it does not affect the expression and replication of the gene in cultured cells (Kato, A et al., 1997, Journal of Virology, Vol 71, pp: 7266-7272; Kato, A et al., 1997, EMBO J. Vol 16, pp: 578-587; Curran, J. et al., WO01/04272, EP1067179). Such an attenuated vector is particularly preferred as the vector for constituting the vaccine of the present application.

The viral vector used in the vaccine of the present application encodes a *Mycobacterium tuberculosis* protein or a portion of the protein in its genomic RNA. A recombinant SeV vector expressing a foreign gene can be obtained by inserting a foreign gene into the genome of the SeV vector as mentioned above. The foreign gene may be a gene fragment encoding a *Mycobacterium tuberculosis* protein or a portion of the protein. Such a gene fragment may be a naturally occurring gene fragment encoding a *Mycobacterium tuberculosis* protein, or a gene encoding a protein obtained by modification of a natural protein such as a deficiency, substitution or insertion, as long as the protein encoded by the gene has at least a portion of the antigenicity comparable to the natural protein.

A *Mycobacterium tuberculosis* protein refers to a protein comprised in *Mycobacterium tuberculosis*. Studies have shown that the immune dominant antigens of H37Rv strain are Ag85A and Ag85B and the like. In the present application, it is preferable to use a SeV vector which expresses any one or these proteins or a portion thereof, or a mixture thereof. We constructed a SeV vector to express the full length of any of these proteins (including processed and unprocessed proteins) or a portion thereof, or a combination thereof. As a portion of the protein, its length and site are not limited as long as this portion has the activity of the antigen. For example, it may be a polypeptide comprising one or more epitopes. Such a polypeptide typically contains at least three to several adjacent amino acids in the amino acid sequence of the *Mycobacterium tuberculosis* protein, and preferably contains about 7 to about 15 amino acids in an amino acid sequence of a *Mycobacterium tuberculosis* protein, for example, 8, 9, 10, 12 or 14 amino acids.

The vaccine uses at least one protein of *Mycobacterium tuberculosis*. According to the present application, effective immune induction can be achieved even when only Ag85 antigen is expressed. In addition, the use of multiple types of proteins as antigens can achieve a higher immunity.

In addition, the vaccine may use a protein from one *Mycobacterium tuberculosis* strain, but if the bacterial proteins obtained from a plurality of strains are used as antigens, an immunity against a broader scope of *Mycobacterium tuberculosis* strains can be achieved. In the case of using a plurality of strains as antigens, the combination among them is not limited. For example, a vaccine can be produced using genes derived from various isolated strains.

Multiple *Mycobacterium tuberculosis* genes can be integrated into different SeV vector genomes to construct SeVs and use their combination, or multiple genes can be integrated into the same SeV vector genome to express these genes.

In order to construct a SeV expressing a *Mycobacterium tuberculosis* protein, for example, a gene encoding a *Mycobacterium tuberculosis* protein can be inserted into DNA encoding the SeV genome (SeV vector DNA). When inserting the foreign gene into the SeV vector DNA, it is required to insert a sequence containing a number of nucleotides which is a multiple of six (Calain P. and Roux L., Journal of Virology, 1993, 67 (8), pp. 4822-4830). The foreign gene may be inserted upstream and/or downstream of each SeV gene (NP, P, M, F, HN and L genes). In order not to interfere with the expression of the upstream and downstream genes, a E-I-S sequence (transcription termination sequence-mediated sequence-transcription initiation sequence) or a part thereof may be inserted upstream or downstream of the foreign gene so that a E-I-S sequence is present between each of the genes. Alternatively, the foreign gene can be expressed by inserting IRES.

The expression level of the inserted foreign genes can be regulated by the type of the transcription initiation sequence attached to the upstream of these genes. It can also be regulated by the insertion site and the sequence before and after the gene. For example, in SeV, the closer the insertion site to the 3' terminal of the negative strand RNA of the viral genome (the closer to the NP gene in the wide type viral genome), the higher the expression level of the inserted gene. In order to achieve a high expression of the foreign gene, it is preferable to insert the foreign gene into the upstream region of the negative strand genome, such as the upstream of NP gene (3' region of the negative strand), or between the NP and P genes. In contrast, the closer the insertion site to the 5' end of the negative strand RNA (the closer to L gene of the wild-type viral genome), the lower expression level of the inserted gene. In order to reduce the expression of a foreign gene, it can be inserted at the most 5' end of the negative strand, i.e. downstream of the L gene of the wild-type viral genome (5' region of the L gene of the negative strand) or upstream of the L gene (3' region of the L gene in negative strand). It can be seen that in order to obtain the desired expression level of a foreign gene, the insertion site of the foreign gene can be appropriately adjusted, or adjusted by the combination of the genes encoding the viral proteins before and after. For example, when a high titer of a viral vector is applied, a toxicity will occur due to high expression of the introduced gene. In this case, in addition to control the titer of the virus being applied, it is also possible to design the insertion site of the foreign gene close to the 5' terminal region of the negative strand or by using an transcription initiation sequence with low efficiency.

In general, a high expression of the antigenic protein is advantageous because of the absence of cytotoxicity. Therefore, it is preferred to link the gene encoding the antigenic protein with a high efficient transcription initiation sequence, and insert the gene close to the 3' terminal of the negative strand genome. Examples of preferred vectors include a vector in which the *Mycobacterium tuberculosis* protein is at the 3' of any viral protein of paramyxovirus in the negative strand genome of the paramyxovirus vector. For example, it is preferred that the antigen gene is inserted into the upstream of the N gene (the 3' of the negative strand), or the antigen gene is inserted immediately downstream of the N gene.

In order to facilitate the insertion of a foreign gene, a cloning site can be designed at the insertion site. For example, the cloning site may be a recognition sequence of a restriction enzyme. The foreign gene can be inserted into the restriction site of the viral vector DNA. The cloning site may also be a multiple cloning site containing recognition sequences of multiple restriction enzymes. The vector for using in the vaccine of the present application may contain other exogenous genes in a position other than the site in which the *Mycobacterium tuberculosis* protein is inserted as described above. Such a foreign gene is not limited, and it may be a gene of a cytokine or chemokine associated with immune induction, or it may be other genes.

A recombinant Sendai virus vector containing an exogenous gene can be prepared according to Hasan, M. K., et al., Journal of Genetic Virology, Vol. 78: 2813-2820, 1997; Yu D. et al., Gene Cells, 1997, 2,457-466, as described below.

First, a DNA sample containing cDNA sequence is of the desired foreign gene prepared. Preferably at a concentration of 25 ng/ml or higher, and the DNA sample of a single plasmid is tested by electrophoresis. The following description is an example of inserting a foreign gene into the NotI site of the viral genomic DNA. If a Not I site is present in the cDNA to be inserted, it is necessary to remove the site in advance by altering the nucleotide sequence without changing the amino acid sequence of the encoded protein by the site-directed mutagenesis method. PCR was performed on the DNA sample to amplify and recover the desired DNA fragment. In order to make the amplified fragment to have Not I sites in both ends, and attach the transcription termination sequence (E), the mediator sequence (I) and the transcription initiation sequence (S) (EIS sequence) of Sendai virus at one end, a primer pair of a forward primer (sense strand) and a reverse primer (anti-sense strand) containing the NotI restriction site, the transcription termination sequence (E), the intermediate sequence (I), the transcription initiation sequence (S) and a portion of the gene of interest was synthesized.

For example, the forward synthetic DNA sequence contains any two or more nucleotides at the 5' terminal to ensure the success digestion of NotI (preferably not containing 4 nucleotides that originate from NotI recognition site such as GCG and GCC, more preferably ACTT). The NotI recognition sequence GCGGCCGC is added at the 3' terminal of the sequence. In addition, any 9 or 9 plus a multiple of 6 nucleotides are added at the 3' terminal as a spacer. In addition, at the 3' terminal, a sequence of about 25 nucleotides corresponding to the ORF from the start codon ATG of the desired cDNA are added. Preferably, the 3' terminal of the synthesized forward oligomeric DNA contains about 25 nucleotides of the desired cDNA and the final nucleotide is G or C.

The reverse synthetic DNA sequence contains any two or more nucleotides at the 5' terminal (preferably not containing 4 nucleotides that originate from NotI recognition site such as GCG and GCC, more preferably ACTT). The NotI recognition sequence GCGGCCGC is added to the 3' end of the sequence. In addition, a spacer oligomeric DNA was added to 3' terminal of the sequence to adjust the length of the primer. The length of the oligomeric DNA including the NotI recognition sequence GCGGCCGC, the sequence complementary to cDNA, and the EIS sequence from the Sendai virus genome, is designed so that the total number of nucleotides is a multiple of 6 (the so-called "the rule of 6"; Kolakofski D. et al., Journal of Virology, 1998, vol. 72, pp. 891-899; Calain P. and Roux L., Journal of Virology, 1993, vol. 67: 4822-4830). In addition, a sequence complementary to the S sequence of Sendai virus, preferably 5'-CTTTCAC-CCT-3', a sequence complementary to the I sequence, preferably 5'-AAG-3', and a sequence complementary to the E sequence, preferably 5'-TTTTTCTTACTACGG-3' are added to the 3' terminal of the added sequence. Finally, a complementary sequence of about 25 nucleotides of the desired cDNA from the stop codon to the upstream is added at the 3' terminal and make the final nucleotide is G or C. Thus, the 3' terminal of the reverse synthetic oligomeric DNA is prepared.

The PCR is carried out by a conventional method, for example, using ExTaq polymerase (TaKaRa). Preferably, Vent polymerase (NEB) is used, and the amplified DNA fragment is inserted into the NotI site of plasmid vector pBluescript after digestion with NotI. The nucleotide sequence of the PCR product is detected by an automated DNA sequencer. Plasmid with the correct sequence is selected. The inserted fragment is excised from the plasmid by NotI digestion and subcloned into the NotI site in a plasmid containing the paramyxovirus genomic cDNA. The PCR product can also be cloned into the NotI site of the latter plasmid directly without the pBluescript plasmid to obtain the recombinant Sendai virus cDNA.

For example, the method described in the literature (Yu, D. et al., Gene Cell, Vol. 2: 457-46, 1997; Hasan M. K et al., Journal of Genetic Virology, 1997, vol. 78: 2813-2820) can be used to construct the recombinant Sendai virus genomic cDNA. For example, a 18 bp spacer sequence (5'-(G)-CGGCCGCAGATCTTCACG-3') containing the NotI site is inserted into the adjacent locus between the leader sequence and the sequence encoding N protein of the cloned Sendai virus genomic cDNA (pSeV (+)), and obtain a plasmid pSeV18*b (+) which comprises the self-cleaved ribozyme site from the antisense strand of the hepatitis D virus (Hasan M. K et al., Journal of Genetic Virology, 1997, vol. 78: 2813-2820). The foreign gene fragment is inserted into the NotI site of pSeV18*b (+) to obtain recombinant Sendai virus cDNA in which the desired foreign gene has been inserted.

The recombinant paramyxovirus vector DNA produced accordingly is transcribed in vitro or into cells, and RNP is reconstructed in the presence of L, P and NP proteins to produce a viral vector containing RNP. The present application provides a method for producing a vaccine comprising a paramyxovirus vector encoding a *Mycobacterium tuberculosis* protein, the method comprises the step of transcribing the genomic DNA of the virus. The present application also provides DNA of the paramyxovirus vector which is produced from the DNA for the production of a component of the vaccine of the present application. The present application relates to the use of DNA encoding the genome of the paramyxovirus vector as a component of the vaccine of the present application. A virus can be reconstructed from a viral vector by known methods (WO97/16539; WO97/16538; Durbin A P et al., Virology, 1997, Vol. 235: pp. 323-332; Whelan S. P. et al., American Natural Science Process, 1995, Vol. 92, pp. 8388-8392; Schnell M. J. et al., EMBO J. 1994, vol. 13, pp. 4195-4203; Radecke F. et al., EMBO J. Vol. 14, pp. 5773-5784; Lawson N. D. et al., American Natural Science Process, 1995, vol. 92, pp. 4477-4481; Garcin D. et al., EMBO J., 1995, 6087-6094; Kato A. et al., Gene Cells, 1996, Vol. 1, pp. 569-579; Baron M. D. and Barrett T., Journal of Virology, 1997, Vol. 71, pp. 1265-1271; Bridgen A. and Elliott R. M, American Academy of Sciences Annual Report 1996, vol. 93: pp. 15400-15404). According to these methods a paramyxovirus virus vector can be reconstructed from the DNA, including parainfluenza virus, vesicular stomatitis virus, rabies virus, measles virus, rinderpest virus and Sendai virus and the like. If the F, HN and/or M genes are absent in the viral vector DNA, it alone cannot form infectious viral particles. These missing genes or genes encoding proteins from other viruses can be introduced into the host cells and expressed to produce infectious viral particles.

The method of introducing the vector DNA into a cell may include (1) forming a DNA precipitate which may be incorporated into the desired cell, (2) a method of forming a complex comprising positively charged DNA, which is suitable for incorporation into a desired cell, and has low cytotoxicity, and (3) using electrical pulses to rapidly open a sufficient pore on the desired cell membrane that allows DNA to pass through.

In (2), various transfection reagents such as DOTMA (Boehringer), Superfect (QIAGEN #301305), DOTAP, DOPE and DOSPER (Boehringer #1811169) can be used. For the method (1), calcium phosphate can be used for transfection. In this method, it is known that the DNA incorporated into the cell is absorbed into the phagocytic vesicles, but there are also sufficient amounts of DNA in the nucleus (Grahm F. L. and van Der Eb J., Virology, 1973, 52, 456; Wigler M. and Silverstein S., Cell, 1977, vol 11, p 223). Chen and Okayama have optimized the transformation techniques and reported that: (1) the culture conditions for cell and precipitation are 2 to 4% CO2, 35° C. for 15 to 24 hours, (2) cyclic DNA has a higher activity than linear DNA; and (3) when the concentration of DNA in the mixed solution is between 20 and 30 mg/ml, optimized precipitation can be obtained (Chen C. and Okayama H., Cell Molecular Biology, 1987, Volume 7, P. 2745). Method (2) is suitable for transient transfection. An earlier method is to mix the solution of DEAE-dextran (Sigma # D-9885 M. W. $5 \times 10^5$) with DNA at desired concentration ratio. Because most of the complexes are degraded in the nucleus, the efficiency of transfection can be enhanced by the addition of chloroquine (Calos M. P., Annual Report of the American Academy of Sciences, 1983, vol. 80, 3015). Method (3), known as the electroporation method, has a broader range of application than methods (1) and (2) because it can be used in any kind of cell. The efficiency is maximized under the conditions of the optimal duration of the pulse flow, the form of the pulse, the intensity of the electric field (the gap and voltage between the electrodes), the conductivity of the buffer, the DNA concentration and the cell density.

In the above three methods, method (2) is suitable for introducing DNA into a cell when reconstructing a vector because of it is easy to operate and can test a large number of samples using a large number of cells. It is preferred to use Superfect transfection reagent (QIAGEN, #301305) or DOSPER liposome transfection reagent (Boeringer Mannheim #1811169).

The reconstruction from cDNA can be carried out as follows:

In a 24-well-6-well plastic plate, or in a 100 mm dish, the cell line LLC-MK2 obtained from the monkey kidney was cultured in a limit essential medium (MEM) comprising 10% fetal bovine serum (FCS) and antibiotics (100 units/ml penicillin G and 100 mg/ml streptomycin) until 70-80% fusion. Then, the cells are infected by recombinant vaccinia virus vTF7-3 in the presence of 1 mg/ml psoralen at 2 pfu/cell, wherein the recombinant vaccinia virus vTF7-3 expresses T7 polymerase and has been exposure inactivated under UV for 20 minutes (Fuerst T. R. et al., American Natural Science Process, 1986, vol 83, pp: 8122-8126; Kato. A. et al., Gene Cells., 1996, vol 1, pp. 569-579). The amount of psoralen and the time of UV exposure can be adjusted appropriately. 1 hour after infection, for example, 2 to 60 mg, more preferably 3 to 5 mg recombinant Sendai virus cDNA and expression plasmids acting in a trans-manner that are required for the production of full-length Sendai virus genome (for example, 24-0.5 mg of pGEM-N, 12-0.25 mg pGEM-P, and 24-0.5 mg pGEM-L, or more preferably 1 mg pGEM-N, 0.5 mg pGEM-P, and 1 mg pGEM-L) are lipo-transfected into cells (Kato. A. et al., Gene Cells., 1996, vol 1, pp. 569-579). The transfected cells are cultured in serum-free MEM, which if desired, containing 100 mg/ml rifampicin (Sigma) and cytarabine (AraC) (Sigma), more preferably containing only 40 mg/ml Glycoside. The concentration of the drug can be adjusted to optimal, so that the vaccinia virus has the lowest cytotoxicity and the highest virus recovery (Kato. A. et al., Gene Cell, 1996, vol. 1: 569-579). After transfection, the cells are cultured for 48 to 72 hours, then the cells are recovered and the disrupted with three freeze-thaw cycles and transfected into LLC-MK2 cells. After culturing for 3-7 days, the culture medium is collected. In order to reconstruct a viral vector that lacks a gene encoding the coating protein that cannot replicate, the vector can be transfected into LLC-MK2 cells expressing the coating protein or co-transfected with a expression plasmid of the coating protein. LLC-MK2 cells expressing the coating cells may also be plated on the transfected cells and cultured for to propagate the deficient virus vector (WO 00/70055 and WO 0070070). The virus titer in the culture broth can be determined by measuring hemagglutinin activity (HA). And HA can be determined by the "end-point dilution method" (Kato. A. et al., Gene Cells, 1996, Vol. 1, 569-579; Yonemitsu Y. and Kaneda Y., Japanese Coagulans—Liposomes Gene transduction of microtubule cells, molecular biology of microtubule disease, molecular medicine methods, edited by Baker A. H, published by Humana, 1999, pp. 295-306). vTF7-3 which may be mixed (residual) may be removed by appropriately diluting (e.g., $10^6$ times) the obtained allantoic membrane sample and reamplifying in the egg. The re-amplification can be repeated 3 or more times. The resulting virus can be stored at −80° C.

The host cell for viral vector construction are not limited to any particular cell type as long as the viral vector can be reconstituted in the cell. Host cells may include LLC-MK2 cells, CV-1 cells obtained from monkey kidney, BHK cells obtained from hamster kidney, or cell lines derived from human origin. In order to obtain a large number of Sendai virus vectors, the vectors obtained from the above host cells can be used to infect embryogenic chicken eggs to amplify the vectors. The methods of producing viral vectors with chicken eggs are established (Advanced Technology Program III of Neuroscience Research, Neuroscience Molecular Physiology, edited by Nakanishi et al., Kouseisha, Osaka, 1993, pp. 153-172). Specifically, for example, the fertilized chicken eggs are incubated in a incubator at 37-38° C. for 9 to 12 days until they grow into embryos. The virus vector is vaccinated into the allantoic cavity, and the eggs are continuously cultured for several days. The conditions such as the time of culturing may vary depending on the type of recombinant Sendai virus used. Then, the allantoic fluid containing the virus is recovered. According to standard methods, Sendai virus vectors are isolated and purified from the allantoic samples (Tashiro M., virus protocol, Nagai and Ishihama eds., Medical observation, 1995, pp. 68-73).

For example, Sendai virus vectors with defective F protein can be constructed and prepared as follows (WO 00/70055 and WO 00/70070).

(1) Construction of Sendai Virus Genome cDNA with Defective F Gene and Expression Plasmid for F The full-length Sendai virus (SeV) genomic cDNA-pSeV18 (Hasan M K et al., Journal of Genetic Virology, 1997, vol. 78, pp. 2813-2820) (pSeV18+b(+), also known as pSeV18(+)), was digested with SphI and KpnI, and the resulting fragment (14673 bp) was recovered and cloned into pUC18 to obtain plasmid pUC18/KS. F defective area is constructed using pUC18/KS. The defection of F gene is performed by PCR-ligation method, and ORF (1698 bp) of F gene is removed finally, the F gene defective SeV genome is ligated with the sequence 5'-atgcatgccggcagatga (pSeV18+/ΔF), digested with EcoT221 and ligated, PCR product upstream of the F gene is obtained by the primers (Forward: 5'-gttgagtactgcaagagc; reverse: 5'-tttgccggcat-gtttcccaaggggagagttttgcaacc) and PCR product downstream of the F gene is obtained by the primers (forward: 5'-atgcatgccggcagatga; reverse: 5'-tgggtgaatgagagaatcagc). Then, the resulting plasmid is digested with SacI and SalI, and the fragment (4931 bp) containing the defective F gene is recovered and cloned into pUC18 to obtain pUC18/dFSS. PQ18/dFSS is digested with DraIII, the fragment is recovered and the DraIII fragment containing the F gene of pSeV18+ is replaced and ligated to obtain pSeV18/ΔF. A foreign gene can be inserted into the NsiI or NgoMIV site in the defective F gene of pUC18/dFSS. For this purpose, fragment containing the foreign gene can be amplified using primers tailed with NsiI and primers tailed with NgoMIV.

(2) Preparation of Helper Cells with Inducible Expression of SeV-F Protein

A Cre/loxP inducible expression plasmid expressing the Sendai virus F gene (SeV-F) is constructed as follows. The SeV-F gene is amplified by PCR and cloned into the unique SwaI site of the pCALNdLw plasmid (Arai et al., Journal of Virology, 1998, vol. 72, pp. 1115-1121). This plasmid is designed to express the gene product induced by the action of Cre DNA recombinase, thus obtaining pCALNdLw/F.

In order to obtain infectious viral particles from the genome of with defective F gene, an helper cell line expressing the SeV-F protein is established. LLC-MK2 cells, which are obtained from monkey kidney and commonly used for SeV propagation, can be used. LLC-MK2 cells are cultured with MEM with 10% heat inactivated fetal bovine serum (FBS), 50 units/ml penicillin G sodium and 50 mg/ml streptomycin at 37° C. and 5% CO2. Since the gene product of SeV-F is cytotoxic, the gene is cloned into pCALNdLw. In this plasmid, the expression of F gene can be induced by Cre DNA recombinase. The above pCALNdLw/F was transfected into LLC-MK2 cells according to standard methods by the calcium phosphate method (mammalian transfection kit (Stratagene)).

10 mg pCALNdLw/F is used to transfect LLC-MK2 cells cultured to 40% confluent in 10 cm plates to 40% confluent in a 10 cm plate, and the LLC-MK2 cells are cultured with 10 ml of 10% FBS at 37° C. and 5% CO2 for 24 hours. Then, the cells were stripped, suspended in 10 ml of medium, and plated onto five 10 cm plates, of which 5 ml of the cell suspension is placed on one plate, 2 ml for each of two plates, and 0.2 ml for each of two plates. The cells are cultured in 10 ml MEM containing 10% FBS and 1200 mg/ml of G418 (GIBCO-BRL) for 14 days, and the medium is changed every other days to select a stable transfectant. The cells resistant to G418 grown on the culture medium are recovered by a clone ring. The recovered cells of each colony are continuously cultured until they reach 100% confluent. Continue to culture the cells of each colony recovered until they reach 100% confluent in the 10 cm plates.

In order to induce expression of F protein, cells were cultured in a 6 cm plate to 100% confluent according to Saito et al. (Saito et al., Nucleic Acid Review, 1995, Vol. 23, pp. 3816-3821; Arai T. et al., Journal of Virology, 1998, Vol. 72, pp. 1115-1121), infection with AxcANCre adenovirus at moi=3.

(3) Reconstruction and Reproduction of SeV Virus with Defective F Gene

The pSeV18+/ΔF, into which a foreign gene has been inserted, is transfected into LLC-MK2 cells as follows. LLC-MK2 cells at $5 \times 10^6$ cells/plate are plated on a 100 mm plate and cultured for 24 hours, and then infected with recombinant vaccinia virus for 1 hour, wherein the recombinant vaccinia virus has been treated by psoralen and UV for 20 minutes (365 nm) (Furest T R et al., American Natural Science Process, 1986, vol. 83, pp. 8122-8126) under room temperature (moi=2-3; preferably moi=2). Radiation of the vaccinia virus by UV is performed by a UV stratakinker 2400 equipped by five 15-watt bulbs (catalog number 400676 (100V), Stratagene, La Jolla, Calif., USA). After the cells are washed for three times, the plasmids pSeV18+/DF-GFP, pGEM/NP, pEGM/P, and pGEM/L are suspended in OptiMEM (GIBCO) at 12 mg/plate, 4 mg/plate, 2 mg/plate and 4 mg/plate (Kato A. et al., Gene Cells, 1996, Vol. 1, pages 569-579), mixed with SuperFect transfection reagent (1 mg of DNA with 5 ml SuperFect (QIAGEN)), placed at room temperature for 10 minutes, then 3 ml of OptiMEM with 3% FBS is added, and then added into the cells. After incubation in the incubator for 3 hours, the cells are washed twice with serum-free MEM and incubated in MEM containing 40 mg/ml arabinoside (AraC, Sigma) and 7.5 mg/ml tryptone (GIBCO) for 70 hours. The cells are then collected and resuspended in OptiMEM at $10^7$ cells/ml. The cells are freezon-thawed for three times and then mixed with lipid transfection reagent DOSPER (Boehringer mannheim) ($10^6$ cells per 25 ml of DOSPER), allowed to stand at room temperature for 15 minutes, transfected into one of the selected F-helper cell line above-mentioned, such as LLC-MK2/F7 cells ($10^6$ cells/well, 12-well plate), cultured in serum-free MEM containing 40 mg/ml Arac and 7.5 mg/ml tryptone, and the supernatant is collected. Poxviruses that may be mixed can be removed by repeated dilution of the resulting supernatant and infection of LLC-MK2F7 cells.

In the preparation of the defective viral vector, two different viral vectors lacking different coating genes on the viral genomes can be transfected into the same cells. In this case, the respective defective coating proteins may be provided by expression of another vector, which may result in the formation of infectious viral particles and the turnover of the viral replication chain to replicate the viral vector. In other words, it is possible to simultaneously inoculate the combination of two or more viral vectors that are complementary in coating proteins, to produce a mixture of each of the coating missing viral vectors at low cost and on a large scale. Because these viruses lack the coating genes, their genomes are smaller than the virus that does not have deficiency in the coating genes, so they allow the insertion of longer foreign genes. In addition, these viruses, which are not infectious, are difficult to maintain a co-infection status after extracellular dilution, and are advantageous in environmental management because they are infertile.

In order to make the recovery of paramyxovirus truly pure, it can be refined. Purification can be carried out using known purification and separation methods, including filtration, centrifugation, column chromatography purification or a combination of these methods. "Truly pure" refers to the separation of a substance, such as a compound, polypeptide, viruse, and the like, is predominant in components of the sample that are present as substances. Typically, the truly pure ingredient present in the sample accounts for 50% or more, preferably 70% or more, more preferably 80% or more, more preferably 90% or more of the entire sample containing other components. This ratio may be calculated using a method known to those skilled in the art, such as a ratio of weight to weight (w/w). When calculating the ratio, it is necessary to remove the solvent, salts, added compounds and the like. A method for refining a paramyxovirus, specifically, such as an example using a cellulose sulfate or a crosslinked polysaccharide sulphate (Japanese Patent Application Laid-Open (JP-B): Sho 62-30752; JP-B Sho 62-33879; JP-B Sho 62-30753). And method to absorb it with sulfuric acid-containing polysaccharides and/or its degradation products (WO 97/32010), and the like.

The recovered SeV vector can be used as a live recombinant vaccine. In this context, a live vaccine is defined as a composition capable of amplifying a vector genome, expressing an antigenic protein, and obtaining an immunogen in a cell of an individual to be administered. As shown in the examples, vaccination of the SeV vector shows good effect in inducing immunity in monkeys, and does not exhibit significant clinical symptoms, and is therefore preferably used in a live vaccine. There are no restrictions on the subject for vaccination of such a live vaccine and may include all animals that can be infected by immunodeficiency virus, such as human, monkey, cat, dog, pig, horse, cow and the like. In addition, the use of the above-mentioned SeV vector that lacks the ability of propagation, a live vaccine with the vector does not propagate can be produced.

In addition, in the case where the expressed protein is incorporated into a SeV particle, the SeV vector can be used as an inactivated particle vaccine. Alternatively, in the case where the expressed protein is incorporated into a SeV particle, the expressed immunodeficient virus protein can be isolated and purified from the SeV vector and used as a vaccine. Because the SeV carrier contains a limited variety of proteins, it is much easier as compare with isolating the immunodeficiency virus protein expressed by an expression vector in cells from the whole cell lysate. Known isolation techniques can be used for the purification of proteins, for example, by immunoaffinity column chromatography using an antibody against the immunodeficiency virus protein. It can be desirable to use a purified protein as a vaccine, as compared to live and inactivated vaccines, to inhibit the frequency of fever and local reactions occurring after vaccination.

If desired, a vaccine containing a SeV vector may be combined with a desired pharmaceutically acceptable carrier or vehicle or may comprise a desired pharmaceutically acceptable carrier or vehicle. As used herein, "pharmaceutically acceptable carrier" is defined as those that can be administered with a vector but do not significantly inhibit the gene transformation of the vector. For example, the composition can be prepared by appropriately diluting the SeV vector with physiological saline, phosphate buffered saline (PBS) or the like. If the SeV vector is propagated in an egg, the composition may contain allantoic fluid. Likewise, a vaccine composition containing a SeV vector may contain a medium such as deionized water or a 5% aqueous dextran solution. It may further contain a vegetable oil, a suspending agent, a surfactant, a stabilizer, an antibiotic and the like. In addition, a preservative and other additives may be added. In order to improve the immunogenicity, an accelerant such as a cytokine, a cholera toxin, a typhoid toxin and the like can be added. In addition, alum, incomplete Freund's adjuvant, MF59 (oil emulsion), MTP-PE (muramyl tripeptide from mycobacterial cell wall) and QS-21 (available from soapbark tree *Quilaja saponaria*) can be combined with the vaccine. In a preferred embodiment, the SeV vector is formulated in combination with adjuvant levamisole as a vaccine composition.

Vaccination with the vaccine of the present application can prevent *Mycobacterium tuberculosis* infection and/or eliminate *Mycobacterium tuberculosis* after infection or inhibit the propagation of *Mycobacterium tuberculosis*. In addition, it can be used to prevent the onset of *tuberculosis*, or treat it after the onset. It can also be used for developing or assessing a preventive and/or therapeutic method in a *Mycobacterium tuberculosis* infection model.

The vaccine of the present application may be administered in a sufficient dose to transform an effective amount of the vector into the cells of a target tissue. As used herein, "an effective amount" is defined as a dose capable of introducing a gene into a target tissue so as to produce at least a portion of the desired immune response. Administration of an effective amount of a SeV vector containing a desired gene is capable of producing the gene product in the transfected cells. Preferably, administration of an effective amount of SeV containing the desired gene results in a significant expression level of the transfected gene in the tissue or blood to be administered. "A significant level" is defined as the expression of the gene by transfection of the SeV vector (the amount of transcription product or translation product) can be detected. However, the expression level of the transfected gene must be determined by in consideration of its effective level and toxicity level.

The expression level of a gene transfected into a cell can be determined by well-known test methods by those skilled in the art. The transcripts can be detected and quantified by Northern hybridization, RT-PCR, RNA protection test, and the like. In situ Northern blotting, RT-PCR and the like can also be performed. In order to detect the translation product, Western blotting, immunoprecipitation, RIA, ELISA, pull down tests using antibodies can be used. In order to easily detect the expression of a transfected gene, a tail tag can be attached to the protein to be expressed, or a reporter gene may be included in the vector. The reporter gene may be a gene encoding β-galactosidase, CAT, alkaline phosphatase, or GFP, but is not limited thereto.

A immune response can be tested by testing antibodies or immune cells. For example, a humoral immune response against *Mycobacterium tuberculosis* can be detected by various well-known test methods, such as testing the binding to various pathogenic proteins (ELISA, Western blotting and the like), complementary fixation, the ability of antibody-dependent cell-mediated cytotoxicity (ADCC), the ability of neutralizing infection or cell fusion and the like.

A cellular immune response can be tested for example, by testing CTL activity specific for the antigen, production of CTL, or production and activity of helper T cells, and the like. In addition, a cellular immune response can also be tested by testing activated T cells, such as CD8+ T cells, or other cytokines or chemokines produced by leukocytes. In addition, it can be tested by well-known lymphocyte proliferation tests, CTL tests, antigen-specific T cell tests and the like.

The dosage of the vector for administration may vary depending on the disease, the body weight, age, sex, symptoms of a patient, the purpose of administration, the form of vaccine and the method of administration, and the like, and can be appropriately determined by those skilled in the art. The dosage of the vector contained in the vaccine is preferably in the range of about $10^5$ pfu/ml to $10^{11}$ pfu/ml, more preferably about $10^7$ pfu/ml to $10^9$ pfu/ml, but most preferably at about $1 \times 10^8$ pfu/ml to $5 \times 10^8$ pfu/ml, which is administrated with a pharmaceutically acceptable carrier. The vaccine can be vaccinated intradermally, subcutaneously, intranasally, transbronchially, intramuscularly, intravenously, or orally. For example, mucosal immunity can be induced by vaccination in the vicinity of the upper respiratory tract, i.e., vaccination into the nasal mucosa and the upper respiratory tract. Therefore, it is very effective to inoculate the SeV vaccine through intranasal spray or the like in the trachea. It may also be administered intranasally, for example, by catheter-mediated administration. In addition, cells into which Sev has been introduced can be vaccinated as a vaccine. For example, cells obtained from individuals to be vaccinated are infected with SeV, and then vaccinated by in vivo administration.

In addition, it is not only for a single vaccination, but a sufficient immunity can also be induced by for example two or more vaccinations. In the case of a person, the interval among multiple vaccination is usually 2 to 4 weeks.

The vaccine of the present application containing SeV can be vaccinated for several times when using in multiple vaccinations, but a combination of the SeV vaccine and other vaccines is also preferred. As mentioned above, one of the disadvantages of virus vector-based vaccine regimens is it eventually induces a strong immune response against an antigen originated from the vector virus rather than the target antigen. This problem can be solved by using two or more different types of virus vectors for guiding and boosting respectively. Thus, as described above, it is also optional to use a vaccine based on a virus vector for boosting after guiding with a DNA based vaccine. In addition, re-vaccination of the same recombinant virus may not be sufficient to enhance the response specific to the antigen. Therefore, it is also effective to use a SeV vector for guiding and then boosting with a different virus vector or A DNA vaccine. Further, the use of a recombinant SeV vector expressing multiple antigens can improve the protection efficiency.

Therefore, in a case where different types of vaccines are used for guiding-boosting, the vaccine that is used in combination with a SeV vaccine is not limited and a desired vaccine can be used. Examples include recombinant subunit vaccines, live recombinant vaccines based on viruses or microorganisms other than SeV, BCG, polypeptide vaccines, DNA vaccines, and the like, but are not limited thereto. The subunit vaccine is defined as a vaccine that does not have all the antigens of *Mycobacterium tuberculosis* and contains only one or a multiple of selected protein antigens. Such a vaccine is at least partially isolated from other components of *Mycobacterium tuberculosis* or infected cells. A subunit vaccine can be prepared by at least partially purifying a *Mycobacterium tuberculosis* protein. In addition, a subunit vaccine can also be produced by recombination or by synthesis. Examples of microorganisms used as basic ingredients for live recombinant vaccines include poxvirus, adenovirus, typhoid virus, poliovirus, *mycobacterium*, influenza virus, and Semliki forest virus, and the like, but are not limited thereto. There is no restriction on the order of the vaccination of SeV vaccines and other vaccines. Other vaccines can be vaccinated after the vaccination of the SeV vaccine, on the contrary, the Sev vaccine can be vaccinated after the vaccination of other vaccines.

For example, after guiding with a DNA vaccine, a SeV vaccine is used for boosting. Such vaccination is a method comprising the steps of: (a) administering a DNA vaccine, and then (b) administering a paramyxovirus encoding a *Mycobacterium tuberculosis* protein. The DNA vaccine may utilize DNA encoding, for example, the genome of a *Mycobacterium tuberculosis*. The DNA vaccine can be administered, for example, by intramuscular administration and/or gene gun administration. After the DNA vaccine are vaccinated for several times, for example, a vaccine based on the SeV of the present application is vaccinated. The interval of vaccination is usually a few days to several weeks.

Animals that can be vaccinated may be all hosts with an immune system and which can be infected by *Mycobacterium tuberculosis*, including all mammals including humans, monkeys, mice, rats, rabbits, sheeps, pigs, cows, horses, birds and the like. The animals to be vaccinated by the vaccine of the present application are preferably primates. Examples of primates besides humans (nonhuman primates) that can be vaccinated by the vaccine of the present application include prosimians such as lemurs, loris and tarsier; monkeys such as platyrrhines and catarrhines; apes such as gibbon, orangutan, gorilla, chimpanzee, bonobo and so on. In particular, catarrhines, specifically macaques, including the Japanese macaque, cynomolgus monkey, rhesus monkey, bonnet monkey, pig-tailed macaque, brown stick tailed macaque, Assam monkey and so on. Vaccination on nonhuman primate are particularly useful for the development and evaluation of *tuberculosis* vaccines for clinical use on humans.

A vaccine containing a SeV vector encoding a protein of *Mycobacterium tuberculosis* can locally or systematically induce a immune response of the host. In particular, cells after introduction of the vector of the present application act as stimulating cells for a immune response specific for the antigen and induce a cellular immune response. The present application provides a method of inducing a cellular immune response specific to a *Mycobacterium tuberculosis* protein comprising the steps of: (a) introducing a Sendai virus vector encoding a *Mycobacterium tuberculosis* protein into an antigen presenting cell and (b) the process of contacting the antigen presenting cell with a T helper cell and a cytotoxic T cell. In this context, "contacting" a cell also includes allowing the cells to contact each other. In other words, this includes, for example, injecting the vector introduced cells into blood (capable of contacting T helper cells and cytotoxic T cells in the body); co-culturing the vector introduced cells with T helper cells and cytotoxic T cells in the same medium; and the like. In addition, "induction of a cellular immune response" specific to an antigen refers to induction of at least a portion of the cellular immune response. For example, stimulation of the CTLs specific to the antigen, increased frequency and activity of the CTL (e.g., cytotoxicity), and the like.

Antigen presenting cells refer to class I major histocompatibility complex (MHC) or class II MHC presented cells and have the ability to bind peptides of antigenic proteins to each molecule. Examples of antigen presenting cells are dendritic cells (DCs). Class I MHC molecules are molecules that bind an antigen peptide and present it to cytotoxic T cells (CD8+). Class II MHC molecules are molecules that bind an antigen peptide and present it to cytotoxic T cells (CD4+). T helper cells refer to a group of cells of T cell family that recognize an antigen presented by class II MHC molecules and integrate a series signalings of immune responses. Cytotoxic T cells also refer to a group of cells of T cell family that recognize an antigen presented by class I MHC molecules, kill cells such as cells infected with *Mycobacterium tuberculosis*, cancer cells, cells such as transplant cells, and the like (Xu M et al., Trends of Biotechnology 18 (4): 167-72, 2000).

For example, after a SeV vector encoding a *Mycobacterium tuberculosis* protein is transduced into peripheral blood mononuclear cells (PBMCs) and the like, through co-culturing with PBMCs in vitro, cellular immune responses such as the production of IFM-γ and proliferation of CTL specific to the *Mycobacterium tuberculosis* protein can be induced. In addition, in vivo administration can induce cellular immune responses specific to the antigen in the host.

The cellular immune response can be confirmed by measuring the amount of IFN-γ and measuring the frequency of CD8+ IFN-γ+ T cells. In addition, the activity of CTL can also be measured by measuring the lysis of the target cells using cells expressing the *Mycobacterium tuberculosis* as the target cells. Such target cells can be prepared by transduction of the above-mentioned SeV vectors. For example, a SeV expressing a *Mycobacterium tuberculosis* protein is introduced into the self Herpesvirus papio infinitely proliferating B lymphocyte line (BLC), and then incubated with a sample expected to contain CTLs. The degree of lysis of BLC can be measured using $^{51}$Cr release and the like as an indicator. In addition, the infinitely proliferating cell line H9 (from human T cells) and the like can also be exemplified.

The present application relates to the use of a SeV vector encoding a *Mycobacterium tuberculosis* protein or a cell into which the vector of the present application has been introduced for inducing or testing a cellular immune response specific to the *Mycobacterium tuberculosis* protein. In addition, the present application relates to a stimulated cell of a cellular immune response specific to a *Mycobacterium tuberculosis* protein including a cell into which a Sev vector encoding a *Mycobacterium tuberculosis* protein has been introduced. The present application relates to a target cell of a cellular immune response specific to a *Mycobacterium tuberculosis* protein including a cell into which a Sev vector encoding a *Mycobacterium tuberculosis* protein has been introduced. In addition, the present application also relates to the use of SeV vector encoding a *Mycobacterium tuberculosis* protein in the above stimulated cell or target cell.

The Sev vector encoded *Mycobacterium tuberculosis* protein is not limited. As shown above, they may be *Mycobacterium tuberculosis* structural proteins, regulatory proteins, modified proteins, and the like. Examples of structural proteins include Ag85A, Ag85B, and the like. For example, use of SeV encoding Ag85A protein of *Mycobacterium tuberculosis* can induce a cellular immune response specific to Ag85A.

EXAMPLES

The present application will be illustrated below in detail by examples, but the present application is not limited by the examples. The contents of the references through the present specification are incorporated herein by reference.

Example 1

Isolation, Amplification and Construction of Ag85AB Chimeric Gene

An Ag85A gene was amplified by PCR from the genome of *Mycobacterium tuberculosis*, wherein primers used are a upstream primer of a P1 sequence for 5' end of the gene and a downstream primer of a P2 sequence for 3' end of the gene (5'-ATA GCTAGC ATG GTT TCC CGG CCG GGC TTG C-3' and 5'-TAA GGATCC CTA GGC GCC CTG GGG CGC-3'). The resulting PCR product was ligated into a pVAX1 vector after double digestion by NheI/BamHI. Then, a Kpn I restriction site at positions 245-250 or a Acc I restriction site at positions 430-435, to which a foreign DNA fragment can be inserted in the Ag85A gene, was selected, and the Ag85A gene was digested with the endonuclease Kpn I or Acc I followed by dephosphorylation with alkaline phosphatase. Next, a DNA fragment encoding the amino acid sequence of positions 125 to 282 of the Ag85B protein was amplified from the genome of *Mycobacterium tuberculosis* by a polymerase chain reaction using a primer pair with a endonuclease Kpn I or Acc I recogization sequence. The inventor designed a upstream primer of a P3 sequence for 5' end of the sequence and a downstream primer of a P4 sequence for 3' end of the sequence (5'-CACATCACGA-TACCG GTCTAC TCGATGGCCGGCTCGTC-3' and 5'-CACATGCGAATACCG GTAGAC TAACGAACTCT-GCAGGTC-3'), both of which have an Acc I restriction site (GTCTAC); or a upstream primer of a P5 sequence and a downstream primer of a P6 sequence (5'-CACATCACGA-TACCG GGTACC TCGATGGCCGGCTCGTC-3' and 5'-CACATGCGAATACCG GGTACC TAACGAACTCT-GCAGGTC-3'), both of which have a Kpn I restriction site (GGTACC). The Ag85A gene was digested with the endonuclease Kpn I or Acc I, respectively, and dephosphorylated with alkaline phosphatase.

Then, the digested Ag85A gene was ligated to a Ag85B fragment with a T4 DNA ligase, and the resulting plasmid was transformed into *E. coli* prior to selection of a colony which grows up from a kanamycin resistance culture plate. A single colony was picked up into a test tube for culture and then the plasmids were extracted for identification by electrophoresis. Then the plasmids were enzymically cleaved and identified by electrophoresis. Those with correct sequence by primary selection were confirmed by sequencing, and the construction of a recombinant Ag85AB chimeric gene was successful.

Example 2

Construction of a SeV85AB Recombinant Sendai Virus Vector

A SeV vector with a F gene deletion (SEQ ID No: 9) was constructed and provided by DNAVEC Corporation, Japan (H. Li. et. al., Journal of Virology, 2000, vol. 74: pp. 6564-6569). A recombinant SeV vector vaccine expressing the Ag85AB protein of *Mycobacterium tuberculosis*, SeV85AB (hereafter, abbreviated as SeV85AB) was constructed using the vector. In particular, previous experiments have demonstrated that knock-out of the F gene of the SeV fusion protein by recombinant technology did not influence the replication and gene expression of the vector virus in cultured cells, and the infected cells would not produce and release infective viral particles. Thus, knock-out of the F gene enhances the safety of the vector while ensure the efficacy of virus infection and replication. The inventor have described an attenuated SeV genomic cDNA plasmid pSeV (+)18/dF with a deletion of the full length of the F gene, as described in H. Li. et. al. as above.

A gene fragment encoding the Ag85AB (Acc I as a chimeric site) was prepared by PCR amplication, and cloned into pSeV(+)18/dF to produce pSeV(+)18 dF/Ag85AB. The sequences of P7 and P8 used in PCR are 5'-ATT GCG GCC GCG ACA TGG TTT CCC GGC CGG GCT TG-3'; 5'-ATT GAT GAA CTT TCA CCC TAA GTT TTT CTT ACT ACG GCT AGG CGC CCT GGG GCG GGG GCC CGG TGT TGG GCG TG-3'. First, we isolated (in the Example 1) and used the above primers to amplify the immunodominant gene Ag85AB of *Mycobacterium tuberculosis*. Then, the gene was inserted into pSeV(+)18/dF vector via a NotI site upstream of the N terminal encoding region (FIG. 1). Under the action of T7 RNA polymerase, this plasmid, pSeV(+)18 dF/Ag85AB, can produce the full length of anti-genomic RNA of SeV85AB. Next, the plasmid pSeV(+)18 dF/Ag85AB was transfected into a LLC-MK cell and a recombinant SeV, i.e. SeV85AB was recovered (Kato, A. et. al., Gene Cells, 1996, vol. 1: pp. 569-579). In particular, LLC-MK2 cells were infected with recombinant vaccinia virus (VV) expressing T7 RNA polymerase, vTF7-3 (Fuerst, T. R. et. al., PNAS, 1986, vol. 83: 8122-8126), and then the cell was co-transfected with pSeV(+)18 dF/Ag85AB and pGEM-N, pGEM-P, and pGEM-L (Garcin, D. et. al., EMBO J., 1995, vol. 14: 6087-6094). The cells were incubated in a cell incubator for 3 hours, and then the supernatant of the cell culture was removed. The cells were washed twice with DMEM medium without serum, and continued to be cultured in DMEM containing 40 mg/mg cytarabine (AraC, Sigma) and 7.5 mg/ml tryptone (GIBCO) for 70 hours. Then, the cells were collected, and resuspended in a medium at a ratio of $10^7$ cells/ml. The cells were repeatedly frozen and thawed for 3 times, then mixed with a lipofectamine reagent DOSPER (Boehringer mannheim) ($10^6$ cells per 25 ml DOSPER), and placed at RT for 15 min. The vector was transfected into a helper cell line expressing F gene, such as LLC-MK2/F7 cell ($10^6$ cells/well, 12-well plate), and the cell line was continued cultured in DMEM medium containing 40 mg/ml Arac and 7.5 mg/ml tryptone without serum and the supernatant was collected.

We prepared blank SeV as a control for SeV85AB using the same method. LLC-MK2 cells and an anti-SeV antibody were used to perform immunostain to screen for and identify a SeV vector vaccine. The determination of titer (CIU [cell infection unit]/ml) was described in Kiyotani, K. et. al., Virology, 1990, 177: pp. 65-74).

The SeV85AB recombinant Sendai virus vector obtained by this example was deposited at China Center for Type CultureCollection (CCTCC, address: Luo JiaShan, Wuchang district of Wu Han city, Post Code: 430072) on Apr. 19, 2015 under the accession number of CCTCC V201518 (Taxonomy: Paramyxoviridae/Paramyxovirus).

Example 3

Identification of the SeV85AB Recombinant Virus Expressing Ag85AB

Figure 2:
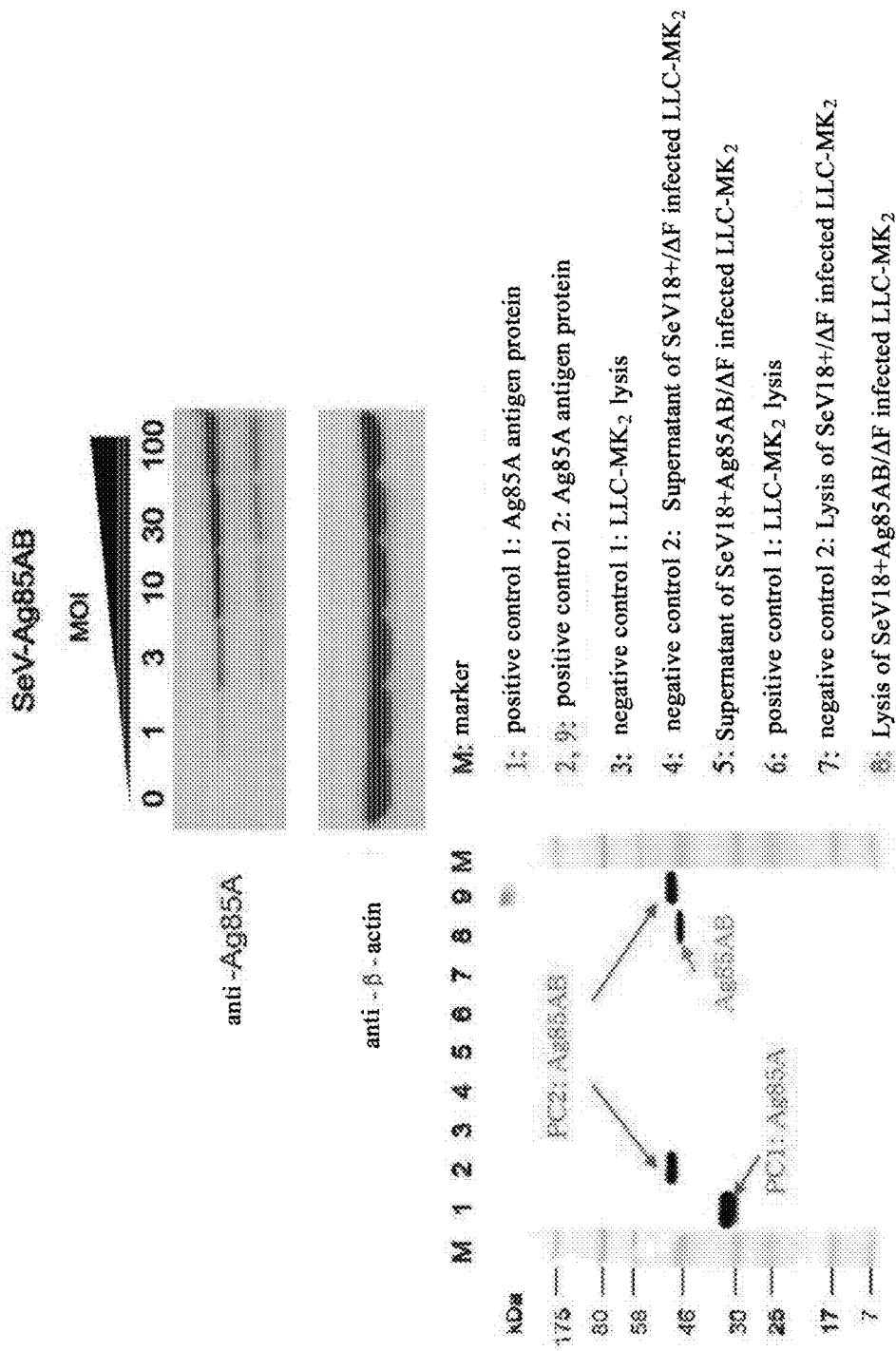
FIG. 2 shows results of identification of SeV85AB expression of the constructed pSeV85AB plasmid, in which after LLC-MK2 cells were infected with SeV85AB at different MOI, Western Blot analysis is performed on the cell lysate using a mouse anti-Ag85A antibody and a goat anti-mouse immunoglobulin G (IgG) conjugated with fluorescein.

Cells were infected with SeV85AB, and analyzed for the proteins expressed thereof. In particular, LLC-MK2 cells were cultured overnight at a density of $4\times10^5$ cells per well in a 6-well plate, and then the cells were infected with SeV or SeV85AB with a multiplicity of infection (m.o.i.) at 1, 3, 10, 30, and 100. Two day later, the cells were recovered, and then lysed with 1× SDS sample buffer. After heat treated at 100° C., 10 µl of the cell lysate was added into each lane for a SDS-PAGE electrophoresis. Anti-Ag85A mouse monoclonal antibody was used as primary antibody, and a fluorescein-conjugated goat anti-mouse immunoglubin G(IgG) was used as secondary antibody to conduct Western Blot analysis. The data confirmed that SeV85AB infected LLC-MK2 cells expresses Ag85AB, whereas the SeV blank vector showed negative results (FIG. 2).

Example 4

Nasal Immunization with SeV85AB in Mice can Induce Antigen Specific T Cell Immune Response Specific pathogen free (SPF) female BALB/c mice (6-8 weeks age) were purchased from Shanghai SLAC Laboratory Animal Co., Ltd. (Shanghai, China). The mice were used to verify whether nasal immunization with SeV85AB can induce Ag85AB specific immune response. The mice were immunized intranasally with SeV85AB at $2\times10^6$ CIU/animal and $10^7$ CIU/animal (20 ul in PBS), and mice inoculated with a blank virus (which is a SeV vector not expressing a *tuberculosis* antigen) and PBS were used as a control. Two weeks after immunization, the mice were sacrificed, and lungs (including the trachea tissue) and spleens were remove form the mice.

Single cell suspensions of lung lymphocytes and splenocytes were prepared as follows. Spleens were disrupted mechanically, and single splenocytes were filtered out by passing through a mesh gauze. Red blood cells (RBC) were lyzed with a RBC lysation buffer (BD Biosciences). Meanwhile, lungs were removed aseptically and cutted into fragments with scissors, and then inoculated with 1 mg/ml Collagenase IV (Invitrogen) and 10 U DNase I (Thermo) in 10 ml R10 medium (a RPMI-1640 medium containing 10% FBS [fetal bovine serum] and 1% penicillin plus streptomycin) at 37° C. for 30 minutes. For dissociating the tissues into single cells, the collagenase treated lung fragments were filtered gently with a 70 µm cell filter (Fisher Scientific), and crushed with a plunger of a syringe. Then, the cell suspension was centrifugated, and subjected to RBC lysis. After being washed, single lung lymphocytes were resuspended in a R10 medium and counted for further analysis.

The numbers of CD4+ T and CD8+ T cells specifically secreting IFN-γ upon the stimulation of an Ag85AB polypeptide or protein (5 µg/ml) and PPD (tuberculin pure protein derivative, available from Statens Serum Institute, SSI, 10 µg/ml) were detected using an ELISPOT method. Information regarding the Ag85AB polypeptide or protein for stimulation was as follows: Ag85A-CD4 peptide (*Mycobacterium tuberculosis* protein Ag85A (LTSELPGWLQAN-RHVKPTGS, class II MHC specific peptide), FUNAKOSHI cat. No. [ANA]62425), Ag85A-CD8 peptide (*Mycobacterium tuberculosis* protein Ag85A-CD8 (MPVGGQSST, class I MHC specific peptide), FUNAKOSHI cat. No. [ASI] 62424), Ag85B-CD4 peptide (*Mycobacterium tuberculosis* protein Ag85B(240-254) (FQDAYNAAGGHNAVF, capable to elicit CD4+ T helper cells (Th)1), Sigma-Aldrich, cat. No. [ANA]65391), rAg85A (recombinant Ag85A protein, in-house purification, a sequence as shown in SEQ ID No: 10).

Figure 3:
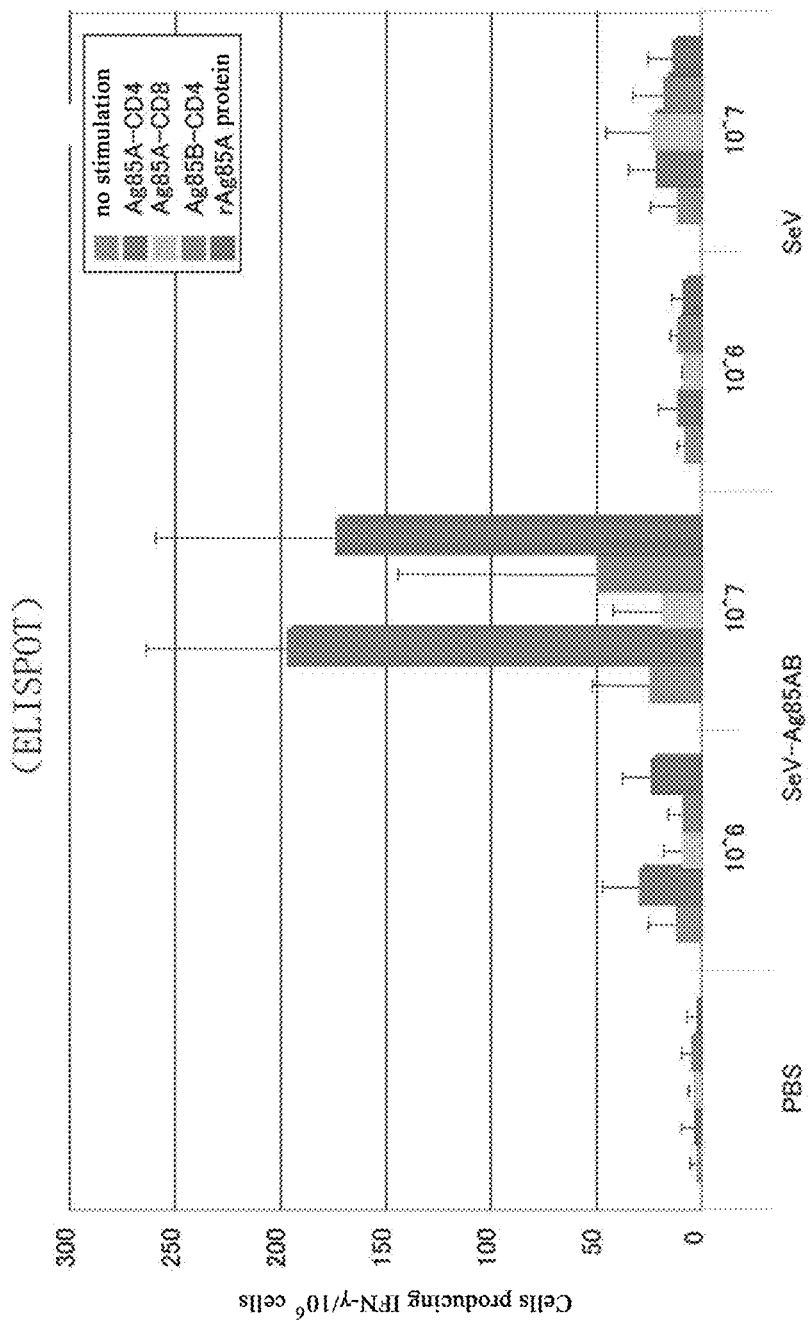
FIGS. 3 and 4 are determination of the levels of IFN-γ secreted by in vitro stimulated T lymphocytes from lung or spleen of the mice respectively by ELISPOT after vaccination with SeV85AB intranasally.
Figure 4:
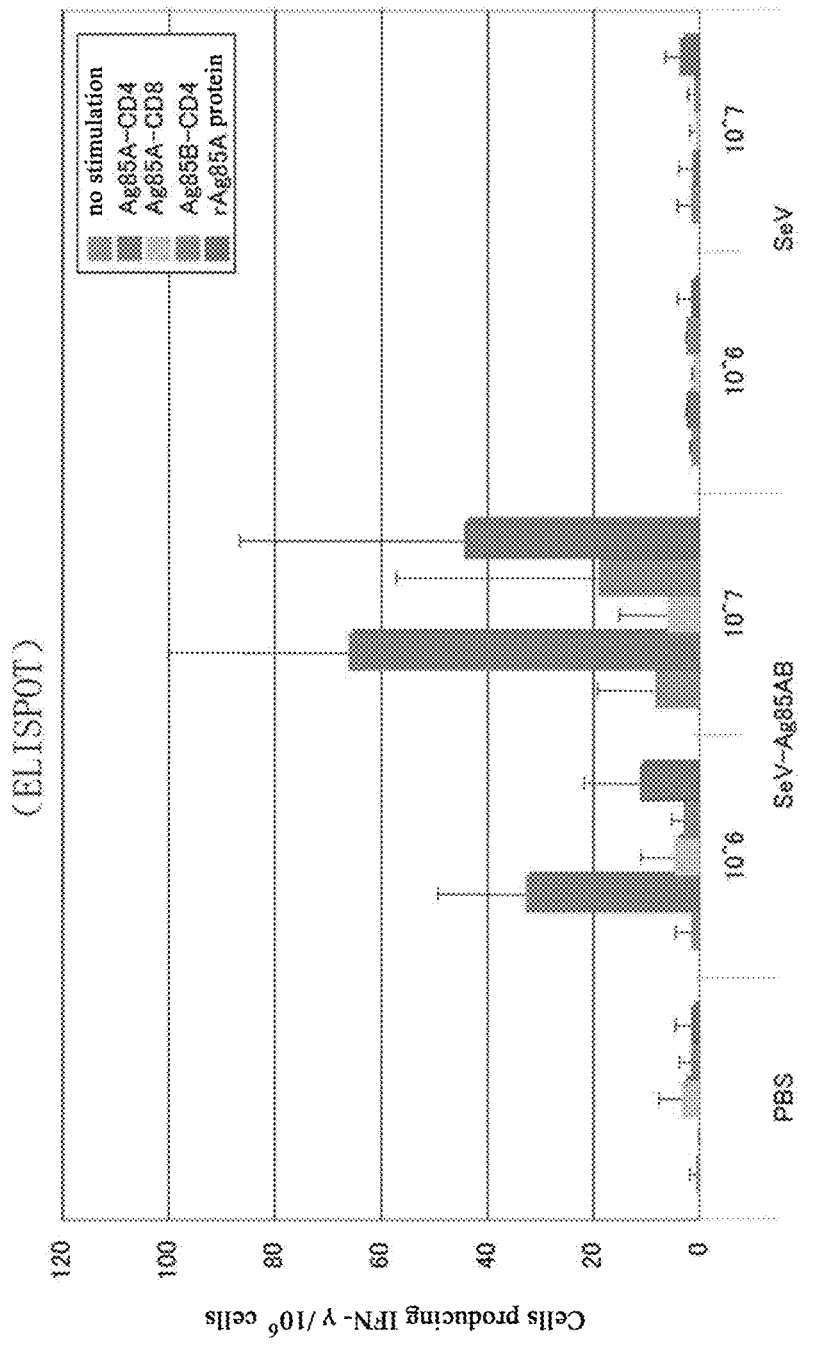
Figure 5:
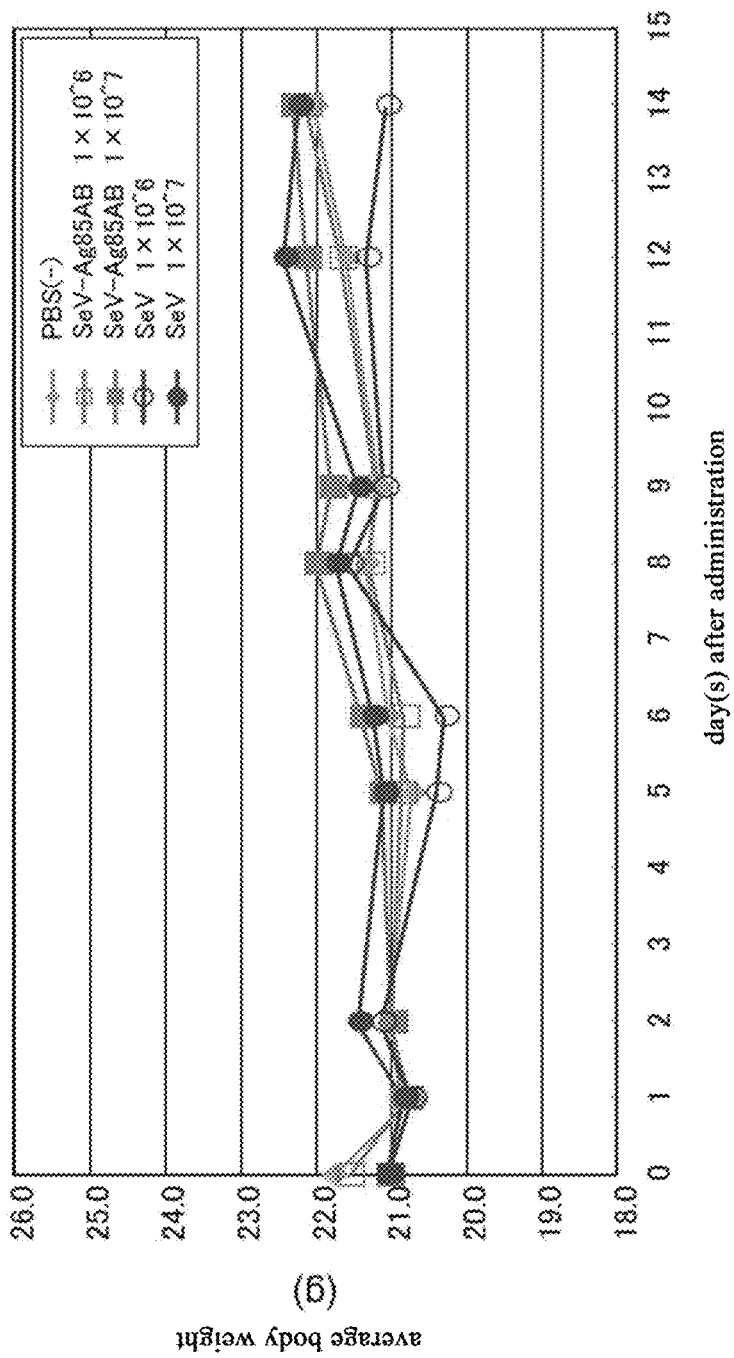
FIG. 5 shows changes in body weight of mice after administration of PBS, two doses of SeV85AB and two doses of SeV blank vector. The results show that intranasal immunization with SeV85AB did not cause abnormal changes in body weight of mice.
Figure 6:
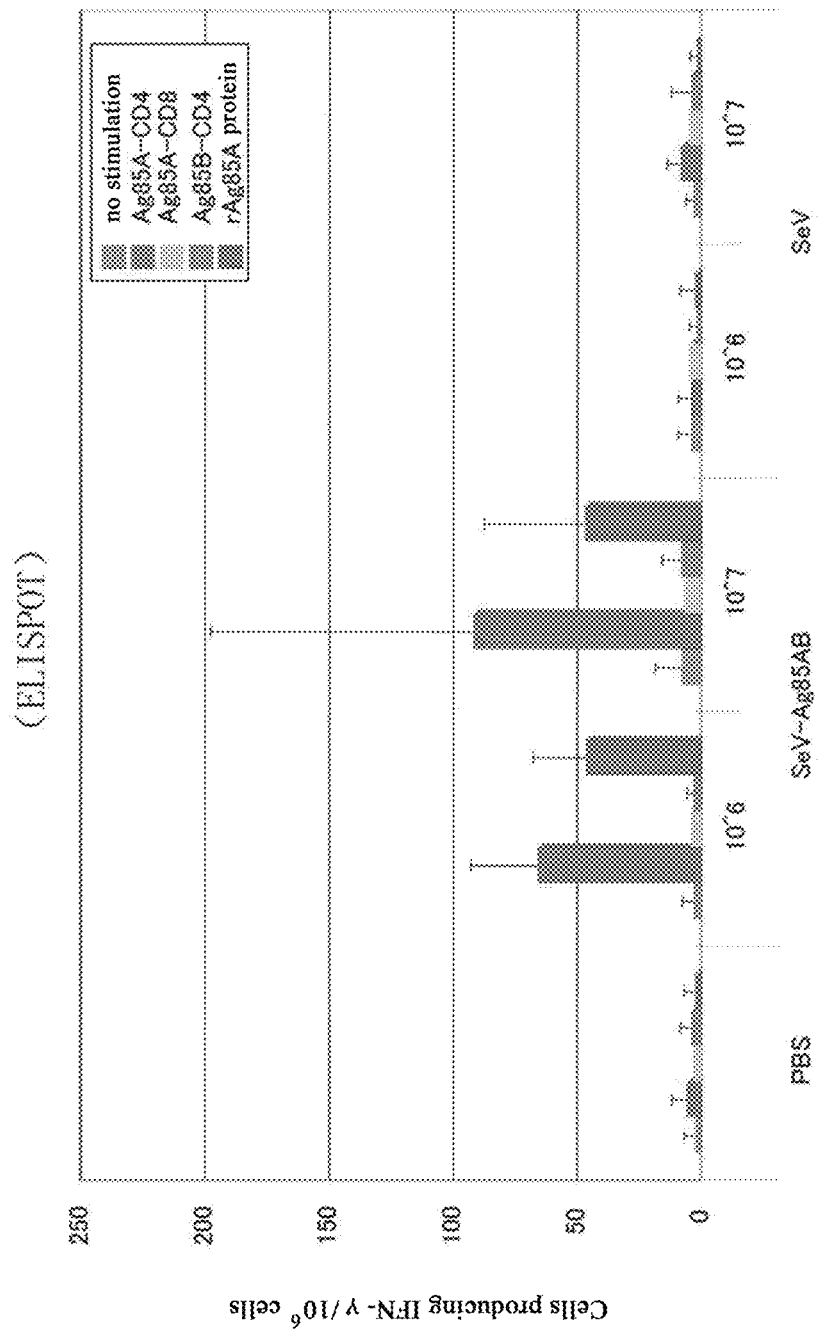
FIGS. 6 and 7 are determination of the levels of IFN-γ secreted by in vitro stimulated T lymphocytes from lung or spleen of the mice respectively by ELISPOT after vaccination with SeV85AB intramuscularly.
Figure 7:
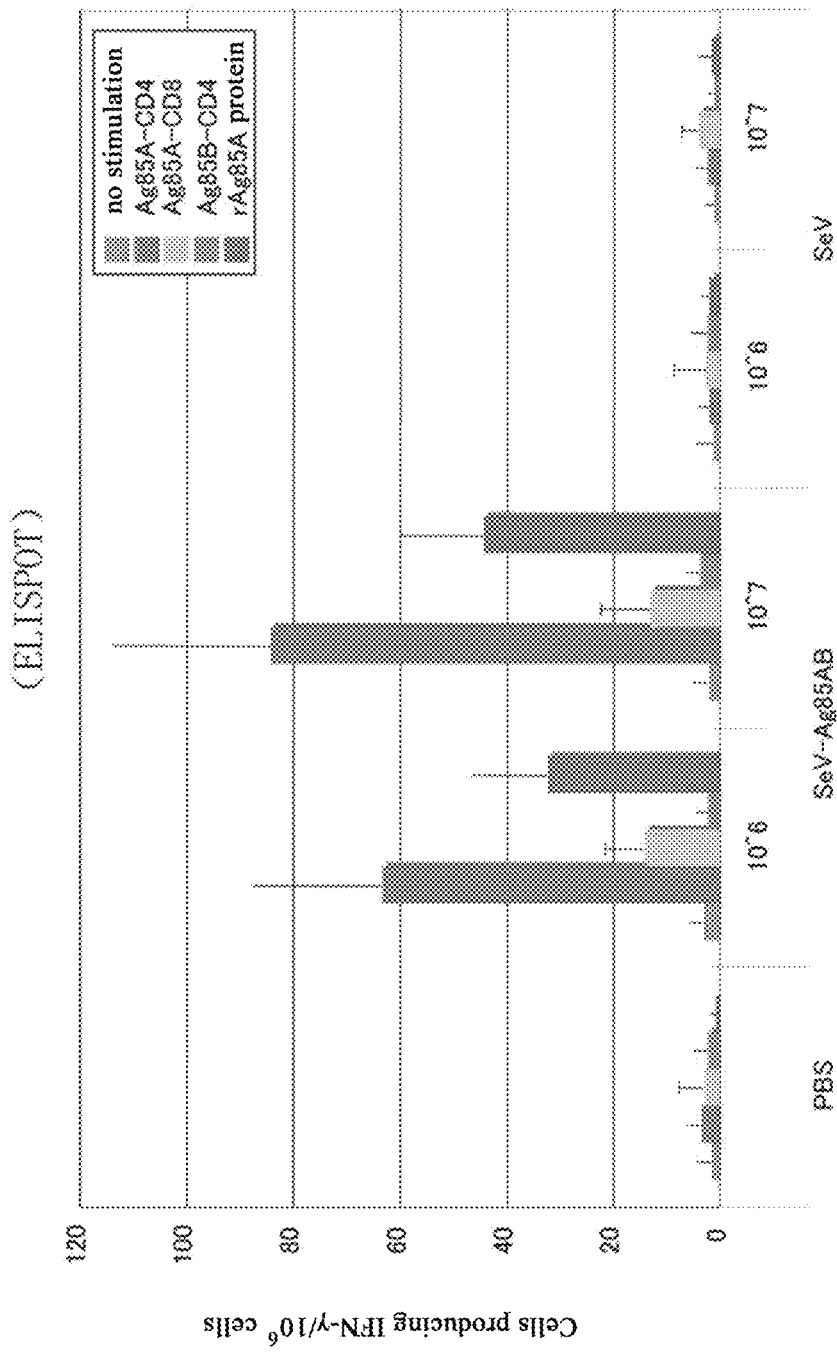
Figure 8:
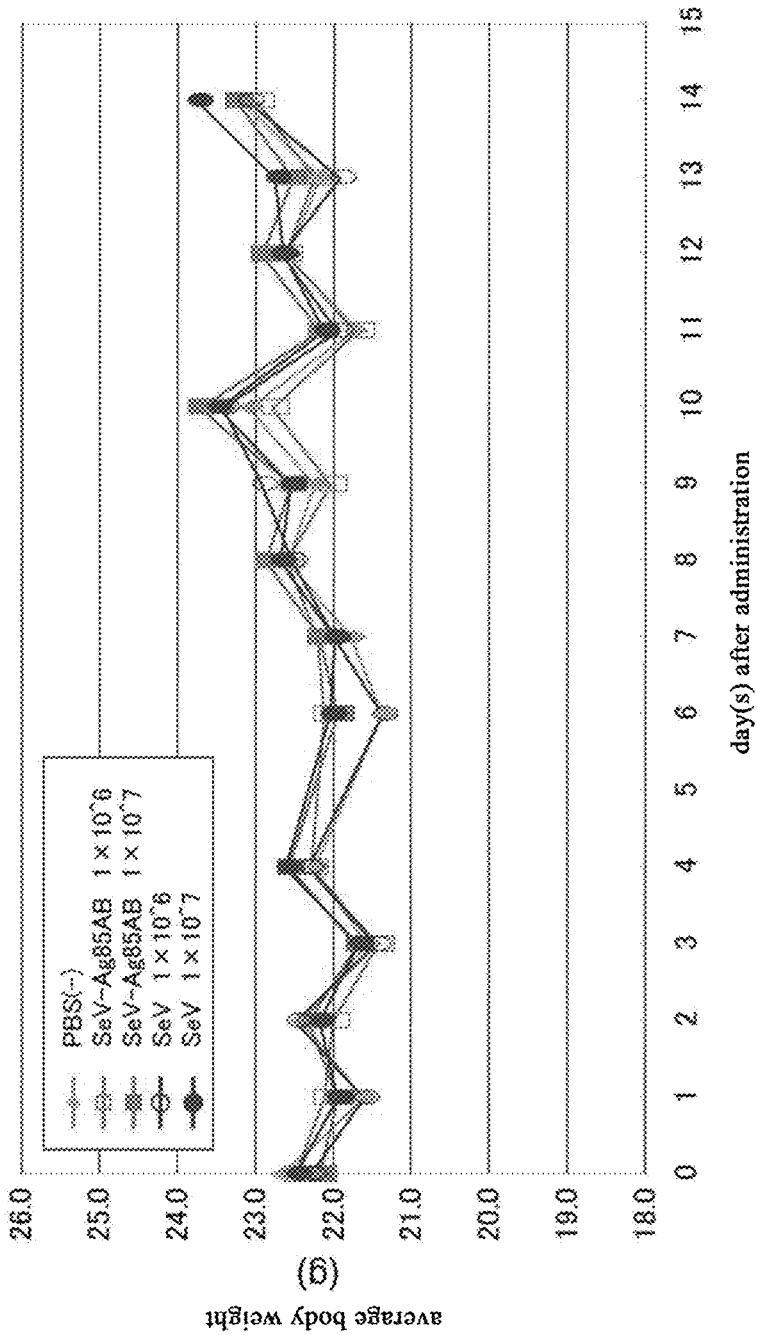
FIG. 8 shows changes in body weight of mice after administration of PBS, two doses of SeV85AB and two doses of SeV blank vector. The results show that intramuscular immunization with SeV85AB did not cause abnormal changes in body weight of mice.

The data demonstrated that nasal immunization with SeV85AB can induce a strong antigen specific T cell immune response in lungs and spleens of the mice, whereas the blank vector and PBS which serve as a negative control did not induce corresponding immune responses. FIG. 3 is the results of detecting the lung lymphocytes. The results confirmed that stimulation with Ag85A-CD4 polypeptide, rAg85A protein and PPD can induce IFN-γ secretion of the lymphocytes of the immunized mice. The same results were obtained for spleens as well (FIG. 4). Regarding the dosage, $10^7$ CIU high-dosage immunization group showed better effect in inducing antigen specific T cell than that in 2×10⁶ CIU low-dosage immunization group (FIGS. 3-4). It can be seen from these results that the SeV85AB vaccine can induce local (lungs) and systemic (spleens) immune response to the *tuberculosis* antigen Ag85A after nasal immunization, as compared to the blank Sev vector and PBS. Furthermore, toxic reactions such as a significant loss of body weight were not observed for both the $10^7$ CIU immunization group and $2\times10^6$ CIU immunization group, whether expressing the *tuberculosis* antigen or not (FIG. 5).

Example 5

Intramuscular Immunization of Mice with SeV85AB can Induce Antigen Specific T Cell Immune Response Specific pathogen free (SPF) female BALB/c mice (6-8 weeks age) were purchased from Shanghai SLAC Laboratory Animal Co., Ltd. (Shanghai, China). The mice were used to test whether vaccination by intramuscular injection of SeV85AB can induce Ag85AB specific immune response. The mice were vaccinated intramuscularly with SeV85AB at $2\times10^6$ CIU/animal and $10^7$ CIU/animal (20 ul in PBS), whereas mice vaccinated with a blank virus (which is a SeV vector not expressing a *tuberculosis* antigen) and PBS were used as controls. Two weeks after immunization, the mice were sacrificed, and lungs (including the trachea tissue) and spleens were remove form the mice. Single cell suspensions of lung lymphocytes and splenocytes were prepared as described in Example 4.

The numbers of CD4+ T and CD8+ T cells specifically secreting IFN-γ upon the stimulation of an Ag85AB polypeptide or protein (5 μg/ml) and PPD (tuberculin pure protein derivative, available from Statens Serum Institute, SSI, 10 μg/ml) were tested using an ELISPOT method. Information regarding the Ag85AB polypeptide or protein for stimulation was as follows: Ag85A-CD4 peptide (*Mycobacterium tuberculosis* protein Ag85A (LTSELPGWLQANRHVKPTGS, class II MHC specific peptide), FUNAKOSHI cat. No. [ANA]62425), Ag85A-CD8 peptide (*Mycobacterium tuberculosis* protein Ag85A-CD8 (MPVGGQSST, class I MHC specific peptide), FUNAKOSHI cat. No. [ASI] 62424), Ag85B-CD4 peptide (*Mycobacterium tuberculosis* protein Ag85B(240-254) (FQDAYNAAGGHNAVF, capable to elicit CD4+ T helper cells (Th)1), Sigma-Aldrich, cat. No. [ANA]65391), rAg85A (recombinant Ag85A protein, in-house purification, a sequence as shown in SEQ ID No: 10).

The data shown that intramuscular immunization with SeV85AB can induce strong antigen specific T cell immune response in lungs and spleens of the mice, whereas the blank vector and PBS which serve as a negative controls did not induce corresponding immune responses. FIG. 6 shows the testing results of lung lymphocytes. The results confirmed that stimulation with the Ag85A-CD4 polypeptide, rAg85A protein and PPD can induce specific IFN-γ secretion of the lung lymphocytes. The same results were obtained for spleens as well (FIG. 7). From these results, it can be seen that SeV85AB vaccine can induce local (lungs) and systemic (spleens) immune response to the *tuberculosis* antigen Ag85A after intramuscular immunization, as compared to the blank Sev vector and PBS. Furthermore, toxic reactions such as a marked loss of body weight were not observed for both the $10^7$ CIU immunization group and $2\times10^6$ CIU immunization group, whether expressing the *tuberculosis* antigen or not (FIG. 8).

Example 6

Boosting Effect of Combination Immunization with SeV85AB and BCG Vacceines as Polyvalent Vaccines Specific pathogen free (SPF) female BALB/c mice (6-8 weeks age) were purchased from Shanghai SLAC Laboratory Animal Co., Ltd. (Shanghai, China), as describe above. The mice were used to evaluate the boosting effects of SeV85AB for BCG vaccine (BCG Danish strain, available from Shanghai Insititue of biologica products Co., Ltd., China National biotec Group Company Limited). The mice were divided into 8 groups randomly, and each group was subjected to a primary immunization with BCG and PBS which servers as a control. 8 weeks later, a boosting immunization was performed with PBS, BCG, SeV/control or SeV85AB to test whether a *tuberculosis* antigen specific cell immunity can be induced. Details of the experiment design are as follows:

| Group | priming | boosting | |
|---|---|---|---|
| 1 | PBS | 8 weeks later | PBS |
| 2 | PBS | 8 weeks later | BCG |
| 3 | PBS | 8 weeks later | SeV/control |
| 4 | PBS | 8 weeks later | SeV85AB |
| 5 | BCG | 8 weeks later | PBS |
| 6 | BCG | 8 weeks later | BCG |
| 7 | BCG | 8 weeks later | SeV/control |
| 8 | BCG | 8 weeks later | SeV85AB |

When priming with PBS, 100 μl was injected into a inguinal subcutaneous site of right hindlimb (50 μl each for inner side and outer side). When priming with BCG, $10^6$ colony formation unit (CFU)/100 μl/animal was injected into a inguinal subcutaneous site of right hindlimb (50 μl each for inner side and outer side).

8 weeks after the priming, a boosting immunization was performed in a manner of nasal immunization. The dose for PBS boosting immunization was 20 μl/animal, and was $10^6$ CFU/20 μl/animal for BCG, $10^7$ CIU/20 μl/animal for the blank SeV vector, $10^7$ CIU/20 μl/animal for SeV85AB vector. Two weeks after the boosting immunization, the lungs (including the trachea tissue) and spleens were removed from the mice and single cell suspensions of lung lymphocytes and splenocytes were prepared as described in Example 4.

The numbers of CD4+ T and CD8+ T cells specifically secreting IFN-γ upon the stimulation of an Ag85AB polypeptide or protein (5 μg/ml) and PPD (tuberculin pure protein derivative, available from Statens Serum Institute, SSI, 10 μg/ml) were tested using an ELISPOT method. Information regarding the Ag85AB polypeptide or protein for stimulation was as follows: Ag85A-CD4 peptide (*Mycobacterium tuberculosis* protein Ag85A (LTSELPGWLQANRHVKPTGS, class II MHC specific peptide), FUNAKOSHI cat. No. [ANA]62425), Ag85A-CD8 peptide (*Mycobacterium tuberculosis* protein Ag85A-CD8 (MPVGGQSST, class I MHC specific peptide), FUNAKOSHI cat. No. [ASI] 62424), Ag85B-CD4 peptide (*Mycobacterium tuberculosis* protein Ag85B(240-254) (FQDAYNAAGGHNAVF, capable to elicit CD4+ T helper cells (Th)1), Sigma-Aldrich, cat. No. [ANA]65391), rAg85A (recombinant Ag85A protein, in-house purification, a sequence as shown in SEQ ID No: 10).

Figure 9:
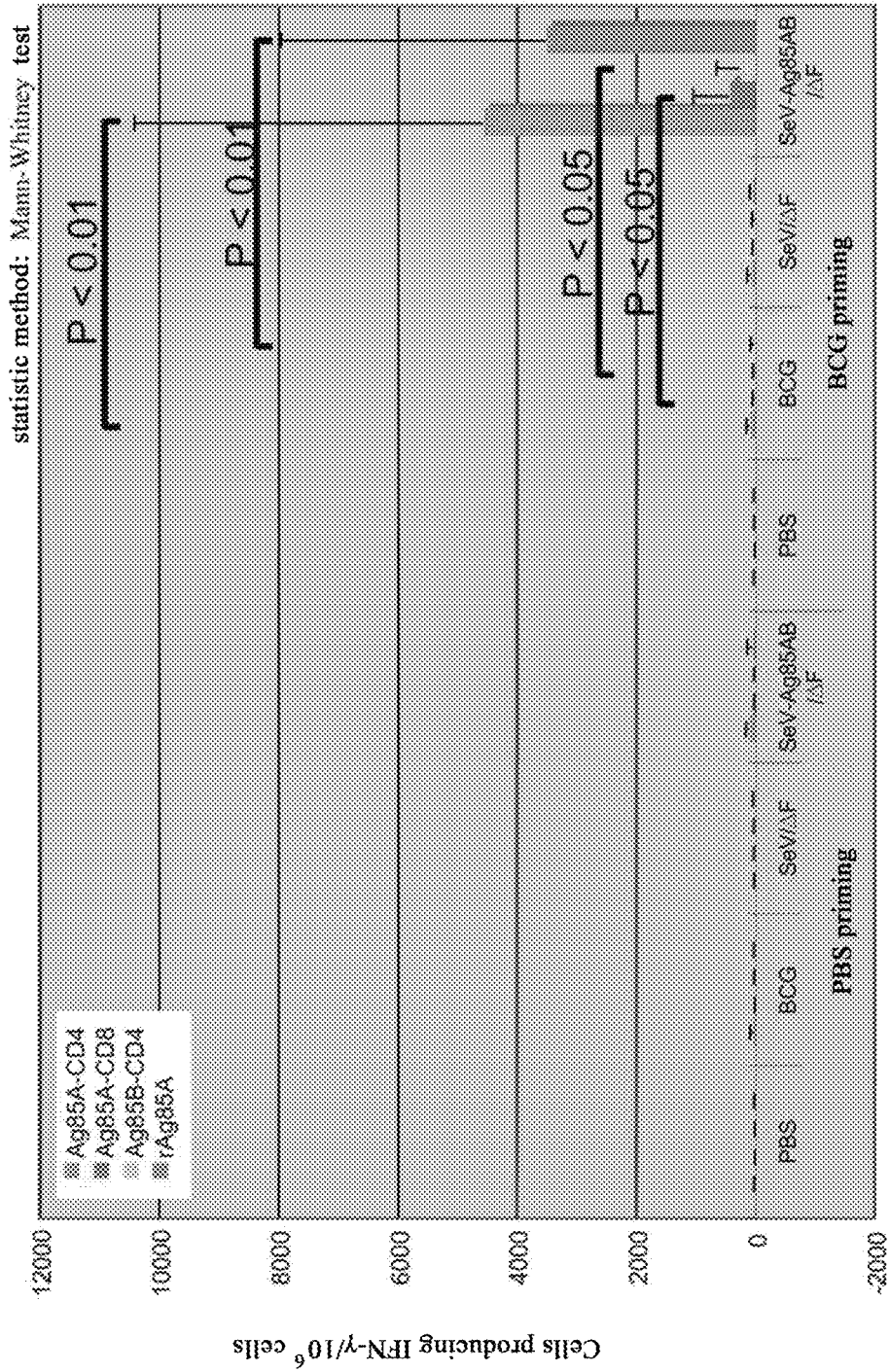
FIGS. 9 and 10 show the results of T-cell response in lung and spleen cells of mice obtained using the eight priming-boosting schemes as described in Example 6.
Figure 10:
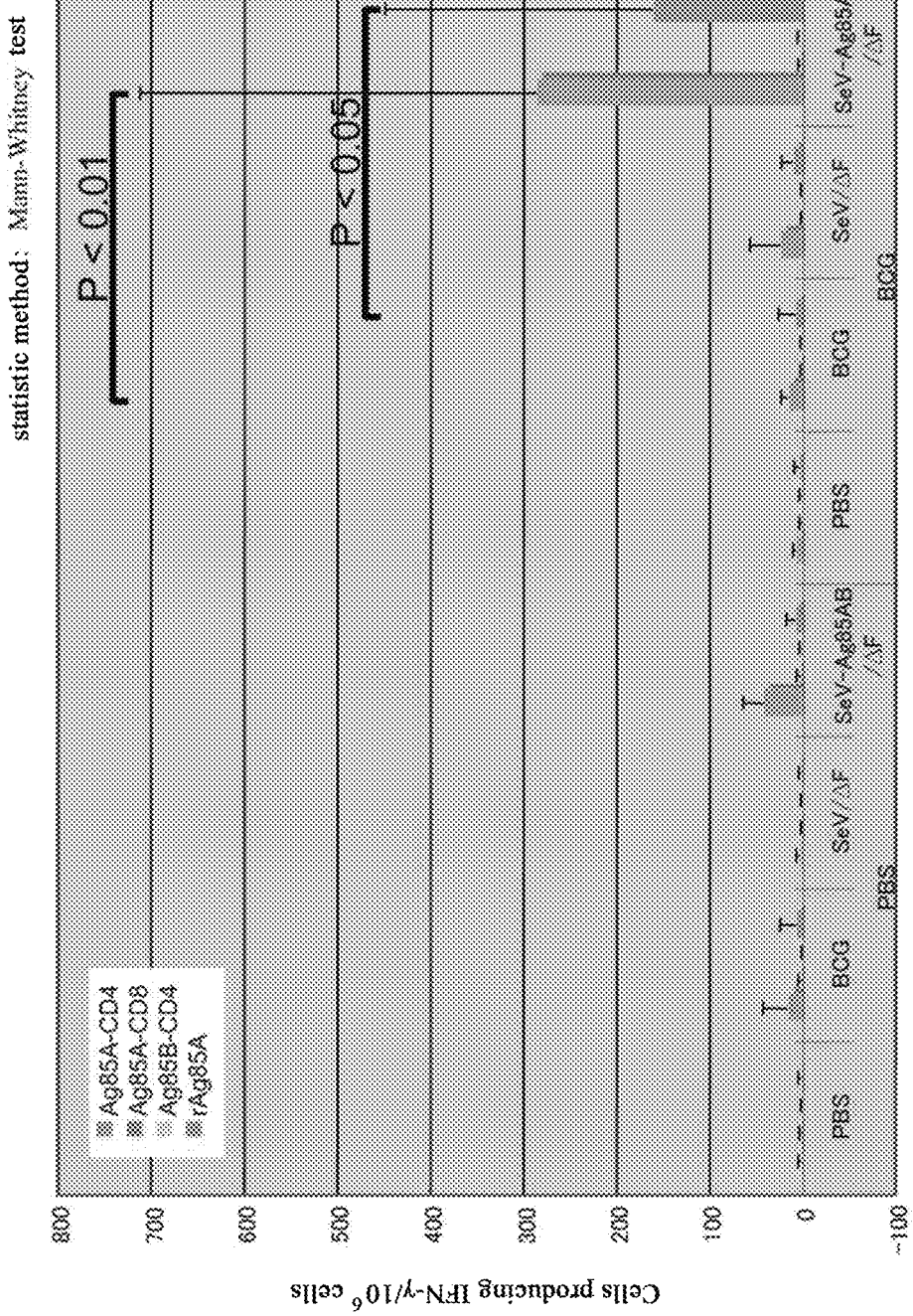
Figure 11:
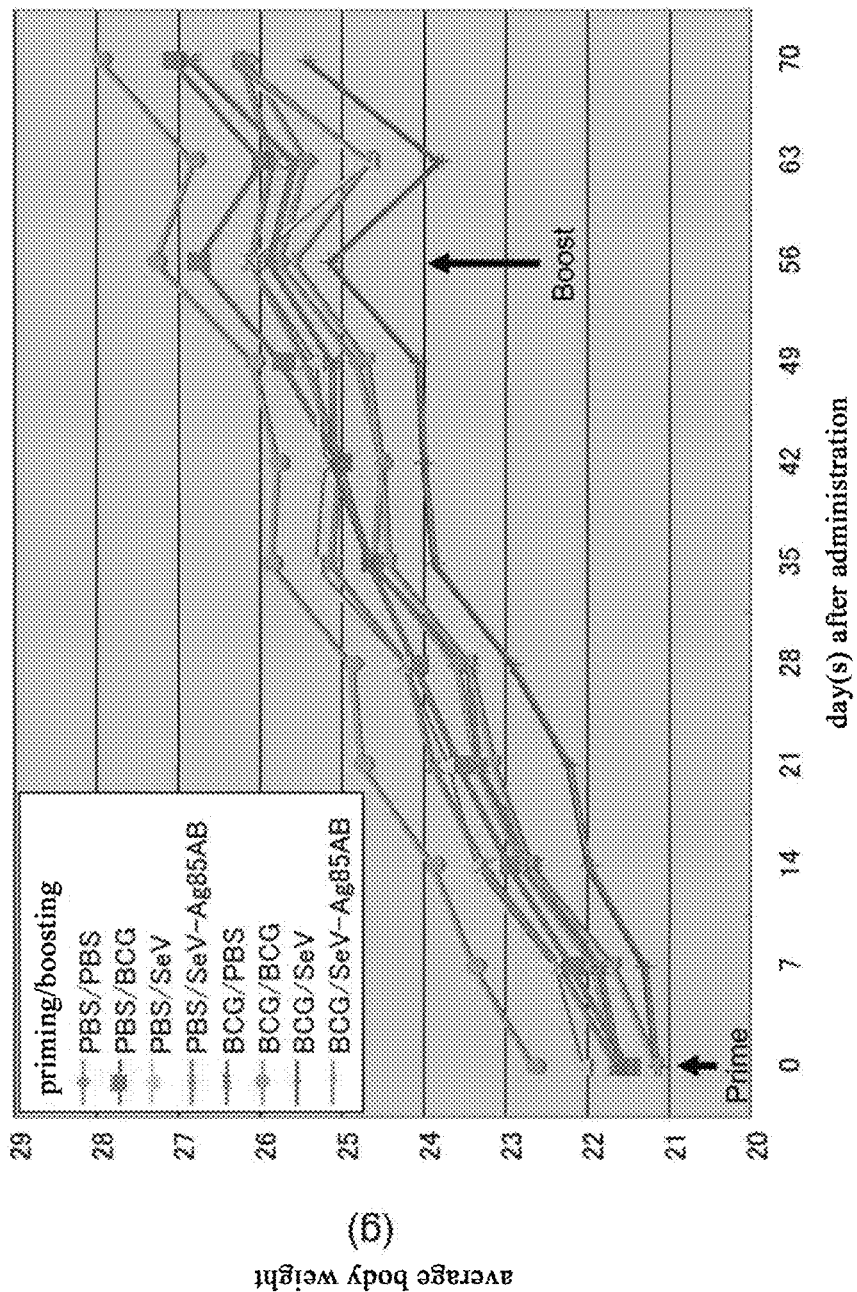
FIG. 11 shows changes in body weight of mice after administration of the eight priming-boosting schemes. The results demonstrate that mice immunized with BCG+SeV85AB did not show any significant change in body weight compared to other groups.

The ELISPOT results of the lung lymphocytes are shown in FIG. 9. Mice receiving a BCG primary immunization—SeV85AB boosting immunization can better induce lymphocytes secreting IFN-γ as compared to BCG boosting immunization. The results of spleens are shown in FIG. 10. Mice receiving BCG primary immunization—SeV85AB boosting immunization can also induce significantly more lymphocytes secreting IFN-γ as compared to BCG boosting immunization. That is, mice receiving the Group 8 immunization scheme showed induced local (lungs) and systemic (spleens) immune responses to the *tuberculosis* antigen Ag85A far superior to those of the other 7 groups. Meanwhile, any significant weight changes were not observed for SeV85AB immunized mice as compared to other test groups (FIG. 11).

Example 7

The Preventive Effect of SeV85AB Against *Mycobacterium tuberculosis* Infection as Compared to BCG Specific pathogen free (SPF) female BALB/c mice (6-8 weeks age) were purchased from Shanghai SLAC Laboratory Animal Co., Ltd. (Shanghai, China), as describe above. The mice were used to determine the prophylactic effect of SeV85AB against *Mycobacterium tuberculosis* infection.

Figure 12:
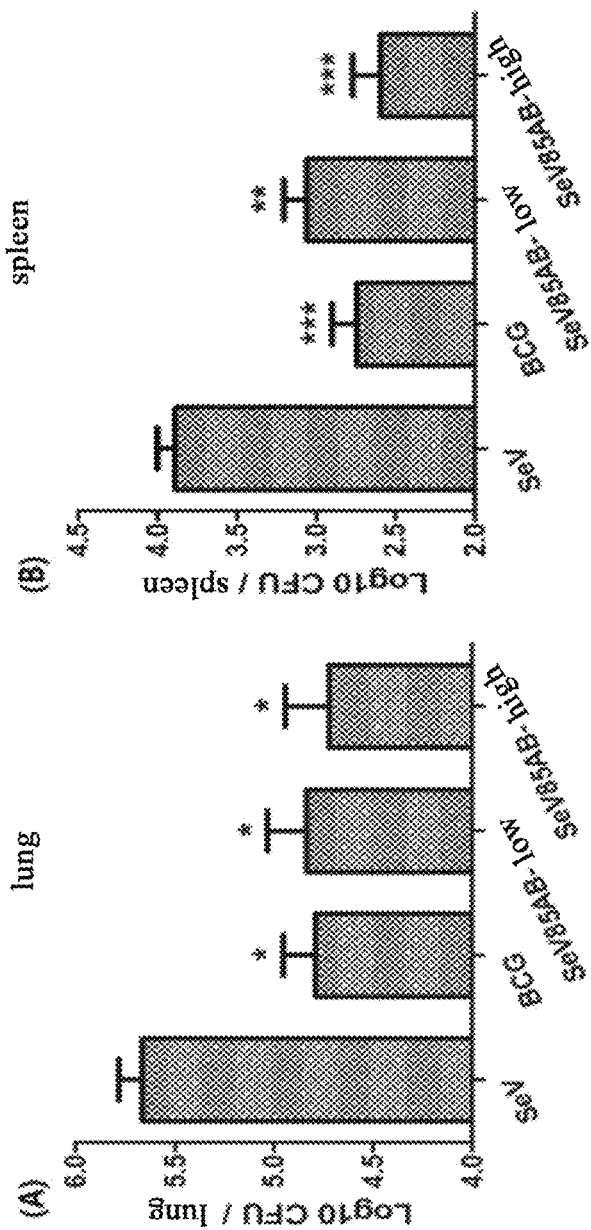
FIG. 12 shows the immunological effects measured with *Mycobacterium tuberculosis* challenge after the mice were immunized with SeV blank vector, BCG and different doses of SeV85AB.

The mice were divided into 4 groups, each immunized once with the blank SeV vector, the BCG vaccine (vaccinated at $10^6$ CFU once by subcutaneous injection), a low dosage ($2 \times 10^6$ CIU) of SeV85AB and a high dosage of SeV85AB ($10^7$ CIU), respectively. Four weeks later, the mice were challenged with an aerosol of *Mycobacterium tuberculosis* H37Rv strain (100-200 CFU) in a P3 lab. Next, 5 weeks later, the mice were sacrificed. Lung and spleen tissues of the mice were removed and homogenized into homogenate, which was plated onto a Middlebrook 7H11 agar plate supplemented with a four antibiotics mixture riched in 10% OADC and for preventing growth of contaminant microorganisms (40 U/ml polymycin B, 4 μg/ml amphotericin, 50 μg/ml carbenicillin, and 2 μg/ml trimethoprim). After incubation for 3 weeks at 37° C., the CFU colonies were counted, and the protective efficacy was evaluated. Student's t test was used to determine the significance between any two groups, and represented as * (if $p<0.05$) and *** (if $p<0.01$) in FIG. 12. A single nasal immunization with low dosage of SeV85AB can at least induce an immune protective effect equivalent to that of BCG, whereas the effect of high dosage of SeV85AB was even better than that of BCG, as shown in FIG. 12.

Example 8

The Preventive Effect of SeV85AB Against *Mycobacterium tuberculosis* Infection with Different Immunization Schemes Specific pathogen free (SPF) female BALB/c mice (6-8 weeks age) were purchased from Shanghai SLAC Laboratory Animal Co., Ltd. (Shanghai, China), as describe above. The mice were used to determine the preventive effect of SeV85AB against *Mycobacterium tuberculosis* infection.

Figure 13:
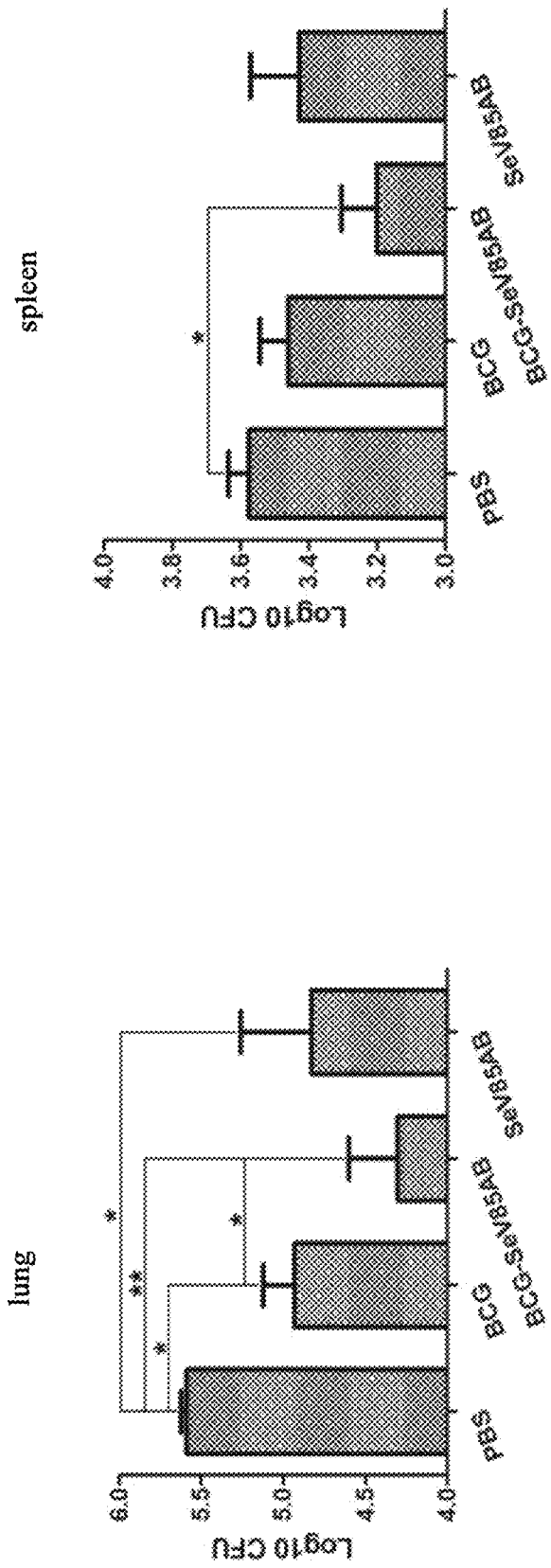
FIG. 13 shows the immunological effects measured with *Mycobacterium tuberculosis* challenge after the mice were immunized with different immunization schemes using PBS, BCG, BCG-SeV85AB and SeV85AB. The vertical coordinate is logarithm of CFU (colony forming unit), the left panel shows the result in the lung, and the right panel shows the result in the spleen. The results show that using a high concentration of SeV85AB ($10^7$ CIU) to immunize mice could induce a immunization effect similar to that of BCG vaccination, and boosting the BCG primed mice significantly decreased the amount of loaded bacteria, which indicates that SeV85AB vector vaccine is a promising candidate as a boosting vaccine for BCG.

The mice were divided into 4 groups, with Groups 1-3 immunized with PBS (20 μl), the BCG (vaccinated at $10^6$ CFU once by subcutaneous injection), and the BCG (vaccinated at $10^6$ CFU once by subcutaneous injection), respectively. Four weeks later, Group 3 was vaccinated nasally once with $10^7$ CIU SeV85AB as a booster (boosting immunization) and Group 4 was vaccinated nasally once with $10^7$ CIU SeV85AB. Another four weeks later, the mice were challenged with an aerosol of *Mycobacterium tuberculosis* H37Rv strain (100-200 CFU) in a P3 lab. Next, five weeks later, the mice were sacrificed. Lung and spleen tissues of the mice were removed and homogenized into homogenate, which was plated onto a Middlebrook 7H11 agar plate supplemented with a four antibiotics mixture riched in 10% OADC and for preventing growth of contaminant microorganisms (40 U/ml polymycin B, 4 μg/ml amphotericin, 50 μg/ml carbenicillin, and 2 μg/ml trimethoprim). After incubation for 3 weeks at 37° C., the CFU colonies were counted, and the protective efficacy was evaluated. Student's t test was used to determine the significance between any two groups, and represented as * (if $p<0.05$) and *** (if $p<0.01$) in FIG. 13. As shown in FIG. 13, in lungs, a single nasal immunization with SeV85AB alone can induce an immune protective effect equivalent to that of BCG alone, whereas if SeV85AB was used as a boosting vaccine for BCG, this would significantly increase the protective effect (the right panel of FIG. 13). In spleens, a single nasal immunization with SeV85AB alone can induce an immune protective effect equivalent to that of BCG alone, whereas if SeV85AB was used as a boosting vaccine for BCG, the effect was significantly superior to that of BCG or SeV85AB alone (the left panel of FIG. 13).

Example 9

The Inhibitory Effect of SeV85AB Against *Mycobacterium tuberculosis* In Vivo in *Mycobacterium tuberculosis* Infected Mice as Compared to Rifampicin Specific pathogen free (SPF) female BALB/c mice (6-8 weeks age) were purchased from Shanghai SLAC Laboratory Animal Co., Ltd. (Shanghai, China), as describe above. The mice were used to determine the inhibitory effect of SeV85AB against *Mycobacterium tuberculosis* in vivo.

Figure 14:
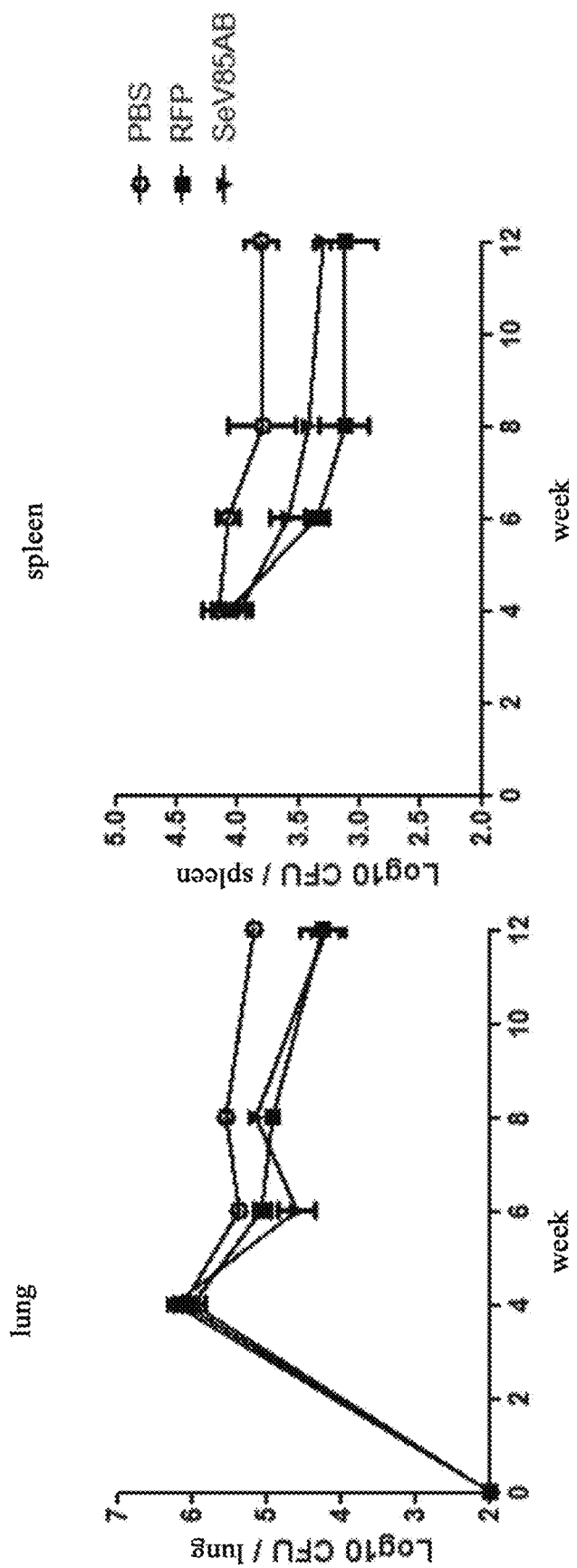
FIG. 14 shows the therapeutic effect of using rifampicin or SeV85AB on mice that have been challenged by *Mycobacterium tuberculosis*.

Firstly, the mice were challenged with an aerosol of 100-200 CFU H37Rv MTB strain. Four weeks after infection, the mice were divided into 3 groups, with 20 animals in each group. Group 1 was treated by adding rifampicin (RFP) into drinking water of the mice (at a dosage of 10 mg/kg/d). Group 2 was vaccinated with $10^7$ CIU SeV85AB nasally every two weeks for total three times. The control group was vaccinated with PBS (20 μl) by a nasal drip. At day 1, weeks 4, 6, 8 and 12 after infection, 3-4 mice were taken at each time point from each groups and sacrificed. Lung and spleen tissues of the mice were removed and homogenized into homogenate, which was plated onto a Middlebrook 7H11 agar plate supplemented with a four antibiotics mixture riched in 10% OADC and for preventing growth of contaminant microorganisms (40 U/ml polymycin B, 4 μg/ml amphotericin, 50 μg/ml carbenicillin, and 2 μg/ml trimethoprim). After incubation for 3 weeks at 37° C., the CFU colonies were counted to evaluate the therapeutic efficacy. The result demonstrated that the number of bacteria was markedly reduced with SeV85AB treatment after 4 weeks as compared to the PBS group, and the therapeutic effect was equivalent to that of the RFP group after a 8-week treatment (FIG. 14).

Example 10

The Inhibitory Effect of Combination Administration of SeV85AB and Rifampicin Against *Mycobacterium tuberculosis* In Vivo in *Mycobacterium tuberculosis* Infected Mice Specific pathogen free (SPF) female BALB/c mice (6-8 weeks age) were purchased from Shanghai SLAC Laboratory Animal Co., Ltd. (Shanghai, China), as describe above. The mice were used to determine the inhibitory effect of SeV85AB against *Mycobacterium tuberculosis* in vivo.

Figure 15:
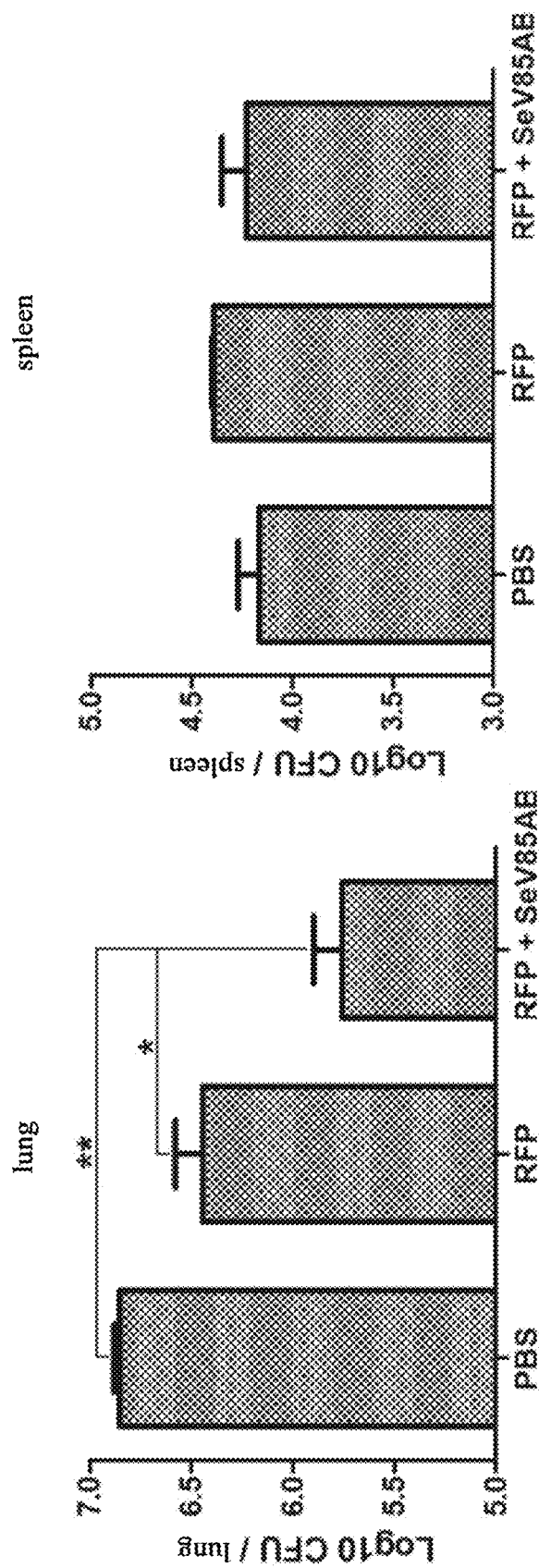
FIG. 15 shows the therapeutic effect of using PBS alone, rifampicin (RFP) alone, and a combination of rifampicin with SeV85AB on mice that have been challenged by *Mycobacterium tuberculosis*. It can be seen that immunotherapy with SeV85AB alone is comparable to the therapeutic effect of RFP drugs The combined therapy of rifampicin and SeV85AB significantly decreased the amount of loaded bacteria in the lungs of mice, indicating that combination of SeV85AB immunotherapy with anti-*tuberculosis* drugs can improve the therapeutic effect of anti-*tuberculosis* treatment.

Firstly, the mice were challenged with an aerosol of 100-200 CFU H37Rv MTB strain. Three weeks after infection, the mice were divided into 3 groups. Group 1 was treated by adding rifampicin (RFP) into drinking water of the mice (at a dosage of 10 mg/kg/d). Group 2 was vaccinated with $10^7$ CIU SeV85AB nasally once a week for a total of three times with simultaneous rifampicin treatment. The control group was vaccinated with PBS (20 μl) by a nasal drip. Six weeks after infection, the mice were sacrificed. Lung and spleen tissues of the mice were removed and homogenized into homogenate, which was plated onto a Middlebrook 7H11 agar plate supplemented with a four antibiotics mixture riched in 10% OADC and for preventing growth of contaminant microorganisms (40 U/ml polymycin B, 4 μg/ml amphotericin, 50 μg/ml carbenicillin, and 2 μg/ml trimethoprim). After incubation for three weeks at 37° C., the CFU colonies were counted to evaluate the therapeutic efficacy. As shown in FIG. 15, the results obtained in lungs shown, combination administration of rifampicin and SeV85AB can significantly reduce the bacteria load in the lungs of mice as compared to the PBS control and rifampicin alone (FIG. 15).

INDUSTRIAL APPLICABILITY

The present application provides a vaccine containing a Sendai virus vector encoding a *Mycobacterium tuberculosis* protein. Sendai virus has a low toxicity and can be used for a large scale production by cell culture. Thus, it is possible to produce living recombinant vaccines safely and easily. The vaccine of the present application also provide a promising scheme for inhibiting infection of *Mycobacterium tuberculosis* and/or development and progress of *tuberculosis*.

Deposit:

SeV85AB recombinant Sendai virus vector was deposited at China Center for Type CultureCollection (CCTCC, address: Luo JiaShan, Wuchang district of Wu Han city, Post Code: 430072) on Apr. 19, 2015 under the accession number of CCTCC V201518 (Taxonomy: Paramyxoviridae/ Paramyxovirus).

The invention claimed is:

1. A Sendai virus vector vaccine, wherein said vector expresses a *Mycobacterium tuberculosis* immunogenic antigen comprising SEQ ID NO: 8 or a variant thereof that is at least 90% identical to SEQ ID NO: 8.

2. The vaccine of claim 1, wherein the vector is a F gene defective Sendai virus vector.

3. A method for induce immune responses against *tuberculosis*, the method comprising administering to a subject in need thereof the Sendai virus vector vaccine of claim 1.

4. The method of claim 3, wherein the vaccine is administered by intranasal vaccination.

5. The method of claim 3, wherein the vaccine is administered to the subject at least once in the form of a multivalent vaccine.

6. A method for treating *tuberculosis*, the method comprising administering to a subject in need thereof the Sendai virus vector vaccine according to claim 1.

7. A recombinant Sendai virus vector, which is deposited at China Center for Type Culture Collection, under the accession number CCTCC V201518.

8. The vaccine of claim 1, wherein the *Mycobacterium tuberculosis* immunogenic antigen comprises an amino acid sequence of SEQ ID NO: 8.

9. A composition comprising the vaccine of claim 1.

10. A composition comprising the vaccine of claim 2.

11. A composition comprising the vaccine of claim 8.

12. A combination, comprising the composition of claim 9 and an additional *Mycobacterium tuberculosis* therapeutic agent.

13. The combination claim 12, wherein the additional *Mycobacterium tuberculosis* therapeutic agent is rifampicin or BCG vaccine.

14. A combination, comprising the composition of claim 10 and an additional *Mycobacterium tuberculosis* therapeutic agent.

15. The combination of claim 14, wherein the additional *Mycobacterium tuberculosis* therapeutic agent is rifampicin or BCG vaccine.

16. A combination, comprising the composition of claim 11 and an additional *Mycobacterium tuberculosis* therapeutic agent.

17. The combination of claim 16, wherein the additional *Mycobacterium tuberculosis* therapeutic agent is rifampicin or BCG vaccine.

* * * * *

SEQUENCE LISTING

```
<160> NUMBER OF SEQ ID NOS: 18

<210> SEQ ID NO 1
<211> LENGTH: 888
<212> TYPE: DNA
<213> ORGANISM: mycobacterium tuberculosis

<400> SEQUENCE: 1
ttttcccggc cgggcttgcc ggtggagtac ctgcaggtgc cgtcgccgtc gatgggccgt      60
gacatcaagg tccaattcca aagtggtggt gccaactcgc ccgccctgta cctgctcgac     120
ggcctgcgcg cgcaggacga cttcagcggc tgggacatca cacccggc gttcgagtgg       180 tacgaccagt cgggcctgtc ggtggtcatg ccggtgggtg gccagtcaag cttctactcc     240
gactggtacc agcccgcctg cggcaaggcc ggttgccaga cttacaagtg ggagaccttc     300
ctgaccagcg agctgccggg gtggctgcag gccaacaggc acgtcaagcc caccggaagc     360
gccgtcgtcg gtctttcgat ggctgcttct tcggcgctga cgctggcgat ctatcacccc     420
cagcagttcg tctacgcggg agcgatgtcg ggcctgttgg accctccca ggcgatgggt      480 cccaccctga tcggcctggc gatgggtgac gctggcggct acaaggcctc cgacatgtgg     540
ggcccgaagg aggacccggc gtggcagcgc aacgaccgc tgttgaacgt cgggaagctg      600
atcgccaaca cacccgcgt ctgggtgtac tgcggcaacg gcaagccgtc ggatctgggt      660
ggcaacaacc tgccggccaa gttcctcgag ggcttcgtgc ggaccagcaa catcaagttc      720
caagacgcct acaacgccgg tggcggccac aacgcgtgt tcgacttccc ggacagcggt      780
acgcacagct gggagtactg gggcgcgcag ctcaacgcta tgaagcccga cctgcaacgg     840
gcactgggtg ccacgcccaa caccgggccc gcgcccagg gcgcctag                   888

<210> SEQ ID NO 2
<211> LENGTH: 295
<212> TYPE: PRT
<213> ORGANISM: mycobacterium tuberculosis
```

<400> SEQUENCE: 2

```
Phe Ser Arg Pro Gly Leu Pro Val Glu Tyr Leu Gln Val Pro Ser Pro
 1               5                  10                  15

Ser Met Gly Arg Asp Ile Lys Val Gln Phe Gln Ser Gly Gly Ala Asn
            20                  25                  30

Ser Pro Ala Leu Tyr Leu Leu Asp Gly Leu Arg Ala Gln Asp Asp Phe
        35                  40                  45

Ser Gly Trp Asp Ile Asn Thr Pro Ala Phe Glu Trp Tyr Asp Gln Ser
    50                  55                  60

Gly Leu Ser Val Val Met Pro Val Gly Gly Gln Ser Ser Phe Tyr Ser
65                  70                  75                  80

Asp Trp Tyr Gln Pro Ala Cys Gly Lys Ala Gly Cys Gln Thr Tyr Lys
                85                  90                  95

Trp Glu Thr Phe Leu Thr Ser Glu Leu Pro Gly Trp Leu Gln Ala Asn
            100                 105                 110

Arg His Val Lys Pro Thr Gly Ser Ala Val Val Gly Leu Ser Met Ala
        115                 120                 125

Ala Ser Ser Ala Leu Thr Leu Ala Ile Tyr His Pro Gln Gln Phe Val
    130                 135                 140

Tyr Ala Gly Ala Met Ser Gly Leu Leu Asp Pro Ser Gln Ala Met Gly
145                 150                 155                 160

Pro Thr Leu Ile Gly Leu Ala Met Gly Asp Ala Gly Gly Tyr Lys Ala
                165                 170                 175

Ser Asp Met Trp Gly Pro Lys Glu Asp Pro Ala Trp Gln Arg Asn Asp
            180                 185                 190

Pro Leu Leu Asn Val Gly Lys Leu Ile Ala Asn Asn Thr Arg Val Trp
        195                 200                 205

Val Tyr Cys Gly Asn Gly Lys Pro Ser Asp Leu Gly Gly Asn Asn Leu
    210                 215                 220

Pro Ala Lys Phe Leu Glu Gly Phe Val Arg Thr Ser Asn Ile Lys Phe
225                 230                 235                 240

Gln Asp Ala Tyr Asn Ala Gly Gly His Asn Gly Val Phe Asp Phe
                245                 250                 255

Pro Asp Ser Gly Thr His Ser Trp Glu Tyr Trp Gly Ala Gln Leu Asn
            260                 265                 270

Ala Met Lys Pro Asp Leu Gln Arg Ala Leu Gly Ala Thr Pro Asn Thr
        275                 280                 285

Gly Pro Ala Pro Gln Gly Ala
        290                 295
```

<210> SEQ ID NO 3
<211> LENGTH: 858
<212> TYPE: DNA
<213> ORGANISM: mycobacterium tuberculosis

<400> SEQUENCE: 3

```
ttctcccggc cggggctgcc ggtcgagtac ctgcaggtgc cgtcgccgtc gatgggccgc    60
gacatcaagg ttcagttcca gagcggtggg aacaactcac ctgcggttta tctgctcgac   120
ggcctgcgcg cccaagacga ctacaacggc tgggatatca cacccccggc gttcgagtgg   180
tactaccagt cgggactgtc gatagtcatg ccggtcggcg gcagtccag cttctacagc    240 gactggtaca gccggcctg cggtaaggct ggctgccaga cttacaagtg gaaaccttc    300 ctgaccagcg agctgccgca atggttgtcc gccaacaggg ccgtgaagcc caccggcagc   360
```

```
gctgcaatcg gcttgtcgat ggccggctcg tcggcaatga tcttggccgc ctaccacccc    420
cagcagttca tctacgccgg ctcgctgtcg gccctgctgg accctctca ggggatgggg     480 cctagcctga tcggcctcgc gatgggtgac gccggcggtt acaaggccgc agacatgtgg    540 ggtcccctcga gtgaccccggc atgggagcgc aacgaccca cgcagcagat ccccaagctg   600
gtcgcaaaca cacccggct atgggtttat tgcgggaacg gcaccccgaa cgagttgggc     660
ggtgccaaca tacccgccga gttcttggag aacttcgttc gtagcagcaa cctgaagttc    720
caggatgcgt acaacgccgc gggcgggcac aacgccgtgt tcaacttccc gcccaacggc    780
acgcacagct gggagtactg gggcgctcag ctcaacgcca tgaagggtga cctgcagagt    840
tcgttaggcg ccggctga                                                 858
```

<210> SEQ ID NO 4
<211> LENGTH: 285
<212> TYPE: PRT
<213> ORGANISM: mycobacterium tuberculosis

<400> SEQUENCE: 4

```
Phe Ser Arg Pro Gly Leu Pro Val Glu Tyr Leu Gln Val Pro Ser Pro
1               5                   10                  15

Ser Met Gly Arg Asp Ile Lys Val Gln Phe Gln Ser Gly Gly Asn Asn
            20                  25                  30

Ser Pro Ala Val Tyr Leu Leu Asp Gly Leu Arg Ala Gln Asp Asp Tyr
        35                  40                  45

Asn Gly Trp Asp Ile Asn Thr Pro Ala Phe Glu Trp Tyr Tyr Gln Ser
    50                  55                  60

Gly Leu Ser Ile Val Met Pro Val Gly Gly Gln Ser Ser Phe Tyr Ser
65                  70                  75                  80

Asp Trp Tyr Ser Pro Ala Cys Gly Lys Ala Gly Cys Gln Thr Tyr Lys
                85                  90                  95

Trp Glu Thr Phe Leu Thr Ser Glu Leu Pro Gln Trp Leu Ser Ala Asn
            100                 105                 110

Arg Ala Val Lys Pro Thr Gly Ser Ala Ala Ile Gly Leu Ser Met Ala
        115                 120                 125

Gly Ser Ser Ala Met Ile Leu Ala Ala Tyr His Pro Gln Gln Phe Ile
    130                 135                 140

Tyr Ala Gly Ser Leu Ser Ala Leu Leu Asp Pro Ser Gln Gly Met Gly
145                 150                 155                 160

Pro Ser Leu Ile Gly Leu Ala Met Gly Asp Ala Gly Gly Tyr Lys Ala
                165                 170                 175

Ala Asp Met Trp Gly Pro Ser Ser Asp Pro Ala Trp Glu Arg Asn Asp
            180                 185                 190

Pro Thr Gln Gln Ile Pro Lys Leu Val Ala Asn Asn Thr Arg Leu Trp
        195                 200                 205

Val Tyr Cys Gly Asn Gly Thr Pro Asn Glu Leu Gly Gly Ala Asn Ile
    210                 215                 220

Pro Ala Glu Phe Leu Glu Asn Phe Val Arg Ser Ser Asn Leu Lys Phe
225                 230                 235                 240

Gln Asp Ala Tyr Asn Ala Ala Gly Gly His Asn Ala Val Phe Asn Phe
                245                 250                 255

Pro Pro Asn Gly Thr His Ser Trp Glu Tyr Trp Gly Ala Gln Leu Asn
            260                 265                 270

Ala Met Lys Gly Asp Leu Gln Ser Ser Leu Gly Ala Gly
        275                 280                 285
```

<210> SEQ ID NO 5
<211> LENGTH: 158
<212> TYPE: PRT
<213> ORGANISM: mycobacterium tuberculosis

<400> SEQUENCE: 5

```
Leu Ser Met Ala Gly Ser Ser Ala Met Ile Leu Ala Ala Tyr His Pro
1               5                   10                  15

Gln Gln Phe Ile Tyr Ala Gly Ser Leu Ser Ala Leu Leu Asp Pro Ser
            20                  25                  30

Gln Gly Met Gly Pro Ser Leu Ile Gly Leu Ala Met Gly Asp Ala Gly
        35                  40                  45

Gly Tyr Lys Ala Ala Asp Met Trp Gly Pro Ser Ser Asp Pro Ala Trp
    50                  55                  60

Glu Arg Asn Asp Pro Thr Gln Gln Ile Pro Lys Leu Val Ala Asn Asn
65                  70                  75                  80

Thr Arg Leu Trp Val Tyr Cys Gly Asn Gly Thr Pro Asn Glu Leu Gly
                85                  90                  95

Gly Ala Asn Ile Pro Ala Glu Phe Leu Glu Asn Phe Val Arg Ser Ser
            100                 105                 110

Asn Leu Lys Phe Gln Asp Ala Tyr Asn Ala Ala Gly Gly His Asn Ala
        115                 120                 125

Val Phe Asn Phe Pro Pro Asn Gly Thr His Ser Trp Glu Tyr Trp Gly
    130                 135                 140

Ala Gln Leu Asn Ala Met Lys Gly Asp Leu Gln Ser Ser Leu
145                 150                 155
```

<210> SEQ ID NO 6
<211> LENGTH: 1368
<212> TYPE: DNA
<213> ORGANISM: artificial sequence
<220> FEATURE:
<223> OTHER INFORMATION: Ag85AB chimeric gene(using AccI site as chimeric site)

<400> SEQUENCE: 6

```
atggtttccc ggccgggctt gccggtggag tacctgcagg tgccgtcgcc gtcgatgggc        60
cgtgacatca aggtccaatt ccaaagtggt ggtgccaact cgcccgccct gtacctgctc       120
gacggcctgc gcgcgcagga cgacttcagc ggctgggaca tcaacacccc ggcgttcgag       180
tggtacgacc agtcgggcct gtcggtggtc atgccggtgg tggccagtc aagcttctac        240
tccgactggt accagccggc ctgcggcaag gccggttgcc agacttacaa gtgggagacc       300
ttcctgacca gcgagctgcc ggggtggctg caggccaaca ggcacgtcaa gcccaccgga       360
agcgccgtcg tcggtctttc gatggctgct tcttcggcgc tgacgctggc gatctatcac       420
ccccagcagt tcgtctactc gatggccggc tcgtcggcaa tgatcttggc cgcctaccac       480
ccccagcagt tcatctacgc cggctcgctg tcggccctgc tggaccccct caggggatg        540
gggcctagcc tgatcggcct cgcgatgggt gacgccggcg gttacaaggc cgcagacatg       600
tggggtccct cgagtgaccc ggcatgggag cgcaacgacc ctacgcagca gatccccaag       660
ctggtcgcaa acaacacccg gctatgggtt tattgcggga acggcacccc gaacgagttg       720
ggcggtgcca acatacccgc cgagttcttg gagaacttcg ttcgtagcag caacctgaag       780
ttccaggatg cgtacaacgc cgcgggcggg cacaacgccg tgttcaactt cccgcccaac       840
```

| | |
|---|---|
| ggcacgcaca gctgggagta ctggggcgct cagctcaacg ccatgaaggg tgacctgcag | 900 |
| agttcgttag tctacgcggg agcgatgtcg ggcctgttgg acccctccca ggcgatgggt | 960 |
| cccaccctga tcggcctggc gatgggtgac gctggcggct acaaggcctc cgacatgtgg | 1020 |
| ggcccgaagg aggacccggc gtggcagcgc aacgacccgc tgttgaacgt cgggaagctg | 1080 |
| atcgccaaca cacccgcgt ctgggtgtac tgcggcaacg gcaagccgtc ggatctgggt | 1140 |
| ggcaacaacc tgccggccaa gttcctcgag ggcttcgtgc ggaccagcaa catcaagttc | 1200 |
| caagacgcct acaacgccgg tggcggccac aacggcgtgt tcgacttccc ggacagcggt | 1260 |
| acgcacagct gggagtactg gggcgcgcag ctcaacgcta tgaagcccga cctgcaacgg | 1320 |
| gcactgggtg ccacgcccaa caccgggccc gcgccccagg gcgcctag | 1368 |

<210> SEQ ID NO 7
<211> LENGTH: 1368
<212> TYPE: DNA
<213> ORGANISM: artificial sequence
<220> FEATURE:
<223> OTHER INFORMATION: Ag85AB chimeric gene(using KpnI site as chimeric site)

<400> SEQUENCE: 7

| | |
|---|---|
| atggtttccc ggccgggctt gccggtggag tacctgcagg tgccgtcgcc gtcgatgggc | 60 |
| cgtgacatca aggtccaatt ccaaagtggt ggtgccaact cgcccgccct gtacctgctc | 120 |
| gacggcctgc gcgcgcagga cgacttcagc ggctgggaca tcaacacccc ggcgttcgag | 180 |
| tggtacgacc agtcgggcct gtcggtggtc atgccggtgg gtggccagtc aagcttctac | 240 |
| tccgactggt acctcgatgg ccggctcgtc ggcaatgatc ttggccgcct accaccccca | 300 |
| gcagttcatc tacgccggct cgctgtcggc cctgctggac ccctctcagg gatggggcc | 360 |
| tagcctgatc ggcctcgcga tgggtgacgc cggcggttac aaggccgcag acatgtgggg | 420 |
| tccctcgagt gacccggcat gggagcgcaa cgaccctacg cagcagatcc ccaagctggt | 480 |
| cgcaaacaac acccggctat gggtttattg cgggaacggc accccgaacg agttgggcgg | 540 |
| tgccaacata cccgccgagt tcttggagaa cttcgttcgt agcagcaacc tgaagttcca | 600 |
| ggatgcgtac aacgccgcgg gcgggcacaa cgccgtgttc aacttcccgc caacggcac | 660 |
| gcacagctgg gagtactggg gcgctcagct caacgccatg aagggtgacc tgcagagttc | 720 |
| gttaggtacc agcccgcctg cggcaaggcc ggttgccaga cttacaagtg ggagaccttc | 780 |
| ctgaccagcg agctgccggg gtggctgcag gccaacaggc acgtcaagcc caccggaagc | 840 |
| gccgtcgtcg gtctttcgat ggctgcttct tcggcgctga cgctggcgat ctatcacccc | 900 |
| cagcagttcg tctacgcggg agcgatgtcg ggcctgttgg acccctccca ggcgatgggt | 960 |
| cccaccctga tcggcctggc gatgggtgac gctggcggct acaaggcctc cgacatgtgg | 1020 |
| ggcccgaagg aggacccggc gtggcagcgc aacgacccgc tgttgaacgt cgggaagctg | 1080 |
| atcgccaaca cacccgcgt ctgggtgtac tgcggcaacg gcaagccgtc ggatctgggt | 1140 |
| ggcaacaacc tgccggccaa gttcctcgag ggcttcgtgc ggaccagcaa catcaagttc | 1200 |
| caagacgcct acaacgccgg tggcggccac aacggcgtgt tcgacttccc ggacagcggt | 1260 |
| acgcacagct gggagtactg gggcgcgcag ctcaacgcta tgaagcccga cctgcaacgg | 1320 |
| gcactgggtg ccacgcccaa caccgggccc gcgccccagg gcgcctag | 1368 |

<210> SEQ ID NO 8
<211> LENGTH: 454
<212> TYPE: PRT

<213> ORGANISM: artificial sequence
<220> FEATURE:
<223> OTHER INFORMATION: chimeric Ag85AB protein

<400> SEQUENCE: 8

```
Phe Ser Arg Pro Gly Leu Pro Val Glu Tyr Leu Gln Val Pro Ser Pro
1               5                   10                  15

Ser Met Gly Arg Asp Ile Lys Val Gln Phe Gln Ser Gly Gly Ala Asn
            20                  25                  30

Ser Pro Ala Leu Tyr Leu Leu Asp Gly Leu Arg Ala Gln Asp Asp Phe
        35                  40                  45

Ser Gly Trp Asp Ile Asn Thr Pro Ala Phe Glu Trp Tyr Asp Gln Ser
50                  55                  60

Gly Leu Ser Val Val Met Pro Val Gly Gly Gln Ser Ser Phe Tyr Ser
65                  70                  75                  80

Asp Trp Tyr Gln Pro Ala Cys Gly Lys Ala Gly Cys Gln Thr Tyr Lys
                85                  90                  95

Trp Glu Thr Phe Leu Thr Ser Glu Leu Pro Gly Trp Leu Gln Ala Asn
            100                 105                 110

Arg His Val Lys Pro Thr Gly Ser Ala Val Val Gly Leu Ser Met Ala
        115                 120                 125

Ala Ser Ser Ala Leu Thr Leu Ala Ile Tyr His Pro Gln Gln Phe Val
130                 135                 140

Tyr Ser Met Ala Gly Ser Ser Ala Met Ile Leu Ala Ala Tyr His Pro
145                 150                 155                 160

Gln Gln Phe Ile Tyr Ala Gly Ser Leu Ser Ala Leu Leu Asp Pro Ser
                165                 170                 175

Gln Gly Met Gly Pro Ser Leu Ile Gly Leu Ala Met Gly Asp Ala Gly
            180                 185                 190

Gly Tyr Lys Ala Ala Asp Met Trp Gly Pro Ser Ser Asp Pro Ala Trp
        195                 200                 205

Glu Arg Asn Asp Pro Thr Gln Gln Ile Pro Lys Leu Val Ala Asn Asn
210                 215                 220

Thr Arg Leu Trp Val Tyr Cys Gly Asn Gly Thr Pro Asn Glu Leu Gly
225                 230                 235                 240

Gly Ala Asn Ile Pro Ala Glu Phe Leu Glu Asn Phe Val Arg Ser Ser
                245                 250                 255

Asn Leu Lys Phe Gln Asp Ala Tyr Asn Ala Ala Gly Gly His Asn Ala
            260                 265                 270

Val Phe Asn Phe Pro Pro Asn Gly Thr His Ser Trp Glu Tyr Trp Gly
        275                 280                 285

Ala Gln Leu Asn Ala Met Lys Gly Asp Leu Gln Ser Ser Leu Val Tyr
290                 295                 300

Ala Gly Ala Met Ser Gly Leu Leu Asp Pro Ser Gln Ala Met Gly Pro
305                 310                 315                 320

Thr Leu Ile Gly Leu Ala Met Gly Asp Ala Gly Gly Tyr Lys Ala Ser
                325                 330                 335

Asp Met Trp Gly Pro Lys Glu Asp Pro Ala Trp Gln Arg Asn Asp Pro
            340                 345                 350

Leu Leu Asn Val Gly Lys Leu Ile Ala Asn Asn Thr Arg Val Trp Val
        355                 360                 365

Tyr Cys Gly Asn Gly Lys Pro Ser Asp Leu Gly Asn Asn Leu Pro
370                 375                 380

Ala Lys Phe Leu Glu Gly Phe Val Arg Thr Ser Asn Ile Lys Phe Gln
```

```
                385               390                395                400
Asp Ala Tyr Asn Ala Gly Gly Gly His Asn Gly Val Phe Asp Phe Pro
                        405                 410                415

Asp Ser Gly Thr His Ser Trp Glu Tyr Trp Gly Ala Gln Leu Asn Ala
                    420                 425                 430

Met Lys Pro Asp Leu Gln Arg Ala Leu Gly Ala Thr Pro Asn Thr Gly
                435                 440                 445

Pro Ala Pro Gln Gly Ala
    450

<210> SEQ ID NO 9
<211> LENGTH: 16362
<212> TYPE: DNA
<213> ORGANISM: artificial sequence
<220> FEATURE:
<223> OTHER INFORMATION: F gene deleted Sendai virus vector

<400> SEQUENCE: 9
```

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgccaa | gctcgcgtcg | tacgggccct | 420 |
| aatacgactc | actataacca | acaagagaa | aaacatgta | tgggatatgt | aatgaagtta | 480 |
| tacaggattt | tagggtcaaa | gtatccaccc | tgaggagca | gttccagacc | ctttgctttg | 540 |
| ctgccaaagt | tcacgcggcc | gcagatcttc | acgatggccg | ggttgttgag | caccttcgat | 600 |
| acatttagct | ctaggaggag | cgaaagtatt | aataagtcgg | gaggaggtgc | tgttatcccc | 660 |
| ggccagagga | gcacagtctc | agtgttcgta | ctaggcccaa | gtgtgactga | tgatgcagac | 720 |
| aagttattca | ttgcaactac | cttcctagct | cactcattgg | acacagataa | gcagcactct | 780 |
| cagagagggg | ggttcctcgt | ctctctgctt | gccatggctt | acagtagtcc | agaattgtac | 840 |
| ttgacaacaa | acggagtaaa | cgccgatgtc | aaatatgtga | tctacaacat | agagaaagac | 900 |
| cctaagagga | cgaagacaga | cggattcatt | gtgaagacga | gagatatgga | atatgagagg | 960 |
| accacagaat | ggctgtttgg | acctatggtc | aacaagagcc | cactcttcca | gggtcaacgg | 1020 |
| gatgctgcag | accctgacac | actccttcaa | atctatgggt | atcctgcatg | cctaggagca | 1080 |
| ataattgtcc | aagtctggat | tgtgctggtg | aaggccatca | agcagcgc | cggcttaagg | 1140 |
| aaagggttct | tcaacaggtt | agaggcgttc | agacaagacg | gcaccgtgaa | aggtgcctta | 1200 |
| gttttcactg | gggagacagt | tgagggata | ggctcggtta | tgagatctca | gcaaagcctt | 1260 |
| gtatctctca | tggttgagac | ccttgtgact | atgaatactg | caagatctga | tctcaccaca | 1320 |
| ttagagaaga | acatccagat | cgttgggaac | tacatccgag | atgcagggct | ggcttccttc | 1380 |
| atgaacacta | ttaatatgg | ggtggaaaca | aagatgcag | ctctaacgtt | gtcaaacctg | 1440 |
| aggcccgata | ttaataagct | tagaagcctc | atagacacct | acctgtcaaa | aggccccaga | 1500 |
| gctcccttta | tctgtatcct | caaggaccct | gttcatggtg | aatttgctcc | aggcaattat | 1560 |
| cctgcactat | ggagttacgc | catgggagtc | gccgtcgtac | agaacaaggc | aatgcagcag | 1620 |
| tacgtcacag | ggaggacata | ccttgatatg | gaaatgttct | tactaggaca | agccgtggca | 1680 |

```
aaggatgctg aatcgaagat cagcagtgcc ttggaagatg agttaggagt gacggataca   1740 gccaaggga ggctcagaca tcatctggca aacttgtccg gtggggatgg tgcttaccac    1800
aaaccaacag gcggtggtgc aattgaggta gctctagaca atgccgacat cgacctagaa   1860
acaaaagccc atgcggacca ggacgctagg ggttggggtg gagatagtgg tgaaagatgg   1920
gcacgtcagg tgagtggtgg ccactttgtc acactacatg gggctgaacg gttagaggag   1980
gaaaccaatg atgaggatgt atcagacata gagagaagaa tagccatgag actcgcagag   2040
agacggcaag aggattctgc aacccatgga gatgaaggcc gcaataacgg tgtcgatcat   2100
gacgaagatg acgatgccgc agcagtagct gggataggag gaatctagga tcatacgagg   2160
cttcaaggta cttgatccgt agtaagaaaa acttagggtg aaagttcatc caccgatcgg   2220
ctcaggcaag gccacaccca accccaccga ccacacccag cagtcgagac agccacggct   2280
tcggctacac ttaccgcatg gatcaagatg ccttcattct taaagaagat tctgaagttg   2340
agagggaggc gccaggagga cgagagtcgc tctcggatgt tatcggattc ctcgatgctg   2400
tcctgtcgag tgaaccaact gacatcggag gggacagaag ctggctccac aacaccatca   2460
acactcccca aggaccaggc tctgctcata gagccaaaag tgaggcgaa ggagaagtct    2520 caacaccgtc gacccaagat aatcgatcag gtgaggagag tagagtctct gggagaacaa   2580
gcaagccaga ggcagaagca catgctggaa accttgataa acaaaatata caccgggcct   2640
ttgggggaag aactggtaca aactctgtat ctcaggatct gggcgatgga ggagactccg   2700
gaatccttga aaatcctcca aatgagagag gatatccgag atcaggtatt gaagatgaaa   2760
acagagagat ggctgcgcac cctgataaga ggggagaaga ccaagctgaa ggacttccag   2820
aagaggtacg aggaagtaca tccctacctg atgaaggaga aggtggagca agtaataatg   2880
gaagaagcat ggagcctggc agctcacata gtgcaagagt aactgggtc ctggtgattc    2940 ctagccccga acttgaagag gctgtgctac ggaggaacaa aagaagacct accaacagtg   3000
ggtccaaacc tcttactcca gcaaccgtgc ctggcacccg gtccccaccg ctgaatcgtt   3060
acaacagcac agggtcacca ccaggaaaac ccccatctac acaggatgag cacatcaact   3120
ctggggacac ccccgccgtc agggtcaaag accggaaacc accaataggg acccgctctg   3180
tctcagattg tccagccaac ggccgcccaa tccacccggg tctagagacc gactcaacaa   3240 aaagggcat aggagagaac acatcatcta tgaaagagat ggctacattg ttgacgagtc     3300
ttggtgtaat ccagtctgct caagaattcg aatcatcccg agacgcgagt tatgtgtttg   3360
caagacgtgc cctaaagtct gcaaactatg cagagatgac attcaatgta tgcggcctga   3420
tcctttctgc cgagaaatct tccgctcgta aggtagatga gaacaaacaa ctgctcaaac   3480
agatccaaga gagcgtggaa tcattcccggg atatttacaa gagattctct gagtatcaga   3540
aagaacagaa ctcattgctg atgtccaacc tatctacact tcatatcatc acagatagag   3600
gtggcaagac tgacaacaca gactcccctta caaggtcccc ctccgttttt gcaaaatcaa   3660
aagagaacaa gactaaggct accaggtttg acccatctat ggagaccta gaagatatga    3720 agtacaaacc ggacctaatc cgagaggatg aatttagaga tgagatccgc aacccggtgt   3780
accaagagag ggacacagaa cccagggcct caaacgcatc acgtctcctc ccctccaaag   3840
agaagcccac aatgcactct ctcaggctcg tcatagagag cagtcccta agcagagctg    3900 agaaagtagc atatgtgaaa tcattatcca agtgcaagac agaccaagag gttaaggcag   3960
tcatggaact cgtagaagag gacatagagt cactgaccaa ctagatcccg ggtgaggcat   4020
```

```
cctaccatcc tcagtcatag agagatccaa tctaccatca gcatcagcca gtaaagatta      4080
agaaaaactt agggtgaaag aaatttcacc taacacggcg caatggcaga tatctataga      4140
ttccctaagt tctcatatga ggataacggt actgtggagc ccctgcctct gagaactggt      4200
ccggataaga aagccatccc ccacatcagg attgtcaagg taggagaccc tcctaaacat      4260
ggagtgagat acctagattt attgctcttg ggtttctttg agacaccgaa acaaacaacc      4320
aatctaggga gcgtatctga cttgacagag ccgaccagct actcaatatg cggctccggg      4380
tcgttaccca taggtgtggc caaatactac gggactgatc aggaactctt aaaggcctgc      4440
accgatctca gaattacggt gaggaggact gttcgagcag gagagatgat cgtatacatg      4500
gtggattcga ttggtgctcc actcctacca tggtcaggca ggctgagaca gggaatgata      4560
tttaatgcaa acaaggtcgc actagctccc caatgcctcc ctgtggacaa ggacataaga      4620
ctcagagtgg tgtttgtcaa tgggacatct ctagggggcaa tcaccatagc caagatccca      4680
aagacccttg cagaccttgc attgcccaac tctatatctg ttaatttact ggtgacactc      4740
aagacccgga tctccacaga acaaaagggg gtactcccag tacttgatga tcaagggggag      4800 aaaaagctca attttatggt gcacctcggg ttgatcagga gaaaggtcgg gaagatatac      4860
tctgttgagt actgcaagag caagattgag agaatgcggc tgattttctc acttgggtta      4920
atcggcggta taagcttcca tgttcaggtt aatgggacac tatctaagac attcatgagt      4980
cagctcgcat ggaagagggc agtctgcttc ccattaatgg atgtgaatcc ccatatgaac      5040
atggtgattt gggcggcatc tgtagaaatc acaggcgtcg atgcggtgtt ccaaccggcc      5100
atccctcgtg atttccgcta ctaccctaat gttgtggcta agaacatcgg aaggatcaga      5160
aagctgtaaa tgtgcaccca tcagagacct gcgacaatgc cccaagcaga caccacctgg      5220
cagtcggagc caccgggtca ctccttgtct taaataagaa aaacttaggg ataaagtccc      5280
ttgtgagtgc ttggttgcaa aactctccac ctggtacaag cacagatcat ggatggtgat      5340
aggggcaaac gtgactcgta ctggtctact tctcctagtg gtagcaccac aaaaccagca      5400
tcaggttggg agaggtcaag taaagccgac acatggttgc tgattctctc attcacccag      5460
tgggctttgt caattgccac agtgatcatc tgtatcataa tttctgctag acaagggtat      5520
agtatgaaag agtactcaat gactgtagag gcattgaaca tgagcagcag ggaggtgaaa      5580
gagtcactta ccagtctaat aaggcaagag gttatagcaa gggctgtcaa cattcagagc      5640
tctgtgcaaa ccggaatccc agtcttgttg aacaaaaaca gcagggatgt catccagatg      5700
attgataagt cgtgcagcag acaagagctc actcagcact gtgagagtac gatcgcagtc      5760
caccatgccg atggaattgc cccacttgag ccacatagtt tctggagatg ccctgtcgga      5820
gaaccgtatc ttagctcaga tcctgaaatc tcattgctgc ctggtccgag cttgttatct      5880
ggttctacaa cgatctctgg atgtgttagg ctcccttcac tctcaattgg cgaggcaatc      5940
tatgcctatt catcaaatct cattacacaa ggttgtgctg acatagggaa atcatatcag      6000
gtcctgcagc tagggtacat atcactcaat tcagatatgt tccctgatct taaccccgta      6060
gtgtcccaca cttatgacat caacgacaat cggaaatcat gctctgtggt ggcaaccggg      6120
actaggggtt atcagctttg ctccatgccg actgtagacg aaagaaccga ctactctagt      6180
gatggtattg aggatctggt ccttgatgtc ctggatctca agggagaac taagtctcac      6240 cggtatcgca acagcgaggt agatcttgat caccgttct ctgcactata ccccagtgta      6300
ggcaacggca ttgcaacaga aggctcattg atatttcttg ggtatggtgg actaaccacc      6360
cctctgcagg gtgatacaaa atgtaggacc caaggatgcc aacaggtgtc gcaagacaca      6420
```

```
tgcaatgagg ctctgaaaat tacatggcta ggagggaaac aggtggtcag cgtgatcatc    6480
caggtcaatg actatctctc agagaggcca aagataagag tcacaaccat tccaatcact    6540
caaaactatc tcggggcgga aggtagatta ttaaaattgg gtgatcgggt gtacatctat    6600
acaagatcat caggctggca ctctcaactg cagataggga tacttgatgt cagccaccct    6660
ttgactatca actggacacc tcatgaagcc ttgtctagac caggaaataa agagtgcaat    6720
tggtacaata agtgtccgaa ggaatgcata tcaggcgtat acactgatgc ttatccattg    6780
tcccctgatg cagctaacgt cgctaccgtc acgctatatg ccaatacatc gcgtgtcaac    6840
ccaacaatca tgtattctaa cactactaac attataaata tgttaaggat aaaggatgtt    6900
caattagagg ctgcatatac cacgacatcg tgtatcacgc attttggtaa aggctactgc    6960
tttcacatca tcgagatcaa tcagaagagc ctgaatacct tacagccgat gctctttaag    7020
actagcatcc ctaaattatg caaggccgag tcttaaattt aactgactag caggcttgtc    7080
ggccttgctg acactagagt catctccgaa catccacaat atctctcagt ctcttacgtc    7140
tctcacagta ttaagaaaaa cccagggtga atgggaagct tgccataggt catggatggg    7200
caggagtcct cccaaaaccc ttctgacata ctctatccag aatgccacct gaactctccc    7260
atagtcaggg ggaagatagc acagttgcac gtcttgttag atgtgaacca gccctacaga    7320
ctgaaggacg acagcataat aaatattaca aagcacaaaa ttaggaacgg aggattgtcc    7380
ccccgtcaaa ttaagatcag gtctctgggt aaggctcttc aacgcacaat aaaggattta    7440
gaccgataca cgtttgaacc gtacccaacc tactctcagg aattacttag gcttgatata    7500
ccagagatat gtgacaaaat ccgatccgtc ttcgcggtct cggatcggct gaccagggag    7560
ttatctagtg ggttccagga tctttggttg aatatcttca agcaactagg caatatagaa    7620
ggaagagagg ggtacgatcc gttgcaggat atcggcacca tcccggagat aactgataag    7680
tacagcagga atagatggta taggccattc ctaacttggt tcagcatcaa atatgacatg    7740
cggtggatgc agaagaccag accgggggga cccctcgata cctctaattc acataacctc    7800
ctagaatgca aatcatacac tctagtaaca tacggagatc ttgtcatgat actgaacaag    7860
ttgacattga cagggtatat cctaaccccct gagctggtct tgatgtattg tgatgttgta    7920
gaaggaaggt ggaatatgtc tgctgcaggg catctagata agaagtccat tgggataaca    7980
agcaaaggtg aggaattatg ggaactagtg gattccctct tctcaagtct tggagaggaa    8040
atatacaatg tcatcgcact attggagccc ctatcacttg ctctcataca actaaatgat    8100
cctgttatac ctctacgtgg ggcatttatg aggcatgtgt tgacagagct acagactgtt    8160
ttaacaagta gagacgtgta cacagatgct gaagcagaca ctattgtgga gtcgttactc    8220
gccattttcc atggaacctc tattgatgag aaagcagaga tcttttcctt ctttaggaca    8280
tttggccacc ccagcttaga ggctgtcact gccgccgaca aggtaagggc ccatatgtat    8340
gcacaaaagg caataaagct taagacccta tacgagtgtc atgcagtttt ttgcactatc    8400
atcataaatg ggtatagaga gaggcatggc ggacagtggc cccctgtgaa cttccctgat    8460
cacgtgtgtc tagaactaag gaacgctcaa gggtccaata cggcaatctc ttatgaatgt    8520
gctgtagaca actatacaag tttcatagge ttcaagtttc ggaagtttat agaaccacaa    8580
ctagatgaag atctcacaat atatatgaaa gacaaagcac tatccccag gaaggaggca    8640 tgggactctg tatacccgga tagtaatctg tactataaag ccccagagtc tgaagagacc    8700
cggcggctta ttgaagtgtt cataaatgat gagaatttca acccagaaga aattatcaat    8760
```

```
tatgtggagt caggagattg gttgaaagac gaggagttca acatctcgta cagtctcaaa    8820
gagaaagaga tcaagcaaga gggtcgtcta ttcgcaaaaa tgacttataa gatgcgagcc    8880
gtacaggtgc tggcagagac actactggct aaaggaatag gagagctatt cagcgaaaat    8940
gggatggtta aggagagat agacctactt aaaagattga ctactctttc tgtctcaggc     9000
gtccccagga ctgattcagt gtacaataac tctaaatcat cagagaagag aaacgaaggc    9060
atggaaaata agaactctgg ggggtactgg gacgaaaaga agaggtccag acatgaattc    9120
aaggcaacag attcatcaac agacggctat gaaacgttaa gttgcttcct cacaacagac    9180
ctcaagaaat actgcttaaa ctggagattt gagagtactg cattgttttgg tcagagatgc    9240
aacgagatat ttggcttcaa gaccttcttt aactggatgc atccagtcct tgaaaggtgt    9300
acaatatatg ttggagatcc ttactgtcca gtcgccgacc ggatgcatcg acaactccag    9360
gatcatgcag actctggcat tttcatacat aatcctaggg ggggcataga aggttactgc    9420
cagaagctgt ggaccttaat ctcaatcagt gcaatccacc tagcagctgt gagagtgggt    9480
gtcagggtct ctgcaatggt tcagggtgac aatcaagcta tagccgtgac atcaagagta    9540
cctgtagctc agacttacaa gcagaagaaa aatcatgtct atgaggagat caccaaaatat   9600
ttcggtgctc taagacacgt catgtttgat gtagggcacg agctaaaatt gaacgagacc    9660
atcattagta gcaagatgtt tgtctatagt aaaaggatat actatgatgg gaagattta    9720
ccacagtgcc tgaaagcctt gaccaagtgt gtattctggt ccgagacact ggtagatgaa    9780
aacagatctg cttgttcgaa catctcaaca tccatagcaa agctatcga aaatgggtat    9840
tctcctatac taggctactg cattgcgttg tataagacct gtcagcaggt gtgcatatca    9900
ctagggatga ctataaatcc aactatcagc ccgaccgtaa gagatcaata ctttaagggt    9960
aagaattggc tgagatgtgc agtgttgatt ccagcaaatg ttggaggatt caactacatg   10020
tctacatcta gatgctttgt tagaaatatt ggagaccccg cagtagcagc cctagctgat   10080
ctcaaaagat tcatcagagc ggatctgtta gacaagcagg tattatacag ggtcatgaat   10140
caagaacccg gtgactctag ttttctagat tgggcttcag acccttattc gtgtaaccctc  10200
ccgcattctc agagtataac tacgattata aagaatatca ctgctagatc tgtgctgcag   10260
gaatccccga atcctctact gtctggtctc ttcaccgaga ctagtggaga agaggatctc   10320
aacctggcct cgttccttat ggaccggaaa gtcatcctgc cgagagtggc tcatgagatc   10380
ctgggtaatt ccttaactgg agttagggag gcgattgcag ggatgcttga tacgaccaag   10440
tctctagtga gagccagcgt taggaaagga ggattatcat atgggatatt gaggaggctt   10500
gtcaattatg atctattgca gtacgagaca ctgactagaa ctctcaggaa accggtgaaa   10560
gacaacatcg aatatgagta tatgtgttca gttgagctag ctgtcggtct aaggcagaaa   10620
atgtggatcc acctgactta cgggagaccc atacatgggc tagaaacacc agacccttta   10680
gagctcttga ggggaatatt tatcgaaggt tcagaggtgt gcaagctttg caggtctgaa   10740
ggagcagacc ccatctatac atggttctat cttcctgaca atatagacct ggacacgctt   10800
acaaacggat gtccggctat aagaatcccc tattttggat cagccactga tgaaaggtcg   10860
gaagcccaac tcgggtatgt aagaaatcta agcaaacccg caaaggcggc catccggata   10920
gctatggtgt atacgtgggc ctacgggact gatgagatat cgtggatgga agccgctctt    10980
atagcccaaa caagagctaa tctgagctta gagaatctaa agctgctgac tcctgtttca   11040
acctccacta atcatctca taggttgaaa gatacggcaa cccagatgaa gttctctagt   11100
gcaacactag tccgtgcaag tcggttcata acaatatcaa atgataacat ggcactcaaa   11160
```

```
gaagcagggg agtcgaagga tactaatctc gtgtatcagc agattatgct aactgggcta  11220
agcttgttcg agttcaatat gagatataag aaaggttcct tagggaagcc actgatattg  11280
cacttacatc ttaataacgg gtgctgtata atggagtccc cacaggaggc gaatatcccc  11340
ccaaggtcca cattagattt agagattaca caagagaaca ataaattgat ctatgatcct  11400
gatccactca aggatgtgga ccttgagcta tttagcaagg tcagagatgt tgtacacaca  11460
gttgacatga cttattggtc agatgatgaa gttatcagag caaccagtat ctgtactgca  11520
atgacgatag ctgatacaat gtctcaatta gatagagaca acttaaaaga gatgatcgca  11580
ctagtaaatg acgatgatgt caacagcttg attactgagt ttatggtgat tgatgttcct  11640 ttatttttgct caacgttcgg gggtattcta gtcaatcagt ttgcatactc actctacggc  11700
ttaaacatca gaggaaggga agaaatatgg ggacatgtag tccggattct taagatacc  11760 tcccacgcag ttttaaaagt cttatctaat gctctatctc atcccaaaat cttcaaacga  11820
ttctggaatg caggtgtcgt ggaacctgtg tatgggccta acctctcaaa tcaggataag  11880
atactcttgg ccctctctgt ctgtgaatat tctgtggatc tattcatgca cgattggcaa  11940
gggggtgtac cgcttgagat ctttatctgt gacaatgacc cagatgtggc cgacatgagg  12000
aggtcctctt tcttggcaag acatcttgca tacctatgca gcttggcaga gatatctagg  12060
gatgggccaa gattagaatc aatgaactct ctagagaggc tcgagtcact aaagagttac  12120
ctggaactca catttcttga tgacccggta ctgaggtaca gtcagttgac tggcctagtc  12180
atcaaagtat tcccatctac tttgacctat atccggaagt catctataaa agtgttaagg  12240
acaagaggta taggagtccc tgaagtctta gaagattggg atcccgaggc agataatgca  12300
ctgttagatg gtatcgcggc agaaatacaa cagaatattc ctttgggaca tcagactaga  12360
gccccttttt gggggttgag agtatccaag tcacaggtac tgcgtctccg ggggtacaag  12420
gagatcacaa gaggtgagat aggcagatca ggtgttggtc tgacgttacc attcgatgga  12480
agatatctat ctcaccagct gaggctcttt ggcatcaaca gtactagctg cttgaaagca  12540
cttgaactta cctacctatt gagcccctta gttgacaagg ataaagatag gctatattta  12600
ggggaaggag ctggggccat gctttcctgt tatgacgcta ctcttggccc atgcatcaac  12660
tattataact caggggtata ctcttgtgat gtcaatgggc agagagagtt aaatatatat  12720
cctgctgagg tggcactagt ggggaagaaa ttaaacaatg ttactagtct gggtcaaaga  12780
gttaaagtgt tattcaacgg gaatcctggc tcgacatgga ttgggaatga tgagtgtgag  12840
gctttgattt ggaatgaatt acagaatagc tcgataggcc tagtccactg tgacatggag  12900
ggaggagatc ataaggatga tcaagttgta ctgcatgagc attacagtgt aatccggatc  12960
gcgtatctgg tggggatcg agacgttgtg cttataagca agattgctcc caggctggc  13020 acggattgga ccaggcagct cagcctatat ctgagatact gggacgaggt taacctaata  13080
gtgcttaaaa catctaaccc tgcttccaca gagatgtatc tcctatcgag gcaccccaaa  13140
tctgacatta tagaggacag caagacagtg ttagctagtc tcctcccttt gtcaaaagaa  13200
gatagcatca agatagaaaa gtggatctta atagagaagg caaaggctca cgaatgggtt  13260
actcgggaat tgagagaagg aagctcttca tcagggatgc ttagaccta ccatcaagca  13320 ctgcagacgt ttggctttga accaaacttg tataaattga gcagagattt cttgtccacc  13380
atgaacatag ctgatacaca caactgcatg atagctttca acagggtttt gaaggataca  13440
atcttcgaat gggctagaat aactgagtca gataaaaggc ttaaactaac tggtaagtat  13500
```

```
gacctgtatc ctgtgagaga ttcaggcaag ttgaagacaa tttctagaag acttgtgcta   13560
tcttggatat ctttatctat gtccacaaga ttggtaactg ggtcattccc tgaccagaag   13620
tttgaagcaa gacttcaatt gggaatagtt tcattatcat cccgtgaaat caggaacctg   13680
agggttatca caaaacttt attagacagg tttgaggata ttatacatag tataacgtat    13740
agattcctca ccaaagaaat aaagattttg atgaagattt taggggcagt caagatgttc   13800
ggggccaggc aaaatgaata cacgaccgtg attgatgatg gatcactagg tgatatcgag   13860
ccatatgaca gctcgtaata attagtccct atcgtgcaga acgatcgaag ctccgcggta   13920
cctggaagtc ttggacttgt ccatatgaca atagtaagaa aaacttacaa gaagacaaga   13980
aaatttaaaa ggatacatat ctcttaaact cttgtctggt gggtcggcat ggcatctcca   14040
cctcctcgcg gtccgacctg gcatccgaa ggaggacgca cgtccactcg gatggctaag    14100
ggagagctac gcgtggatcc ccgggaattc cgtaatcatg gtcatagctg tttcctgtgt   14160
gaaattgtta tccgctcaca attccacaca acatacgagc cggaagcata aagtgtaaag   14220
cctggggtgc ctaatgagtg agctaactca cattaattgc gttgcgctca ctgcccgctt   14280
tccagtcggg aaacctgtcg tgccagctgc attaatgaat cggccaacgc gcgggggagag  14340 gcggtttgcg tattgggcgc tcttccgctt cctcgctcac tgactcgctg cgctcggtcg   14400
ttcggctgcg gcgagcggta tcagctcact caaaggcggt aatacggtta ccacagaat    14460 caggggataa cgcaggaaag aacatgtgag caaaaggcca gcaaaaggcc aggaaccgta   14520
aaaaggccgc gttgctggcg ttttccata ggctccgccc ccctgacgag catcacaaaa   14580
atcgacgctc aagtcagagg tggcgaaacc cgacaggact ataaagatac caggcgtttc   14640
cccctggaag ctccctcgtg cgctctcctg ttccgaccct gccgcttacc ggatacctgt   14700
ccgcctttct cccttcggga agcgtggcgc tttctcatag ctcacgctgt aggtatctca   14760
gttcggtgta ggtcgttcgc tccaagctgg gctgtgtgca cgaaccccc gttcagcccg    14820 accgctgcgc cttatccggt aactatcgtc ttgagtccaa cccggtaaga cacgacttat   14880
cgccactggc agcagccact ggtaacagga ttagcagagc gaggtatgta ggcggtgcta   14940
cagagttctt gaagtggtgg cctaactacg gctacactag aagaacagta tttggtatct   15000
gcgctctgct gaagccagtt accttcggaa aaagagttgg tagctcttga tccggcaaac   15060
aaaccaccgc tggtagcggt ggtttttttg tttgcaagca gcagattacg cgcagaaaaa   15120
aaggatctca agaagatcct ttgatctttt ctacgggtc tgacgctcag tggaacgaaa     15180
actcacgtta agggattttg gtcatgagat tatcaaaaag gatcttcacc tagatccttt   15240
taaattaaaa atgaagtttt aaatcaatct aaagtatata tgagtaaact tggtctgaca   15300
gttaccaatg cttaatcagt gaggcaccta tctcagcgat ctgtctattt cgttcatcca   15360
tagttgcctg actccccgtc gtgtagataa ctacgatacg ggagggctta ccatctggcc   15420
ccagtgctgc aatgataccg cgagacccac gctcaccggc tccagattta tcagcaataa   15480
accagccagc cggaagggcc gagcgcagaa gtggtcctgc aactttatcc gcctccatcc   15540
agtctattaa ttgttgccgg gaagctagag taagtagttc gccagttaat agtttgcgca   15600
acgttgttgc cattgctaca ggcatcgtgg tgtcacgctc gtcgtttggt atggcttcat   15660
tcagctccgg ttcccaacga tcaaggcgag ttacatgatc ccccatgttg tgcaaaaaag   15720
cggttagctc cttcggtcct ccgatcgttg tcagaagtaa gttggccgca gtgttatcac   15780
tcatggttat ggcagcactg cataattctc ttactgtcat gccatccgta agatgctttt   15840
ctgtgactgg tgagtactca accaagtcat tctgagaata gtgtatgcgg cgaccgagtt   15900
```

-continued

```
gctcttgccc ggcgtcaata cgggataata ccgcgccaca tagcagaact ttaaaagtgc    15960
tcatcattgg aaaacgttct tcggggcgaa aactctcaag gatcttaccg ctgttgagat    16020
ccagttcgat gtaacccact cgtgcaccca actgatcttc agcatctttt actttcacca    16080
gcgtttctgg gtgagcaaaa acaggaaggc aaaatgccgc aaaaaaggga ataagggcga    16140
cacggaaatg ttgaatactc atactcttcc tttttcaata ttattgaagc atttatcagg    16200
gttattgtct catgagcgga tacatatttg aatgtattta gaaaaataaa caaatagggg    16260
ttccgcgcac atttccccga aaagtgccac ctgacgtcta agaaaccatt attatcatga    16320
cattaaccta taaaaatagg cgtatcacga ggcccttcg tc                       16362
```

<210> SEQ ID NO 10
<211> LENGTH: 338
<212> TYPE: PRT
<213> ORGANISM: artificial sequence
<220> FEATURE:
<223> OTHER INFORMATION: recombinant Ag85A protein

<400> SEQUENCE: 10

```
Met Gln Leu Val Asp Arg Val Arg Gly Ala Val Thr Gly Met Ser Arg
1               5                   10                  15

Arg Leu Val Val Gly Ala Val Gly Ala Ala Leu Val Ser Gly Leu Val
                20                  25                  30

Gly Ala Val Gly Gly Thr Ala Thr Ala Gly Ala Phe Ser Arg Pro Gly
            35                  40                  45

Leu Pro Val Glu Tyr Leu Gln Val Pro Ser Pro Ser Met Gly Arg Asp
        50                  55                  60

Ile Lys Val Gln Phe Gln Ser Gly Gly Ala Asn Ser Pro Ala Leu Tyr
65                  70                  75                  80

Leu Leu Asp Gly Leu Arg Ala Gln Asp Asp Phe Ser Gly Trp Asp Ile
                85                  90                  95

Asn Thr Pro Ala Phe Glu Trp Tyr Asp Gln Ser Gly Leu Ser Val Val
                100                 105                 110

Met Pro Val Gly Gly Gln Ser Ser Phe Tyr Ser Asp Trp Tyr Gln Pro
            115                 120                 125

Ala Cys Gly Lys Ala Gly Cys Gln Thr Tyr Lys Trp Glu Thr Phe Leu
        130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
            180                 185                 190

Ser Gly Leu Leu Asp Pro Ser Gln Ala Met Gly Pro Thr Leu Ile Gly
        195                 200                 205

Leu Ala Met Gly Asp Ala Gly Gly Tyr Lys Ala Ser Asp Met Trp Gly
    210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
            260                 265                 270

Glu Gly Phe Val Arg Thr Ser Asn Ile Lys Phe Gln Asp Ala Tyr Asn
```

```
                275                 280                 285
Ala Gly Gly Gly His Asn Gly Val Phe Asp Phe Pro Asp Ser Gly Thr
            290                 295                 300
His Ser Trp Glu Tyr Trp Gly Ala Gln Leu Asn Ala Met Lys Pro Asp
305                 310                 315                 320
Leu Gln Arg Ala Leu Gly Ala Thr Pro Asn Thr Gly Pro Ala Pro Gln
                325                 330                 335
Gly Ala

<210> SEQ ID NO 11
<211> LENGTH: 31
<212> TYPE: DNA
<213> ORGANISM: artificial sequence
<220> FEATURE:
<223> OTHER INFORMATION: primer

<400> SEQUENCE: 11
atagctagca tggtttcccg gccgggcttg c                                    31

<210> SEQ ID NO 12
<211> LENGTH: 27
<212> TYPE: DNA
<213> ORGANISM: artificial sequence
<220> FEATURE:
<223> OTHER INFORMATION: primer

<400> SEQUENCE: 12
taaggatccc taggcgccct ggggcgc                                         27

<210> SEQ ID NO 13
<211> LENGTH: 38
<212> TYPE: DNA
<213> ORGANISM: artificial sequence
<220> FEATURE:
<223> OTHER INFORMATION: primer

<400> SEQUENCE: 13
cacatcacga taccggtcta ctcgatggcc ggctcgtc                             38

<210> SEQ ID NO 14
<211> LENGTH: 39
<212> TYPE: DNA
<213> ORGANISM: artificial sequence
<220> FEATURE:
<223> OTHER INFORMATION: primer

<400> SEQUENCE: 14
cacatgcgaa taccggtaga ctaacgaact ctgcaggtc                            39

<210> SEQ ID NO 15
<211> LENGTH: 38
<212> TYPE: DNA
<213> ORGANISM: artificial sequence
<220> FEATURE:
<223> OTHER INFORMATION: primer

<400> SEQUENCE: 15
cacatcacga taccgggtac ctcgatggcc ggctcgtc                             38

<210> SEQ ID NO 16
<211> LENGTH: 39
<212> TYPE: DNA
<213> ORGANISM: artificial sequence
<220> FEATURE:
```

```
<223> OTHER INFORMATION: primer

<400> SEQUENCE: 16
cacatgcgaa taccgggtac ctaacgaact ctgcaggtc                    39

<210> SEQ ID NO 17
<211> LENGTH: 35
<212> TYPE: DNA
<213> ORGANISM: artificial sequence
<220> FEATURE:
<223> OTHER INFORMATION: primer

<400> SEQUENCE: 17
attgcggccg cgacatggtt tcccggccgg gcttg                        35

<210> SEQ ID NO 18
<211> LENGTH: 74
<212> TYPE: DNA
<213> ORGANISM: artificial sequence
<220> FEATURE:
<223> OTHER INFORMATION: primer

<400> SEQUENCE: 18
attgatgaac tttcacccta agtttttctt actacggcta ggcgccctgg ggcgcgggcc    60
cggtgttggg cgtg                                               74
```